US007122570B2

(12) United States Patent
Koppitz et al.

(10) Patent No.: US 7,122,570 B2
(45) Date of Patent: Oct. 17, 2006

(54) TETRAHYDROCARBAZOL DERIVATIVES AS LIGANDS FOR G-PROTEIN-COUPLED RECEPTORS (GPCR)

(75) Inventors: Marcus Karl Koppitz, Berlin (DE); Hans Peter Muhn, Berlin (DE); Kenneth Jay Shaw, Brookside, NJ (US); Holger Hess-Stump, Berlin (DE); Klaus Paulini, Maintal (DE)

(73) Assignee: Zentaris AG, Frankfurt (DE)

( * ) Notice: Subject to any disclaimer, the term of this patent is extended or adjusted under 35 U.S.C. 154(b) by 117 days.

(21) Appl. No.: 10/319,833

(22) Filed: Dec. 16, 2002

(65) Prior Publication Data

US 2003/0232873 A1 Dec. 18, 2003

Related U.S. Application Data

(60) Provisional application No. 60/341,878, filed on Dec. 21, 2001.

(30) Foreign Application Priority Data

Dec. 14, 2001 (DE) ............................... 101 64 564

(51) Int. Cl.
*A61K 31/403* (2006.01)
*C07D 209/88* (2006.01)
(52) U.S. Cl. .................. 514/411; 514/339; 546/276.7; 548/448; 548/439
(58) Field of Classification Search ................ 548/448, 548/439; 546/276.7; 514/411, 339
See application file for complete search history.

(56) References Cited

U.S. PATENT DOCUMENTS

| 3,634,420 | A | * | 1/1972 | Littell et al. ................. 544/142 |
| 3,862,953 | A | * | 1/1975 | Berger et al. ............ 546/276.7 |
| 3,931,222 | A | | 1/1976 | Cross et al. |
| 3,948,939 | A | * | 4/1976 | Alexander et al. .......... 548/448 |
| 4,292,323 | A | * | 9/1981 | Tahbaz ........................ 514/411 |
| 4,698,351 | A | * | 10/1987 | Hausberg et al. ........... 514/338 |
| 5,607,939 | A | | 3/1997 | Kato et al. |
| 5,708,187 | A | * | 1/1998 | Flaugh et al. ................ 548/439 |
| 5,877,199 | A | * | 3/1999 | Birdsall et al. .............. 514/411 |
| 5,952,335 | A | * | 9/1999 | Sugumi et al. .............. 514/274 |
| 6,156,772 | A | | 12/2000 | Goulet et al. |
| 6,177,440 | B1 | * | 1/2001 | Bach et al. .................. 514/292 |

FOREIGN PATENT DOCUMENTS

| DE | 24 25 767 | | 1/1975 |
| EP | 115607 A1 | * | 8/1984 |
| EP | 0 239 306 | | 9/1987 |
| EP | 0 679 642 | | 11/1995 |
| GB | 1436893 | * | 5/1976 |
| WO | WO 98 55116 | | 12/1998 |
| WO | WO-01/07409 A1 | * | 2/2001 |

OTHER PUBLICATIONS

CA Registry No. 344869-00-7, entry date into Registry File on STN is Jul. 8, 2001.*
CA Registry No. 344447-16-1, entry date into Registry File on STN is Jul. 3, 2001.*
Chakravarty et al., CA 135:239232, Jun. 2001.*
Gallagher, Science of Synthesis, (Mar. 1, 2001), vol. 10, pp. 693-744.*
CA Registry No. 14171-79-0, entry date into Registry File on STN is Nov. 16, 1984.*
Rice et al., Journal of Medicinal Chemistry (1970), 13(2), pp. 308-311.*
Canas-Rodriguez et al., CA 106:67041, (1987).*
Scott et al., CA 102:55867 (1985).*
Rice et al., CA 76:14239, (1972).*
Erra-Balsells, CA 112:157996, (1990).*
Deohra et al., CA 56:66801, (1962).*
Millet et al., CA 131:257856, (1999).*
Narasimhan et al., CA 100:138926, (1984).*
Utley et al., CA 89:215158, (1978).*
Hahn et al., CA 82:43129, (1975).*
Smith et al., CA 72:55144, (1970).*
Noland et al., Tetrahedron, (1996), vol. 52, No. 13, pp. 4555-4572.*
Noland et al., Journal of Organic Chemistry (1979), 44(24), pp. 4402-4410.*
Eitel et al., Journal of Organic Chemistry (1990), 55(19), pp. 5368-5374.*
Narasimhan et al., CA 100:138888, (1984).*
Marinelli, CA 97:144721, (1982).*
Bergman et al., CA 72:67124, (1970).*
Sparatore et al., CA 70:96538, (1969).*
Plant et al., CA 23:833, (1929).*
Hu et al., CA 121:151520, (1994).*
Bhattacharyya et al., CA 109:230704, (1988).*
Kusurkar et al., CA 107:115452, (1987).*
Tsunashima et al., CA 98:4457, (1983).*
Bozzini et al., CA 91:107697, (1979).*
Bhattacharyya et al., CA 86:106843, (1977).*

(Continued)

*Primary Examiner*—Laura L. Stockton

(57) ABSTRACT

This invention provides new tetrahydrocarbazole derivatives that act as ligands for G-protein-coupled receptors (GPCR), especially as antagonists of the gonadotropin-releasing hormone (GnRH). A pharmaceutical composition that contains these new tetrahydrocarbazole derivatives as well as a process for the production of the new tetrahydrocarbazole derivatives are also provided. Moreover, this invention relates to the administration of tetrahydrocarbazole derivatives for treating pathologic conditions that are mediated by GPCR, especially for inhibiting GnRH, in mammals, especially humans, who require such an administration, as well as the use of tetrahydrocarbazole derivatives for the production of a pharmaceutical agent for treating GPCR-mediated pathologic conditions, especially for inhibiting GnRH.

20 Claims, No Drawings

OTHER PUBLICATIONS

Gupta et al., CA 85:21006, (1976).*
Rashidyan et al., CA 71:21972, (1969).*
Berlin et al., CA 70:96537, (1969).*
Yokoyama et al., CA 113:172402, (1990).*
Alekseev et al., CA 112:229050, (1990).*
Kuroki et al., CA 95:150332, (1981).*
Kwalwasser, CA 91:21453, (1979).*
Namis et al., CA 67:73028, (1967).*
Cranwell et al., CA 59:3675, (1963).*
Maki et al., Chemical & Pharmaceutical Bulletin (1973), 21(11), pp. 2460-2465.*
D.J. Davies et al., *Mapping the melatonin receptor. 5. Melatonin agonists and antagonists derived from tetrahydrocyclopent[b]indoles, Tetrahydrocarbazoles and Hexahydrocyclohept[b]indoles*, J. Med. Chem., 1998, 41, pp. 451-467; XP-002215114.

* cited by examiner

TETRAHYDROCARBAZOL DERIVATIVES AS LIGANDS FOR G-PROTEIN-COUPLED RECEPTORS (GPCR)

This application claims the benefit of the filing date of U.S. Provisional Application Ser. No. 60/341,878 filed Dec. 21, 2001.

This invention relates to new tetrahydrocarbazole derivatives, the ligands of G-protein-coupled receptors, and especially antagonists of the gonadotropin-releasing hormone, their production, their use as well as pharmaceutical compositions that comprise these tetrahydrocarbazole derivatives. This invention also relates to a process for treating pathologic conditions that are mediated by G-protein-coupled receptors in a mammal, especially a human.

TECHNICAL BACKGROUND

The structural element that is common to all members of the family of the G-protein-coupled receptors (GPCR) is the presence of seven transmembrane-alpha-helical segments that are connected to one another by alternating intracellular and extracellular loops, whereby the amino-terminus is found on the extracellular side, and the carboxy-terminus is found on the intracellular side. The family of GPCRs can be divided into several subfamilies (essentially families A, B and C) with additional sequence homologies within these subfamilies. Since GPCRs are involved primarily in signal reception and transmission, a number of physiological functions are influenced by them. GPCR ligands are therefore potentially suitable as medications for therapy and prevention of a large number of pathologic conditions. A small overview on diseases that can be treated with GPCR ligands is provided in Table I in S. Wilson et al., *Pharmaceutical News* 2000, 7(3).

The majority of known GPCR ligands are of peptidic structure. Peptidic receptor ligands, however, often have some significant drawbacks, such as, for example, low bioavailability and metabolic instability. Therefore, in recent years, an intensified search has been run for ligands in the form of small, non-peptidic molecules. So-called "privileged structures" play a special role in the search for new, non-peptidic receptor ligands. These "privileged structures" are those basic molecular structures that prepare ligands for a number of different receptors. The term "privileged structures" was used for the first time by Evans et al. in connection with the benzodiazepine-based CCK (cholecystokinin)-A antagonists from the natural substance Asperlicin (B. E. Evans et al., *J. Med. Chem.* 1988, 31, 2235). For proteases, it has already been known for a long time, for example, that certain structure classes can be used as inhibitors for various enzymes. While in the past primarily mechanism-based inhibitors were described for various proteases, more recently, however, and more and more often, examples of compounds that readily fit into the active binding regions of various enzymes because of their three-dimensional structure have been found (cf. M. Whittaker, *Cur. Opin. Chem. Biol.* 1998, 2, 386; A. S. Ripka et al., ibid., 441). Such "privileged structures" were also already described for GPCRs. Examples to this end, in addition to the above-mentioned benzodiazepines, are also peptoids, 4-substituted 4-arylpiperidines, but also special β-Turn mimetic agents that are made rigid (B. A. Bunin et al., *Ann. Rep. Med. Chem.* 1999, 34, 267; R. N. Zuckermann et al., *J. Med. Chem.* 1994, 37, 2678; G. C B. Harriman, *Tetrahedron Lett.* 2000, 41, 8853). A survey to this end is found in A. A. Patchett et al., *Ann. Rep. Med. Chem.* 1999, 35, 289. With the tetrahydrocarbazole derivatives according to this invention, another class of "privileged structures" is made available for GPCRs.

Although this invention generally prepares ligands for GPCRs, the compounds that are prepared by this invention are especially suitable as ligands for a certain representative of the class of GPCRs, namely the gonadotropin-releasing hormone receptor (GnRH receptor). The GnRH receptor can be classified in subfamily A of the GPCRs (cf. U. Gether et al., *Endocrine Reviews* 2000, 21(1), 90).

GnRH is a hormone that mainly, but not exclusively, is synthesized in mammals by the nerve cells of the hypothalamus, is transported via the portal veins into the pituitary gland and is released in a regulated manner to the gonadotropic cells. By interaction with its receptor that has seven transmembrane domains, GnRH stimulates the production and the release of gonadotropic hormones by means of the second messenger inositol-1,4,5-triphosphate and $Ca^{2+}$ ions. The gonadotropin-luteinizing hormone (LH) that is released by GnRH and the follicle-stimulating hormone (FSH) stimulate the production of sex steroids and the gamete maturation in both sexes. In addition to GnRH (also referred to as GnRH1), there are two other forms of GnRH, namely GnRH2 and 3.

The GnRH receptor is used as a pharmacological target in a number of diseases, which are dependent on a functioning sex hormone production, for example prostate cancer, premenopausal breast cancer, endometriosis and uterine fibroids. In the case of these diseases, GnRH superagonists or GnRH antagonists can be used successfully. In particular, the male birth control in combination with a substitution dose of androgens forms a possible further indication.

An advantage of GnRH antagonists in comparison to GnRH superagonists is their immediate effectiveness in the blocking of the gonadotropin secretion. Superagonists initially produce an overstimulation of the hypophysis, which results in increased gonadotropin and sex steroid releases. This hormonal reaction is only completed after a certain delay based on the desensitization and downward-adjustment of the GnRH receptor concentrations. Therefore, GnRH superagonists, both alone and in combination with testosterone, may not be able to suppress sperm production in males effectively and thus are not suitable for male birth control. In contrast to this, peptidic GnRH antagonists, especially in combination with a substitution dose of androgen, are able to bring about a significant oligozoospermia in humans.

Peptidic GnRH antagonists, however, have a number of drawbacks. They have a considerably lower effectiveness as superagonists and consequently have to be administered at considerably higher dosages. Their oral bio-availability is also low, so that they have to be administered by injection. Repeated injections lead in turn to a reduction in compliance. Moreover, the synthesis of peptidic GnRH antagonists in comparison to non-peptidic compounds is costly and labor-intensive.

Quinoline derivatives as non-peptidic GnRH antagonists are disclosed in, for example, WO 97/14682. To date, however, it was not possible to market any non-peptidic GnRH antagonists.

TECHNICAL OBJECT

The object on which this invention is based consists in providing new compounds that are suitable for treatment of pathologic conditions that are mediated by GPCR and that have in particular a GnRH-inhibiting (GnRH-antagonistic)

action. The new GPCR ligands, preferably GnRH antagonists, should as much as possible be superior to the known peptide compounds and represent an effective alternative or improvement relative to known non-peptidic compounds. The new GPCR ligands, especially GnRH antagonists, are to have primarily high effectiveness and as high an oral bioavailability as possible. In addition, they should be able to be synthesized simply and with as low costs as possible. Pharmaceutical compositions that contain the new non-peptidic GPCR compounds, especially GnRH antagonists, are also provided by this invention.

Another object on which this invention is based is the provision of new GPCR ligands, preferably GnRH antagonists, for use as pharmaceutical agents or for use for the production of pharmaceutical agents that comprise the GPCR ligands, preferably GnRH antagonists.

Moreover, an object of this invention is to provide a process for treating pathologic conditions that are mediated by GPCR, especially for inhibiting GnRH, in a mammal, especially a human.

All of these objects are achieved in a surprising way by the provision of new tetrahydrocarbazole derivatives, the pharmaceutical compositions that contain these tetrahydrocarbazole derivatives, the process for the production of these tetrahydrocarbazole derivatives as well as the process for treating pathologic conditions that are mediated by GPCR, preferably for inhibiting GnRH, in a mammal, especially a human, by administering the tetrahydrocarbazole derivatives or the use of the tetrahydrocarbazole derivatives for the production of pharmaceutical agents for treating pathologic conditions that are mediated by GPCR, especially for GnRH inhibition.

SUMMARY OF THE INVENTION

In a first aspect, this invention provides new tetrahydrocarbazole derivatives of general formula (I).

In a second aspect, pharmaceutical compositions are provided that comprise at least one of the new tetrahydrocarbazole derivatives of general formula (I).

In a third aspect, this invention provides tetrahydrocarbazole derivatives of general formula (I) for use as pharmaceutical agents.

In another aspect, this invention relates to the use of a tetrahydrocarbazole derivative of general formula (I) for the production of a pharmaceutical agent for treating pathologic conditions that are mediated by GPCR, especially for inhibiting the GnRH. This invention also relates to a process for treating pathologic conditions that are mediated by GPCR, especially for inhibiting GnRH in a mammal, preferably a human, whereby an effective amount of a compound of general formula (I) according to the invention is administered to a mammal, preferably a human, who requires such a treatment.

In addition, this invention provides a process for the production of tetrahydrocarbazole derivatives of general formula (I). This process comprises, for example, the steps of condensation of a cyclohexanone derivative that is anchored to a solid phase and suitably substituted with a suitably substituted phenylhydrazine derivative, a subsequent derivatization depending on the desired structure of the final compound and finally cleavage from the solid phase and isolation of the product.

DETAILED DESCRIPTION OF THE INVENTION

In a first aspect of this invention, new tetrahydrocarbazole compounds of general formula (I)

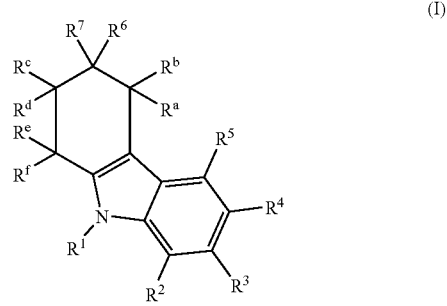

are provided, in which radical $R^1$ is a hydrogen atom, a $C_2$–$C_6$ alkenyl radical or a $C_1$–$C_6$ alkyl radical, and can optionally be substituted with an aryl radical, hetaryl radical or the group —$COOR^{11}$, whereby the aryl or hetaryl radical can be substituted with up to three substituents, which are selected independently of one another from the group that consists of —$NO_2$, —$CH_3$, —$CF_3$, —$OCH_3$, —$OCF_3$ and halogen atoms, and radical $R^{11}$ is a hydrogen atom, a $C_1$–$C_{12}$ alkyl radical, a $C_1$–$C_{12}$ aralkyl radical, an aryl radical, a hetaryl radical or the group —$COCH_3$, and optionally can be substituted with a substituent that is selected from the group that consists of —$CONH_2$, —$COCH_3$, —$COOCH_3$, —$SO_2CH_3$ and aryl radicals;

radicals $R^2$, $R^3$, $R^4$ and $R^5$, independently of one another, in each case are a hydrogen atom, a halogen atom, the group —$COOH$, —$CONH_2$, —$CF_3$, —$OCF_3$, —$NO_2$, —$CN$, a $C_1$–$C_6$ alkyl radical, a $C_1$–$C_6$ alkenyl radical, a $C_1$–$C_6$ alkoxy radical, a $C_1$–$C_{12}$ aralkyl radical, an aryl or hetaryl radical;

radical $R^6$ is the group —$CONR^8R^9$, —$COOR^8$, —$CH_{21}NR^8R^9$, —$CH_2R^8$, —$CH_2OR^8$ or a $C_1$–$C_{12}$ alkenyl radical, which optionally is substituted with radicals $R^8$ and $R^9$, whereby radicals $R^8$ and $R^9$, independently of one another, in each case are a hydrogen atom, a $C_1$–$C_{12}$ alkyl radical, a $C_1$–$C_{12}$ aralkyl radical, a $C_1$–$C_{12}$ hetaralkyl radical, an aryl radical or hetaryl radical, which can be substituted with one or more substituents, which are selected from the group that consists of —$OH$, —$NH_2$, —$CONHR^{10}$, —$COOR^{10}$, —$NH$—$C(=NH)$—$NH_2$ and halogen atoms, whereby radical $R^{10}$ is a hydrogen atom, a $C_1$–$C_{12}$ alkyl radical, a $C_1$–$C_{12}$ aralkyl radical, an aryl radical or hetaryl radical, and optionally is substituted with the group —$CON(R^{11})_2$, or whereby radicals $R^8$ and $R^9$ together can form a ring structure that either consists exclusively of carbon atoms or, in mixed form, consists of carbon atoms and heteroatoms;

radical $R^7$ is a hydrogen atom, a $C_1$–$C_{12}$ alkyl radical, a $C_1$–$C_{12}$ alkenyl radical, a $C_1$–$C_{12}$ aralkyl radical, an aryl radical or a hetaryl radical, the group —$NR^{12}R^{13}$, —$NHCOR^{14}$, —$NHCONHR^{14}$, —$NHCOOR^4$ or —$NHSO_2R^{14}$, and optionally can be substituted with one or more substituents, which are selected from the group that consists of —$OH$, —$NH_2$, —$CONH_2$, —$COOH$ and halogen atoms, radicals $R^{12}$ and $R^{13}$, independently of one another, in each case are a hydrogen atom, a $C_2$–$C_6$ alkenyl radical or a $C_1$–$C_{12}$ alkyl radical and optionally can be substituted with one or more aryl or hetaryl radicals, which in turn can be substituted with up to three substituents, which independently of one another are selected from the group that consists of —$NO_2$, —$CH_3$, —$CF_3$, —$OCH_3$, —$OCF_3$ and halogen atoms, and radical $R^4$ is a hydrogen atom, a $C_1$–$C_{12}$ alkyl radical, a $C_1$–$C_{12}$ alkenyl radical, a $C_1$–$C_{12}$ aralkyl radical, an aryl radical or a hetaryl radical, which optionally can be substituted with one or more substituents, which are selected from the group that consists of —$NO_2$, —$CH_3$, —$OR^{11}$, —$CF_3$, —$OCF_3$, —OH, —$N(R^{11})_2$, —$OCOR^{11}$, —COOH, —$CONH_2$, —$NHCONHR^{11}$, —$NHCOOR^{11}$ and halogen atoms;

and radicals $R^a$, $R^b$, $R^c$, $R^d$, $R^e$ and $R^f$, independently of one another, in each case are a hydrogen atom, a halogen atom, the group —COOH, —$CONH_2$, —$CF_3$, —$OCF_3$, —$NO_2$, —CN, a $C_1$–$C_6$ alkyl radical, $C_1$–$C_6$ alkoxy radical, an aryl radical or a hetaryl radical;

provided that the compound of general formula (I) is not selected from the group that consists of 3-amino-1,2,3,4-tetrahydrocarbazole-3-carboxylic acid, 3-amino-6-methoxy-1,2,3,4-tetrahydrocarbazole-3-carboxylic acid, 3-amino-6-benzyloxy-1,2,3,4-tetrahydrocarbazole-3-carboxylic acid, 3-acetamido-1,2,3,4-tetrahydrocarbazole-3-carboxylic acid, methyl-3-acetamido-1,2,3,4-tetrahydrocarbazole-3-carboxylate, -(–)-menthyl-3-acetamido-1,2,3,4-tetrahydrocarbazole-3-carboxylate or 3-tert-butoxycarbonyl-amino-1,2,3,4-tetrahydrocarbazole-3-carboxylic acid.

Compounds of general formula (I) as indicated above with all meanings for the radicals that are contained in (I) that are indicated above are an embodiment of the invention, whereby radical $R^{11}$ is a heteroalkyl radical or a hetaryalkyl radical.

The basic tetrahydrocarbazole structures of the compounds that are excluded by name above from the compounds that fall under the definition of general formula (I) were presented by Y. Maki et al. in *Chem. Pharm. Bull.* 1973, 21 (11), 2460–2465 as well as by R. Millet et al. in *Letters in Peptide Science* 1999, 6, 221–233.

The terms that are indicated to explain the compounds of general formula (I) have in particular the following meaning:

$C_1$–$C_6$ or $C_1$–$C_{12}$ "alkyl radical" is defined as a branched or unbranched, cyclic or noncyclic, optionally substituted alkyl group with 1 to 6 or 1 to 12 carbon atoms. Representative examples of such alkyl groups include methyl, ethyl, n-propyl, iso-propyl, n-butyl, iso-butyl, tert-butyl, n-pentyl, 2,2-dimethylpropyl, 3-methylbutyl, n-hexyl, n-heptyl, n-octyl, n-nonyl, n-decyl, n-undecyl and n-dodecyl groups as well as cyclic groups, especially cyclopropyl, cyclobutyl, cyclopentyl, cyclohexyl, cycloheptyl groups, 1-cyclopropyl, 1-cyclobutyl, 1-cyclopentyl, 1-cyclohexyl, 1-cycloheptylethyl, 2-cyclopropyl, 2-cyclobutyl, 2-cyclopentyl, 2-cyclohexyl, 2-cycloheptylethyl groups and the like, but they are not limited to the latter.

$C_2$–$C_6$ "Alkenyl radical" is defined as a branched or unbranched, cyclic or non-cyclic, unsaturated alkenyl group, optionally substituted in one or more places, with 2 to 6 carbon atoms. Representative examples of such alkenyl groups include vinyl, allyl, prop-1-enyl, but-1-enyl, but-2-enyl, but-3-enyl, buta-1,3-dienyl, pent-1-enyl, pent-2-enyl, pent-3-enyl, pent-4-enyt, penta-1,3-dienyl, penta-1,4-dienyl, penta-2,3-dienyl, isoprenyl, hex-1-enyl, hex-2-enyl, hex-3-enyl, hex-4-enyl, hex-5-enyl, hexa-1,3-dienyl, hexa-1,4-dienyl, hexa-1,5-dienyl, hexa-2,4-dienyl, hexa-2,5-dienyl, hexa-1,4-dienyl, hexa-1,3,5-trienyl groups and the like, but they are not limited to the latter.

$C_2$–$C_6$ "Alkoxy radical" is defined as a branched or unbranched, cyclic or non-cyclic, optionally substituted alkoxy group with 2 to 6 carbon atoms. Representative examples of such alkoxy groups include methoxy, ethoxy, n-propoxy, iso-propoxy, n-butoxy, iso-butoxy, tert-butoxy, n-pentoxy, n-hexoxy, cyclohexyloxy groups and the like, but they are not limited to the latter.

$C_1$–$C_{12}$ "Aralkyl radical" is defined as an alkyl radical with 1 to 12 carbon atoms that is substituted by one or more aryl radicals. Representative examples of such aralkyl groups for the purposes of this invention include benzyl, 1-phenylethyl, 1-phenylpropyl, 1-phenylbutyl, 1-phenylhexyl, 1-phenyl-2-methylethyl, 1-phenyl-2-ethylethyl, 1-phenyl-2,2-dimethylethyl, benzhydryl, triphenylmethyl, 2- or 3-naphthylmethyl, 2-phenylethyl, 3-phenylpropyl, 4-phenylbutyl, 5-phenylpentyl groups and the like, but they are not limited to the latter. Accordingly, a "hetaralkyl radical" is an alkyl radical that is substituted by a heteroaryl radical.

"Aryl radical" is defined as an optionally substituted monocyclic or polycyclic aromatic group. Representative examples of such aryl groups include phenyl groups, naphthyl groups, and the like, but they are not limited to the latter.

The designation "hetaryl radical" is identical to the designation "heteroaryl radical" and stands for an aryl group, as defined above, that in the structure thereof comprises one or more heteroatoms, in particular nitrogen, phosphorus, oxygen, sulfur and arsenic atoms. Representative examples of such hetaryl or heteroaryl groups include unsubstituted hetaryl radicals as well as substituted hetaryl radicals, in particular imidazolyl, pyridyl, quinolinyl groups and the like, but they are not limited to the latter.

The designation "ring structure" comprises optionally substituted monocyclic or polycyclic ring structures with a different number of ring members, but in particular five-, six- and seven-membered ring structures. In these ring structures, in addition to carbon atoms, one or more heteroatoms, such as in particular nitrogen, phosphorus, oxygen, sulfur and arsenic atoms, can also be included. The ring structures can comprise saturated, but also partially or completely unsaturated, structural elements. Representative examples of such ring structures include aza, oxa, thia, phosphacyclopentane, phosphacyclohexane, phosphacycloheptane, diaza, dioxa, dithia, diphosphacyclopentane, diphosphacyclohexane, and diphosphacycloheptane basic ring structures and the like, as well as basic ring structures with mixed heteroatom exchange, but they are not limited to the latter.

"Halogen atoms" comprise in particular fluorine, chlorine, bromine and iodine atoms, especially preferably chlorine atoms.

At this point, it can also be pointed out that in addition to the compounds of general formula (I) that are mentioned in the art, as defined above, physiologically compatible derivatives or analogs, in particular also salts of these compounds are also included by this invention.

In addition, it can be noted at this point that the designation "receptor ligand" or "ligand" for the purposes of this invention is to designate any compound that binds in any way to a receptor (in this invention, the receptor is a GPCR receptor, preferably a GnRH receptor) and triggers either an activation, an inhibition or other conceivable action in the case of this receptor. The term "ligand" thus comprises agonists, antagonists, partial agonists/antagonists and other ligands that cause an action in the reactor that is similar to the action of agonists, antagonists or partial agonists/antagonists. The compounds of general formula (I) according to the invention are preferably antagonists of the GnRH.

New tetrahydrocarbazole derivatives of general formula (I) according to the invention, in which radical $R^7$ is not a hydrogen atom, if radical $R^6$ is simultaneously an alkyl radical, are an embodiment of this invention.

Compounds of general formula (I) in which radical $R^7$ is not a hydrogen atom in any case are another embodiment of this invention.

Preferred new tetrahydrocarbazole derivatives of general formula (I) according to the invention are any compounds in which the radicals $R^a$, $R^b$, $R^c$, $R^d$, $R^e$ and $R^f$ are hydrogen atoms.

Also preferred new tetrahydrocarbazole derivatives of general formula (I) according to the invention are any compounds in which radical $R^1$ is a hydrogen atom.

Preferred new tetrahydrocarbazole derivatives of general formula (I) according to the invention are in addition any compounds in which radicals $R^2$, $R^3$, $R^4$ and/or $R^5$ are not hydrogen atoms. Especially preferred in this case are any compounds of general formula (I) in which radicals $R^2$, $R^3$, $R^4$ and $R^5$, independently of one another, are methyl, chloro or methoxy radicals. Quite especially preferred in this case are any compounds of general formula (I) in which at least radical $R^2$ is not a hydrogen atom, especially the compounds Phenylmethyl-[(1S,2S)-1-[[[(3R)-3-[[[(1S)-1-(aminocarbonyl)-2-methylpropyl]amino]-carbonyl]-2,3,4,9-tetrahydro-8-methyl-1H-carbazol-3-yl]amino]carbonyl]-2-methylbutyl]carbamate (compound No. 150a in the examples), Phenylmethyl-[(1S,2S)-1-[[[(3R)-3-[[[(1S)-1-(aminocarbonyl)-2-methylpropyl]amino]-carbonyl]-6-chloro-2,3,4,9-tetrahydro-1H-carbazol-3-yl]amino]-carbonyl]-2-methylbutyl]carbamate (148a), Phenylmethyl-[(1S,2S)-1-[[[(3R)-3-[[[(1S)-1-(aminocarbonyl)-2-methylpropyl]amino]-carbonyl]-2,3,4,9-tetrahydro-8-methoxy-1H-carbazol-3-yl]amino]carbonyl]-2-methylbutyl]carbamate (147a).

Preferred new tetrahydrocarbazole derivatives of general formula (I) according to the invention are also any compounds in which $R^6$ is a hydrophobic radical that comprises alkyl, aryl and/or hetaryl structures and that carries a hydrogen bridge-donor-acceptor system at a distance of two to four single bonds, counting from the carbon atoms that are substituted by radicals $R^6$ and $R^7$. Especially preferred are compounds of general formula (I), whereby radical $R^6$ is:

a carbonyl phenylalanylamide radical, in particular the compound phenylmethyl-[(1S,2S)-1-[[[(3R)-3-[[[(1S)-2-amino-2-oxo-1-(phenylmethyl)ethyl]amino]carbony]-2,3,4,9-tetrahydro-1H-carbazol-3-yl]amino]carbonyl]-2-methylbutyl]carbamate (66), a carbonyl isoleucylamide radical, in particular the compound phenylmethyl [(1S,2S)-1-[[[(3R)-3-[[[(1S,2S)-1-(aminocarbonyl)-2-methylbutyl]amino]carbonyl]-2,3,4,9-tetrahydro-1H-carbazol-3-yl]amino]carbonyl]-2-methylbutyl]carbamate (64), a carbonyl valyl-4-aminobenzoic acid amide radical, in particular the compound phenylmethyl [(1S,2S)-1-[[[(3R)-3-[[[(1S)-1-[[[4-(aminocarbonyl)phenyl]amino]-2-methylpropyl]amino]carbonyl]-2,3,4,9-tetrahydro-1H-carbazol-3-yl]amino]carbonyl]-2-methylbutyl]carbamate (45), a carbonyl valyl-N-methylamide radical, in particular the compound phenylmethyl [(1S,2S)-2-methyl-1-[[[(3R)-2,3,4,9-tetrahydro-3-[[[(1S)-2-methyl-1-[(methylamino)carbonyl]-propyl]amino]carbonyl]-1H-carbazol-3-yl]amino]carbonyl]butyl]carbamate (222a), a methyloxymethyl-4-pyridyl radical, in particular the compound 2,3,4,9-tetrahydro-3-(3-phenylpropyl)-O-(4-pyridinylmethyl)-1H-carbazole-3-methanol (287), a carboxyl radical, in particular the compound 2,3,4,9-tetrahydro-3-(3-phenylpropyl)-1H-carbazole-3-carboxylic acid (273), or a propenoic acid ethyl ester radical, in particular the compound ethyl 3-[2,3,4,9-tetrahydro-3-(3-phenylpropyl)-1H-carbazol-3-yl]-2-propenoate (289).

Also especially preferred are compounds of general formula (I), in which radical $R^6$ is:

a carbonylvalylamide radical, in particular the compound phenylmethyl [(1S,2S)-1-[[[(3R)-3-[[[(1S)-1-(aminocarbonyl)-2-methylpropyl]amino]carbonyl]-2,3,4,9-tetrahydro-1H-carbazol-3-yl]amino]carbonyl]-2-methylbutyl]carbamate (58), a carbonylthreonylamide radical, in particular the compound phenylmethyl [(1S,2S)-1-[[[(3R)-3-[[[(1S,2R)-1-(aminocarbonyl)-2-hydroxypropyl]amino]-carbonyl]-2,3,4,9-tetrahydro-1H-carbazol-3-yl]amino]carbonyl]-2-methylbutyl]carbamate, a cyclic carboxamide radical (such as, for example, a carbonylpropylamide radical, in particular the compound phenylmethyl [(1S,2S)-1-[[[(3R)-3-[[(2S)-2-(aminocarbonyl)-1-pyrrolidinyl]carbonyl]-2,3,4,9-tetrahydro-1H-carbazol-3-yl]amino]-carbonyl]-2-methylbutyl]carbamate (181a)

or a carbonyloctahydroindolyl-2-carboxamide radical, in particular the compound phenylmethyl [(1S,2S)-1-[[[(3R)-3-[[(2S)-2-(aminocarbonyl)octahydro-1H-indol-1-yl]carbonyl]-2,3,4,9-tetrahydro-1H-carbazol-3-yl]amino]carbonyl]-2-methylbutyl]-carbamate (190a)), a 4-carboxamidophenylcarboxamide radical, in particular the compound phenylmethyl [(1S,2S)1-[[[(3R)-3-[[[4-(aminocarbonyl)phenyl]amino]carbonyl]-2,3,4,9-tetrahydro-1H-carbazol-3-yl]amino]carbonyl]-2-methylbutyl]carbamate (62), a methylaminomethyl-2-pyridyl radical, in particular the compound 2,3,4,9-tetrahydro-3-(3-phenylpropyl)-N-(2-pyridinylmethyl)-1H-carbazole-3-methanamine (279), a carbonylvalinol radical, in particular the compounds phenylmethyl [(1S,2S)-1-[[[(3S)-3-[[[(1S)-1-(hydroxymethyl)-2-methylpropyl]amino]carbonyl]-2,3,4,9-tetrahydro-1H-carbazol-3-yl]amino]carbonyl]-2-methylbutyl]carbamate (267b)

and 2,3,4,9-tetrahydro-N-[(1S)-1-(hydroxymethyl)-2-methylpropyl]-3-(3-phenylpropyl)-1H-carbazole-3-carboxamide (276)

or a methylvalinol radical, in particular the compound (2S)-3-methyl-2-[[[2,3,4,9-tetrahydro-3-(3-phenylpropyl)-1H-carbazol-3-yl]methyl]amino]-1-butanol (284).

Preferred, new tetrahydrocarbazole derivatives of general formula (I) according to the invention are also any compounds in which $R^7$ is a hydrophobic radical that comprises alkyl, aryl and/or hetaryl structures. Especially preferred in this case are compounds of general formula (I), in which radical $R^7$ is:

a 2,3-biphenylpropionylamino radical, in particular the compound N-[[(3R)-2,3,4,9-tetrahydro-3-[(1-oxo-2,3-diphenylpropyl)amino]-1H-carbazol-3-yl]carbonyl]-L-valyl-L-aspartamide (18), an indanoylamino radical, in particular the compound (3R)-N-[(1S)-1-(aminocarbonyl)-2-methylpropyl]-3-

[[(2,3-dihydro-1H-inden-1-yl)carbonyl]amino]-2,3,4,
9-tetrahydro-1H-carbazole-3-carboxamide (162a),
an indolylacetylamino radical, in particular the compound
(3S)-N-[(1S)-1-(aminocarbonyl)-2-methylpropyl]-2,3,
4,9-tetrahydro-3-[(1H)-indol-3-ylacetyl)amino]-1H-
carbazole-3-carboxamide (164b),
a 2-naphthylacetylamino radical, in particular the compound (3S)-N-[(1S)-1-(aminocarbonyl)-2-methylpropyl]-2,3,4,9-tetrahydro-3-[(2-naphthalenylacetyl)amino]-1H-carbazole-3-carboxamide (161b),
or a 3-propionylamino radical. A further preferred compound is N-[[(3R)-2,3,4,9-N-[[(3R)-2,3,4,9-tetrahydro-3-[[(2S,3S)-3-methyl-1-oxo-2-[(1-oxo-3-phenylpropyl)amino]pentyl]-amino]-1H-carbazol-3-yl]carbonyl]-L-valyl-L-aspartamide (22).

Also especially preferred are compounds of general formula (I) in which $R^7$ is:
a phenylmethylcarboxamide radical that is substituted in the aromatic system, in particular the compounds (3R)-N-[(1S)-1 -(aminocarbonyl)-2-methylpropyl]-2,3,4,9-tetrahydro-3-[[(4-methylphenyl)acetyl]amino]-1H-carbazole-3-carboxamide (165a),
N-[(1S)-1-(aminocarbonyl)-2-methylpropyl]2,3,4,9-tetrahydro-3-[[(4-methoxyphenyl)-acetyl]amino]-1H-carbazole-3-carboxamide (175),
(3R)-N-[(1S)-1-(aminocarbonyl)-2-methylpropyl]-3-[[(3-bromophenyl)acetyl]amino]-2,3,4,9-tetrahydro-1H-carbazole-3-carboxamide (96),
(3R)-N-[(1S)-1-aminocarbonyl)-2-methylpropyl]-3-[[(4-fluorophenyl)acetyl]amino]-2,3,4,9-tetrahydro-1H-carbazole-3-carboxamide (91),
(3R)-N-[(1S)-1-(aminocarbonyl)-2-methylpropyl]-3-[[(4-chlorophenyl)acetyl]amino]-2,3,4,9-tetrahydro-1H-carbazole-3-carboxamide (167a);
a phenylhexylamine radical, in particular the compound (3R)-N-[(1S)-1-(aminocarbonyl)-2-methylpropyl]-2,3,4,9-tetrahydro-3-[(6-phenylhexyl)amino]-1H-carbazole-3-carboxamide (234a);
or a phenylpropyl radical, in particular the compounds 6,8-dichloro-2,3,4,9-tetrahydro-3-(3-phenylpropyl)-1H-carbazole-3-carboxylic acid (275) and
ethyl-6,8-dichloro-2,3,4,9-tetrahydro-3-(3-phenylpropyl)-1H-carbazole-3-carboxylate (272).

Preferred are also any new compounds of general formula (I) according to the invention that are present in R-configuration in the carbon atom that is substituted by radicals $R^6$ and $R^7$, if radicals $R^6$ and $R^7$ together form an alpha-aminocarboxylic acid structural element.

Most preferred for the purposes of this invention are the compounds phenylmethyl [(1S,2S)-1-[[[(3R)-3-[[[(1S)-1-(aminocarbonyl)-2-methylpropyl]amino]carbonyl]-6,8-dichloro-2,3,4,9-tetrahydro-1H-carbazol-3-yl]amino]carbonyl]-2-methylbutyl]carbamate (184a), phenylmethyl [(1S,2S)-1-[[[(3R)-3-[[[(1S)-1-(hydroxymethyl)-2-methylpropyl]amino]carbonyl]-2,3,4,9-tetrahydro-1H-carbazol-3-yl]amino]carbonyl]-2-methylbutyl]carbamate (267a), (2S)-1-[[(3R)-3-[[(4-chlorophenyl)acetyl]amino]-2,3,4,9-tetrahydro-8-methoxy-1H-carbazol-3'-yl]carbonyl]-2-pyrrolidine carboxamide (189a) and 6,8-dichloro-2,3,4,9-tetrahydro-3-(3-phenylpropyl)-N-(2-pyridinylmethyl)-1H-carbazole-3-methanamine (283).

Other representatives of new compounds of general formula (I) according to the invention including their production are indicated in the examples.

The new tetrahydrocarbazole derivatives (I) according to the invention, as defined above, are ligands of GPCR and can be used in particular for inhibition, i.e., as antagonists of the gonadotropin-releasing hormone, for example for male birth control, for hormone therapy, for treatment of female subfertility or infertility, for female contraception and to combat tumors.

In male birth control, the compounds according to the invention bring about a reduction in spermatogenesis. A combined administration with androgens, e.g., testosterone or testosterone derivatives, such as, for example, testosterone esters, preferably takes place. In this case, the administration of testosterone derivatives can be carried out by, for example, injection, e.g., by intramuscular depot injection.

Compounds (1) according to the invention, optionally in combination with other hormones, e.g., estrogens and/or progestins, can also be used in hormone therapy, for example for treating endometriosis, uterus leiomyomas and uterine fibroids. Especially preferred are combinations of the GnRH antagonists according to the invention and tissue-selective partial estrogen agonists such as Raloxifene®. In addition, the compounds according to the invention can be used in hormone replacement therapy. Moreover, compounds (1) according to the invention can be used for increasing female fertility, for example by inducing ovulation, and treating sterility.

In contrast, new compounds (1) according to the invention are also suitable for contraception in females. Thus, the GnRH antagonist according to the invention can be administered on days 1 to 15 of the cycle together with estrogen, preferably with very low estrogen dosages. On days 16 to 21 of the intake cycle, progestagen is added to the estrogen-GnRH-antagonist combination. The GnRH antagonist according to the invention can be administered continuously over the entire cycle time. In this way, a reduction in the hormone dosages and thus a reduction in the side effects of unphysiological hormone levels can be achieved. In addition, advantageous effects in women who suffer from polycystic ovarian syndrome and androgen-dependent diseases, such as acne, seborrhea and hirsutism, can be achieved. An improved cycle monitoring relative to previous administration methods can also be expected. Further indications are benign prostate hyperplasia, gonad protection in chemotherapy, controlled ovarian stimulation/artificial reproduction techniques, infantile development disorders, e.g., Pubertas praecox and polycystic ovaries.

Finally, compounds (I) according to the invention, as defined above, can also be used for the treatment of hormone-dependent tumor diseases, such as premenopausal breast cancer, prostate cancer, ovarian cancer and endometrial cancer, by the endogenous sex steroid hormones being suppressed.

New compounds (1) according to the invention, as defined above, are suitable as GPCR ligands, in particular GnRH antagonists for treating the above-indicated pathologic conditions for administration to mammals, in particular to humans, but also for the purposes of veterinary medicine, e.g., in the case of domestic and working animals but also in the case of wild animals.

The administration can be carried out in the known way, for example, orally or non-orally, in particular topically, rectally, intravaginally, nasally or by injections or implantation. Oral administration is preferred. New compounds (I) according to the invention are brought into a form that can be administered and are optionally mixed with pharmaceutically compatible vehicles or diluents. Suitable adjuvants and vehicles are described in, for example, *Ullmann's Encyclopedia of Technical Chemistry*, Vol. 4, (1953), 1–39; *Journal of Pharmaceutical Sciences*, Vol. 52 (1963), 918 ff; issued by Czetsch-Lindenwald, "*Hilfsstoffe für Pharmazie* und angrenzende Gebiete [Adjuvants for Pharmaceutics and Related Fields]"; Pharm. Ind. 2, 1961, 72 ff; Dr. H. P. Fiedler, "Lexikon der Hilfsstoffe für Pharmazie, Kosmetik und angrenzende Gebiete [Dictionary of Adjuvants for Pharmaceutics, Cosmetics and Related Fields]," Cantor, K. G., Aulendorf in Württemberg, 1971.

Oral administration can be carried out, for example, in solid form as tablets, capsules, gel capsules, coated tablets, granulates or powders, but also in the form of a drinkable solution. For oral administration, the new compounds of general formula (I) according to the invention, as defined above, can be combined with known and commonly used physiologically compatible adjuvants and vehicles, such as, e.g., gum arabic, talc, starch, sugar, such as, e.g., mannitol, methyl cellulose, lactose, gelatin, surfactants, magnesium stearate, cyclodextrins, aqueous or non-aqueous vehicles, diluents, dispersing agents, emulsifiers, lubricants, preservatives and flavoring substances (e.g., ethereal oils). The compounds according to the invention can also be dispersed in a microparticulate, e.g., nanoparticulate composition.

The non-oral administration can be carried out by, for example, intravenous, subcutaneous or intramuscular injection of sterile aqueous or oily solutions, suspensions or emulsions, by implants or by ointments, creams or suppositories. An administration as a timed-release form can optionally also be carried out. Implants can contain inert materials, e.g., biodegradable polymers or synthetic silicones, such as, e.g., silicone rubber. Intravaginal administration can be carried out by, e.g., vaginal rings. Intrauterine administration can be carried out by, e.g., diaphragms, etc. Moreover, a transdermal administration, in particular by a formulation suitable in this respect and/or suitable means such as, e.g., a patch, is also provided.

As already mentioned above, new compounds (I) according to the invention can also be combined with other pharmaceutical active ingredients. Within the scope of a combination therapy, the individual active components can be administered simultaneously or separately, specifically either on the same path (e.g., orally) or on separate paths (e.g., orally and as an injection). They can be present or administered in a unit dose in the same or different amounts. A specific dosage regimen can also be used if this seems suitable. In this way, several of the new compounds (I) according to the invention can also be combined with one another.

The dosage can vary within a wide range depending on the type of indication, the severity of the disease, the type of administration, the age, sex, body weight and sensitivity of the subject that is to be treated. This corresponds to the abilities of one skilled in the art to determine a "pharmacologically effective amount" of the combined pharmaceutical composition. Unit dosages of 1 µg to 100 mg, especially preferably 1 µg to 10 mg, and most preferably 1 µg to 1 mg per kg of body weight of the subject that is to be treated are preferred. The administration can be carried out in an individual dose or several separate dosages.

Accordingly, in another aspect of this invention, pharmaceutical compositions, as described above, that comprise at least one of new compounds (I) according to the invention, as defined above, as well as optionally pharmaceutically compatible vehicles and/or adjuvants, are also included by this invention. Preferred and especially preferred pharmaceutical compositions are any that comprise at least one of the above-mentioned preferred or especially preferred new compounds (I) according to the invention, in particular the above compounds that are mentioned by name. In pharmaceutical compositions according to this invention, in addition to at least one compound of general formula (I), as defined above, still other pharmaceutical active ingredients can also be present, as already presented above in more detail.

In the pharmaceutical compositions according to the invention, at least one of new compounds (I) according to the invention, as defined above, is present in one of the above-mentioned preferred, especially preferred or most preferred unit doses, specifically preferably in a form of administration that makes oral administration possible.

Moreover, in another aspect, this invention provides compounds of general formula (I), as defined above, for use as pharmaceutical agents.

Tetrahydrocarbazole compounds of general formula (I) that are preferred according to the invention, as defined above, for use as pharmaceutical agents are in turn any compounds that were mentioned above as preferred and especially preferred compounds, in particular the preferred compounds according to the invention that are mentioned by name as well as the compounds that are mentioned in the examples.

Relative to compounds (I) according to the invention that comprise pharmaceutical compositions as well as relative to compounds (I) according to the invention for use as pharmaceutical agents, reference is made to the remarks regarding the new compounds (I) according to the invention, as defined above, regarding possible uses and means of administration.

In another aspect, this invention also provides the use of at least one tetrahydrocarbazole derivative of general formula (I) according to the invention, as defined above, whereby—as initially defined—the tetrahydrocarbazoles that are disclosed in the publications by Millet et al. and Maki et al. are excluded from the meaning of general formula (I), for the production of a pharmaceutical agent for treating GPCR-mediated diseases, especially for inhibiting the gonadotropin-releasing hormone (GnRH).

Moreover, in another aspect, this invention provides the use of at least one compound of general formula (I) according to the invention, as defined above, but including the compounds excluded by name above, from the publications by Millet et al. and Maki et al., namely 3-amino-1,2,3,4-tetrahydrocarbazole-3-carboxylic acid, 3-amino-6-methoxy-1,2,3,4-tetrahydrocarbazole-3-carboxylic acid, 3-amino-6-benzyloxy-1,2,3,4-tetrahydro-carbazole-3-carboxylic acid, 3-acetamido-1,2,3,4-tetrahydrocarbazole-3-carboxylic acid, methyl-3-acetamido-1,2,3,4-tetrahydrocarbazole-3-carboxylate, (−)-menthyl-3-acetamido-1,2,3,4-tetrahydrocarbazole-3-carboxylate and 3-tert-butoxycarbonyl-amino-1,2,3,4-tetrahydrocabazole-3-carboxylic acid, for the production of a pharmaceutical agent for inhibiting the GnRH, preferably for male birth control, for hormone therapy, for treating female subfertility and infertility, for female contraception and to combat tumors. Stated more clearly, the designation "a compound of general formula (I) as defined above, but including the compounds excluded by name above" means a compound of general formula (I)

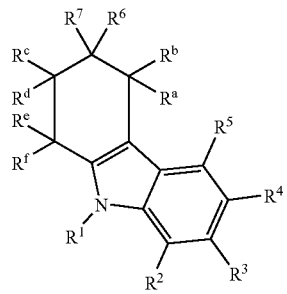

(I)

in which:

radical $R^1$ is a hydrogen atom, a $C_2$–$C_6$ alkenyl radical or a $C_1$–$C_6$ alkyl radical and optionally can be substituted with an aryl radical, a hetaryl radical or the group —COOR$^{11}$, whereby the aryl radical or hetaryl radical can be substituted with up to three substituents, which are selected, independently of one another, from the group that consists of —NO$_2$, —CH$_3$, —CF$_3$, —OCH$_3$, —OCF$_3$ and halogen atoms, and radical $R^{11}$ is a hydrogen atom, a $C_1$–$C_{12}$ alkyl radical, a $C_1$–$C_{12}$ aralkyl radical, an aryl radical, a hetaryl radical or the group —COCH$_3$, and optionally can be substituted with a substituent that is selected from the group that consists of —CONH$_2$, —COCH$_3$, —COOCH$_3$, —SO$_2$CH$_3$ and aryl radicals;

radicals $R^2$, $R^3$, $R^4$ and $R^5$, independently of one another, in each case are a hydrogen atom, a halogen atom, the group —COOH, —CONH$_2$, —CF$_3$, —OCF$_3$, —NO$_2$, —CN, a $C_1$–$C_6$ alkyl radical, a $C_1$–$C_6$ alkenyl radical, a $C_1$–$C_6$ alkoxy radical, a $C_1$–$C_{12}$ aralkyl radical, an aryl radical or a hetaryl radical;

radical $R^6$ is the group —CONR$^8$R$^9$, —COOR$^8$, —CH$_2$NR$^8$R$^9$, —CH$_2$R$^8$, —CH$_2$OR$^8$ or a $C_1$–$C_{12}$ alkenyl radical, which optionally is substituted with radicals $R^8$ and $R^9$, whereby radicals $R^8$ and $R^9$, independently of one another, in each case are a hydrogen atom, a $C_1$–$C_{12}$ alkyl radical, a $C_1$–$C_{12}$ aralkyl radical, a $C_1$–$C_{12}$ hetaralkyl radical, an aryl radical or hetaryl radical, which can be substituted with one or more substituents, which are selected from the group that consists of —OH, —NH$_2$, —CONHR$^{10}$, —COOR$^{10}$, —NH—C(—NH)—NH$_2$ and halogen atoms, whereby radical $R^{10}$ is a hydrogen atom, a $C_1$–$C_{12}$ alkyl radical, a $C_1$–$C_{12}$ aralkyl radical, an aryl or hetaryl radical and optionally is substituted with the group —CON(R$^{11}$)$_2$, or whereby radicals $R^8$ and $R^9$ together can form a ring structure that either exclusively consists of carbon atoms or, mixed, consists of carbon and heteroatoms;

radical $R^7$ is a hydrogen atom, a $C_1$–$C_{12}$ alkyl radical, a $C_1$–$C_{12}$ alkenyl radical, a $C_1$–$C_{12}$ aralkyl radical, an aryl radical or hetaryl radical, the group —NR$^2$R$^{13}$, —NH-COR$^{14}$, —NHCONHR$^4$, —NHCOOR$^4$ or —NHSO$_2$R$^4$, and optionally can be substituted with one or more substituents that are selected from the group that consists of —OH, —NH$_2$, —CONH$_2$, —COOH and halogen atoms, radicals $R^{12}$ and $R^{13}$, independently of one another, in each case are a hydrogen atom, a $C_2$–$C_6$ alkenyl radical or a $C_1$–$C_{12}$ alkyl radical, and optionally can be substituted with one or more aryl radicals or hetaryl radicals, which can be substituted in turn with up to three substituents, which are selected, independently of one another, from the group that consists of —NO$_2$, —CH$_3$, —CF$_3$, —OCH$_3$, —OCF$_3$ and halogen atoms, and radical $R^{14}$ is a hydrogen atom, a $C_1$–$C_{12}$ alkyl radical, a $C_1$–$C_{12}$ alkenyl radical, a $C_1$–$C_{12}$ aralkyl radical, an aryl radical or a hetaryl radical, which optionally can be substituted with one or more substituents, which are selected from the group that consists of —NO$_2$, —CH$_3$, —OR$^{11}$, —CF$_3$, —OCF$_3$, —OH, —N(R$^{11}$)$_2$, —OCOR$^{11}$, —COOH, —CONH$_2$, —NHCONHR$^{11}$, —NHCOOR$^{11}$, and halogen atoms;

and radicals $R^a$, $R^b$, $R^c$, $R^d$, $R^e$ and $R^f$, independently of one another, in each case are a hydrogen atom, a halogen atom, the group —COOH, —CONH$_2$, —CF$_3$, —OCF$_3$, —NO$_2$, —CN, a $C_1$–$C_6$ alkyl radical, $C_1$–$C_6$ alkoxy radical, an aryl radical or a hetaryl radical.

The indications already mentioned in connection with the new compounds of general formula (I) according to the invention, as defined above (i.e., excluding the compounds mentioned by name above and disclosed in the publications by Maki et al. and Millet et al.) were already provided above in reference to the new compounds (I) according to the invention. The preferred and especially preferred compounds in the use of the above-defined compounds for the production of a pharmaceutical agent for inhibiting the GnRH are identical to the preferred and especially preferred compounds already mentioned above in connection with the new compounds of general formula (I) according to the invention, as defined above.

In another aspect, this invention provides the use of a compound (I) according to the invention as defined above, but also including compounds initially excluded by name for male birth control or for female contraception. Preferred and especially preferred compounds according to the invention for this use are any compounds that were already initially mentioned as preferred or especially preferred compounds of general formula (I) according to the invention, as defined above.

Moreover, this invention provides a process for male birth control or for female contraception that comprises the administration of an amount of a compound according to the invention that is effective for male birth control or for female contraception as defined in the paragraph directly above, to a subject, preferably a mammal, especially preferably a human.

In another aspect, this invention relates to a process for treating GPCR-mediated pathologic conditions. The process comprises the administration of at least one compound (I) according to the invention, as defined above, to a mammal, especially a human, in whom such a treatment is necessary. The administration is usually carried out in a pharmaceutically effective amount. As already explained above in reference to the new compounds (I) according to the invention as well as the pharmaceutical compositions according to the invention, one skilled in the art must rely on his technical knowledge to determine a pharmaceutically effective amount based on the special requirements of the individual case. Compounds (I) according to the invention, however, are preferably administered in a unit dose of 1 µg to 100 mg, especially preferably 1 µg to 10 mg and most preferably 1 µg to 1 mg per body weight to the subject under treatment. The preferred form of administration is oral administration. It is also provided to administer one or more of compounds (I) according to the invention in combination with at least one other active ingredient, as already explained above.

Moreover, this invention also relates to a process for inhibiting GnRH in a patient, comprising the administration of a pharmaceutically effective amount of a compound of general formula (I), as defined above, but including the compounds excluded by name above to a patient who requires such a treatment. The process is preferably used in male birth control, hormone therapy, female contraception, treatment of female subfertility or infertility and to combat tumors.

Finally, in a last aspect, this invention also provides a process for the production of new tetrahydrocarbazole derivatives of general formula (I) according to the invention. The process for the production of the compounds of general formula (I) according to the invention can be performed in a different way, thus, e.g., in liquid phase or as partial or complete solid-phase synthesis. The selection of suitable synthesis conditions for the production of individual representatives of the compounds of general formula (I) can be made by one skilled in the art based on his general technical knowledge. Below, a process for the production of compounds of general formula (I) according to the invention is first described in general terms. Then, a specific variant of the process, namely a solid-phase process, is described. For further illustration of this invention, numerous representatives of the compounds of general formula (I) are found in the listed examples.

A process for the production of the compounds of general formula (I) according to the invention is preferably performed as follows:

The central tetrahydrocarbazole skeleton is accessible by a Fischer-indole synthesis that is known in the art. To this end, a suitably substituted cyclohexanone derivative that is optionally provided with protective groups is condensed with the phenylhydrazine derivative that is desired in each case, also suitably substituted and optionally provided with protective groups (e.g., according to Britten & Lockwood, *J. C. S. Perkin I* 1974, 1824 or according to Maki et al., *Chem. Pharm. Bull.* 1973, 21, 240). In particular, the cyclohexanone skeleton is substituted in positions 3,3', 5,5' and 6,6' by radicals $R^a$ to $R^f$ as well as in positions 4,4' by the radicals or optionally by precursors of radicals $R^6$ and $R^7$. The phenylhydrazine skeleton is optionally substituted by radicals $R^2$ to $R^5$. Phenylhydrazine derivatives that are not commercially available can be produced by the process that is known to one skilled in the art. Position isomers that are optionally produced upon the condensation of the cyclohexanone derivative and the phenylhydrazine derivative can be separated by chromatographic methods, such as, e.g., HPLC.

After the synthesis of the central tetrahydrocarbazole skeleton, radical $R^1$ can be introduced by N-alkylation of the nitrogen atom in 9-position with corresponding $R^1$-halides with use of a base (e.g., according to Pecca & Albonico, *J. Med. Chem.* 1977, 20, 487 or also according to Mooradian et al., *J. Med. Chem.* 1970, 13, 327).

Radicals $R^6$ and $R^7$, as was already indicated above, are introduced in a different way depending on their type, which is explained in more detail below.

In these radicals, α-aminocarboxylic acid structures are accessible by treatment of ketones with $NH_4(CO)_3$ and KCN under Schotten-Baumann conditions that are known in the art and subsequent alkaline hydrolysis of the formed hydantoin (Britten & Lockwood, *J. C. S. Perkin I* 1974, 1824).

Amide radicals are preferably produced with the process from peptide chemistry that is known in the art. To this end, the acid component is activated with an activating reagent such as DCC or else HATU (*Tetrahedron Lett.* 1994, 35, 2279) and is condensed in the presence of a base such as DIPEA and/or DMAP with the amino component.

Ester radicals can be obtained according to analogous conditions with use of the desired alcohols. The solvent that is used in this case is preferably anhydrous.

Secondary or tertiary amine radicals are obtained from primary amines either by nucleophilic substitution of alkyl halides or by reductive amination of aldehydes/ketones (e.g., *J. Org. Chem.* 1996, 61, 3849 or *Synth. Comm.* 1994, 609).

Sulfonamide radicals are obtained from the corresponding amines by reaction with sulfonic acid chlorides.

Urea radicals are obtained if the amines are reacted with corresponding isocyanates.

Urethane radicals can be produced by corresponding alcohols being preactivated with carbonyldihydroxy benzotriazole $((HOBt)_2CO)$ and then reacted with amines (Warass et al., *LIPS* 1998, 5, 125).

Alcohols are accessible from carboxylic acid esters by reduction with $LiAlH_4$.

Aldehyde radicals are obtained from alcohol precursors by being oxidized with DMSO/oxalyl chloride, for example, under Swern conditions that are known in the art (Pansavath et al., *Synthesis* 1998, 436).

Substituted amine radicals are obtained by reductive amination of amines with aldehydes (*J. Org. Chem.* 1996, 61, 3849).

Ether radicals can be obtained by the alcohol precursors with a base such as NaH being deprotonated under Williams conditions that are known in the art and then reacted with an alkyl halide.

Double bonds in the radicals can be introduced by an aldehyde or ketone precursor being reacted according to Wittig conditions that are known in the art with corresponding phosphonylides.

A solid-phase process for the production of the compounds of formula (I) according to the invention preferably comprises steps (a) to (d) that are explained in more detail below:

Step (a) essentially proceeds analogously to a Fischer-indole synthesis, e.g., according to Britten & Lockwood, *J. C. S. Perkin I* 1974, 1824; Maki et al., *Chem. Pharm. Bull.* 1973, 21, 240 or Hutchins & Chapman, *Tetrahedron Lett.* 1996, 37, 4869 and comprises the condensation of a cyclohexanone derivative (II) that contains group G and that is anchored to a solid phase SP via a linker L that is suitable for forming radical $R^6$

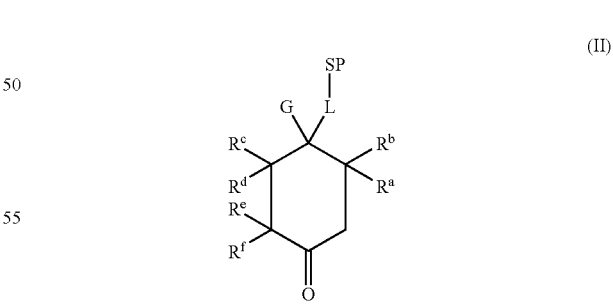

(II)

whereby in the event that radical $R^7$ is a hydrogen atom, a $C_1$–$C_{12}$ alkyl radical, a $C_1$–$C_{12}$ aralkyl radical or a hetaryl radical, group G is equal to radical $R^7$, and in the event that radical $R^7$ has a different meaning than is indicated in formula (I) for $R^7$, group G is equal to a group —NH-Pg, whereby Pg stands for a protective group with a phenylhydrazine derivative (III) that is substituted by $R^2$ to $R^5$

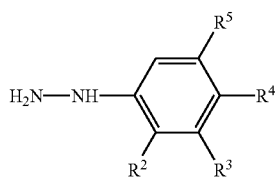 (III)

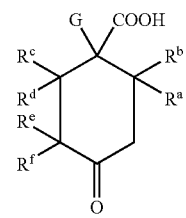 (II')

in the presence of an acid, preferably acetic acid, and a metal salt; preferably ZnCl$_2$. As a solvent, DMF is preferred. Radicals R$^a$ to R$^f$ are defined as indicated above in formula (I). Certain substituents or groups can optionally also be present in protected form, whereby the protective groups are removed at a suitable time in the course of the process again according to a process that is known in the art.

For the purpose of this invention, especially Rink amide resins (Rink, *Tetrahedron Lett.* 1989, 28, 3787), HMB resins (Sheppard et al., *Int. J. Peptide Protein Res.* 1982, 20, 451), Wang resins (Lu et al., *J. Org. Chem.* 1981, 46, 3433) or chlorotrityl resins (Barlos et al., *Int. J. Peptide Protein Res.* 1991, 38, 562) are suitable as solid phase SP, if the cyclohexanone derivative (II) is to be anchored by means of an (amino-)carboxylic acid to solid phase SP. To anchor the alcohol precursors of the cyclohexanone derivative (II), the DHP linker (Liu & Elman, *J. Org. Chem.* 1995, 60, 7712) can be used. Aromatic compound precursors of the cyclohexanone derivative (II) can be anchored in a "traceless" manner to triazine resins (Bräse et al., *Angew. Chem. Int. Ed.* 1998, 37, 3413).

Protective group Pg that is optionally included in group G and that protects an α-amino group —NH$_2$ is preferably an "Fmoc" (9-fluorenylmethoxycarbonyl) protective group, but can also be another commonly used amino protective group, e.g., from the series of alkoxycarbonyl protective groups (such as, e.g., the "Z" (benzyloxycarbonyl) group or the "Boc" (tert-butoxycarbonyl) group) or another suitable protective group, e.g., a "trityl" (triphenylmethyl) protective group.

Linker L is constituted in such a way that after corresponding derivatization (steps (b) and (c)) and working-up (step (d)) in the end product, the desired radical R with one of the meanings that is indicated above for R$^6$ results in the tetrahydrocarbazole derivative of general formula (I). To illustrate the composition of linker L, the latter can then be explained by way of example in the event that R$^6$ is equal to group —CONR$^8$R$^9$.

In the event that in the product of formula (I) according to the invention radical R$^6$ has the meaning —CONR$^8$R$^9$, a compound Pg-N(R$^8$)—R$^{9'}$—COOH that forms linker L is first anchored by means of an activating reagent, such as DCC (dicyclohexyl-carbodiimide) or HATU (0-(7-azabenzotriazol-1-yl)-N,N—N',N'-tetramethyluronium hexafluorophosphate) to solid phase SP via free amino groups of SP, whereby Pg and SP have the meaning indicated above and R$^{9'}$ forms a portion of subsequent radical R$^9$. Protective group Pg is then cleaved off, e.g., in the case of an Fmoc protective group by means of piperidine/DMF. From this results a compound HR$^8$N—R$^{9'}$—CONH—SP. The latter compound is now reacted with a precursor of cyclohexanone derivative (II), namely the cyclohexanone-carboxylic acid (II')

in turn with use of an activating reagent such as DCC or HATU, from which finally the cyclohexanone derivative (II), as defined above, results. Linker L has the meaning —CONR$^8$—R$^{9'}$—CONH—SP for the above-described case. Isomers of any type (enantiomers, diastereomers or position isomers) that are optionally produced can be separated—as well as at other sites of the described production process—in a known-way by means of HPLC.

Then, actual step (a), i.e., the condensation of cyclohexanone derivative (II), is carried out with substituted phenylhydrazine derivative (III) and optionally cleavage of protective group Pg in group G by means of, e.g., piperidine (in the case of an Fmoc protective group), so that a free α-amino group is produced again at this point.

In the event that radical R$^7$ is the group —NHCOR$^{14}$, —NHSO$_2$R$^{14}$, —NR$^{12}$R$^{13}$ (whereby R$^{12}$ and R$^{13}$ are not simultaneously hydrogen atoms), —NHCONHR$^{14}$ or —NCOOR$^{14}$, a derivatization of the now unprotected α-amino group of resin-bonded cyclohexanone derivative (II) finally takes place in step (b), such that the various alternative radicals R$^7$, defined above, can be formed.

Depending on the type of desired radical R$^7$ in the tetrahydrocarbazole end product (I) according to the invention, in this case the procedure is as follows:

In the event that R$^7$ is the group —NHCOR$^{14}$, the reaction product from step (a) is reacted with a carboxylic acid R$^{14}$COOH in the presence of an activating reagent, such as, e.g., DCC or HATU, and in the presence of a base, such as, e.g., DIPEA (diisopropylethylamine) or DMAP (4-dimethylaminopyridine) according to known processes for forming peptide bonds (cf., e.g., *Tetrahedron Lett.* 1994, 35, 2279; Alternative (i)).

In the event that R$^7$ is a sulfonamide group —NHSO$_2$R$^{14}$, the reaction product from step (a) is reacted with a sulfonic acid derivative R$^{14}$SO$_2$X, whereby X is a leaving group, preferably a halogen atom, especially a chlorine atom, in the presence of a base, such as, e.g., DMAP or DIPEA (cf., e.g., Gennari et al., *EJOC* 1998, 2437; Alternative (ii)).

In the event that R$^7$ is the group —NR$^{12}$R$^3$ (whereby R$^{12}$ and R$^{13}$ are not simultaneously hydrogen atoms), and in the event that radical R$^{12}$ is a hydrogen atom, the reaction product from step (a) is reacted with a reagent R$^{13}$X, whereby X is a leaving group, such as, e.g., a halide atom, especially a chloride atom, in the presence of a base, such as, e.g., DBU or DIPEA (cf. Green, *JOC* 1995, 60, 4287 or *JOC* 1996, 61, 3849) or with an aldehyde R$^{13}$CHO in the presence of a reducing agent, such as, e.g., NaH/B(OAc)$_3$. In the event that none of radicals R$^{12}$ and R$^{13}$ are a hydrogen atom, the reaction product from step (a) is reacted with a ketone R$^{12}$COR$^{13}$ in the presence of a reducing agent (cf. Ellmann et al., *JOC* 1997, 62, 1240 or *Synth. Commun.* 1994, 609; Alternative (iii)). In the event that in R$^7$ equal to —NR$^{12}$R$^{13}$, both radicals R$^{12}$ and R$^{13}$ are hydrogen atoms, alternative (vi) below applies.

In the event that $R^7$ is the group —NHCONHR$^{14}$ (a urea derivative), the reaction product from step (a) is reacted with an isocyanate R$^{14}$NCO (cf. Brown et al., *JACS* 1997, 119, 3288; Alternative (iv)).

In the event that $R^7$ is a carbamate or urethane group —NHCOOR$^{14}$, the reaction product from step (a) is reacted by alcohol HOR$^{14}$ that is preactivated by carbonyldihydroxybenzotriazole ((HOBt)$_2$CO) (cf. Warass et al., *LIPS* 1998, 5, 125; Alternative (v)).

In the event that $R^7$ is a hydrogen atom, a $C_1$–$C_{12}$ alkyl radical, a $C_1$–$C_{12}$ aralkyl radical, an aryl radical, a hetaryl radical or the group —NH$_2$ (i.e., in $R^7$ equal to —NR$^{12}$R$^{13}$, both radicals R$^{12}$ and R$^{13}$ are hydrogen atoms), step (b) is eliminated, since no further derivatization is necessary (alternative (vi)).

Analogously to step (b) that is explained above, step (c), i.e., the derivatization on the indole-nitrogen atom, also corresponds to various alternatives that are explained in more detail below:

For cases (i) to (v) that are defined above in step (b), a deprotonation of the reaction product that is obtained in (b) takes place by means of a base, such as, e.g., NaH or NaHMD, and a subsequent derivatization by means of a group R$^1$X, whereby X is a leaving group, e.g., a halide atom, in particular a chloride atom (cf. Collini & Ellingboe, *Tetrahedron Lett.* 1997, 38, 7963; Pecca & Albonico, *J. Med. Chem.* 1977, 20, 487 or Mooradian et al., *J. Med. Chem.* 1970, 13, 327).

For case (vi) that is defined above in step (b), i.e., if step (b) is omitted, a deprotonation of the reaction that is obtained in (a) takes places analogously to the descriptions above by means of a base, such as, e.g., NaH or NaHMDS and a subsequent derivatization by means of a group R$^1$X, whereby X is a leaving group, e.g., a halide atom, in particular a chloride atom.

Finally, step (d) essentially comprises the cleavage of the reaction product that is obtained in (c) from solid phase SP. In the case of Wang, trityl, DHP and Rink amide resin, the cleavage of the reaction product that is obtained in (c) takes place with the aid of an acid, especially with TFA (trifluoroacetic acid). In the case of an aminolytic cleavage of an HMB resin, for example, ammonia in methanol is used as a cleavage reagent. Then, the desired product is isolated in the usual way.

Embodiments for the production of tetrahydrocarbazole derivatives according to the invention are cited below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

I. General Synthesis Instructions for Compounds According to the Invention

A. Coupling of Carboxylic Acids to the Rink Amide Resin:

0.1 mmol of Fmoc-protected Rink amide resin (166 mg, concentration 0.6 mmol/g) is presteeped in a vessel with a fritted bottom with 1.5 ml of DMF for 20 minutes. After being suctioned off, 1.5 ml of 20% piperidine/DMF is added, and it is stirred for 5 minutes. After being suctioned off, 1.5 ml of 20% piperidine/DMF is added again and stirred for 15 minutes. After being suctioned off, it is washed four times with DMF. Then, 675 µl of a 0.267 M solution of Fmoc-protected amino-carboxylic acid in DMF, 675 µl of HATU solution (0.267 M in DMF) and 150 µl of NMM solution (2.4 M in DMF) as well as 0.01 mmol of DMAP are added and stirred for 4 hours at 40° C. After being suctioned off, the same reagents are added again and stirred for 4 hours at 40° C. Then, it is suctioned off and washed four times with DMF.

B. Coupling of Carboxylic Acids to the Trityl Resin:

2.98 mmol of Fmoc-protected amino-carboxylic acid is dissolved in 30 ml of dry dichloromethane, mixed with 14.3 mmol (2.45 ml) of DIPEA and added to 2.98 mmol of 2-chlorotrityl chloride resin (2 g, concentration 1.49 mmol/g of resin). After two hours of shaking, the resin is suctioned off via a frit and washed three times with 20 ml of dichloromethane/MeOH/DIPEA 17:2:1. Then, it is washed three times with 20 ml of dichloromethane, three times with methanol and three times with 20 ml of ether and dried in a vacuum. A resin with a concentration of 0.5 to 1 mmol of amino-carboxylic acid per g of resin is obtained.

C. Coupling of Carboxylic Acids to the HMB Resin:

21.3 mmol of amino-carboxylic acid and 21.3 mmol of HATU are dissolved in 60 ml of DMF and mixed with 63.9 mmol (10.9 ml) of DIPEA. After 5 minutes, 5 g of polystyrene-HMB resin (concentration 0.71 mmol/g of resin) is added and shaken for 5 minutes at room temperature. Then, 21.3 mmol (2.6 g) of DMAP is added and shaken for 1 hour at room temperature. Then, the resin is suctioned off and washed once each with 100 ml of DMF, DCM and DMF. The resin is mixed with 100 ml of 10% Ac$_2$O (acetic anhydride)/DMF/5% DMAP and shaken for 15 minutes. After being suctioned off, it is washed three times each with 100 ml of DCM and ether and dried in a vacuum.

D. Coupling of Carboxylic Acids to the Wang Resin:

54.6 mmol of carboxylic acid and 27.3 mmol (4.2 ml) of DIC are dissolved in 500 ml of dry DCM and stirred for 10 minutes at room temperature. After the precipitated urea is filtered out, the solution is evaporated to the dry state, and the residue is dissolved in 160 ml of dry DMF. The solution is added to 4.55 mmol (5 g, concentration 0.91 mmol/g of resin) of Wang resin that is presteeped in DMF and mixed with 4.55 mmol (556 mg) of DMAP. After 1.5 hours of shaking at room temperature, the resin is suctioned off and taken up in 100 ml of 10% Ac$_2$O/DMF/5% DMAP and shaken for 15 minutes. After being suctioned off, it is washed three times each with 100 ml of DCM and ether and dried in a vacuum.

E. Coupling of an Alcohol to the DHP Resin:

0.5 mmol of DHP resin (0.5 g, concentration density of 1 mmol/g) is presteeped for 15 minutes in 2 ml of dichloroethane. 2 ml of a solution of 0.75 M alcohol/0.37 M pyridinium paratoluenesulfonate is added thereto and stirred for 16 hours at 80° C. After cooling to room temperature, 5 ml of pyridine is added, shaken briefly and suctioned off. It is washed twice each with 5 ml of DMF, DCM and hexane.

F. Protection Removal of a Resin-Bonded Fmoc Protective Group:

1.5 ml of 20% piperidine/DMF is added to 0.1 mmol of a resin-bonded Fmoc group and stirred for 5 minutes. After being suctioned off, 1.5 ml of 20% piperidine/DMF is added again, and it is stirred for 15 minutes. After suctioning off, it is washed four times with DMF.

G. Coupling of a Carboxylic Acid to Resin-Bonded Amino Functions:

675 µl of a 0.267 M solution of Fmoc-protected aminocarboxylic acid in DMF, 675 µl of HATU solution (0.267 M in DMF) and 150 µl of NMM solution (2.4 M in DMF) as well as 0.01 mmol of DMAP are added to 0.1 mmol of resin-bonded amino functions and stirred for 4 hours at 40° C. After being suctioned off, the same reagents are added again and stirred for 4 hours at 40° C. Then, it is suctioned off and washed four times with DMF.

H. Coupling of Acetic Acid to Resin-Bonded Amino Functions:

1.5 ml of a solution of 10% acetic anhydride in DMF is added to 0.1 mmol of resin-bonded amino functions and stirred for 15 minutes at room temperature. Then, it is suctioned off and washed four times with DMF.

I. Synthesis of Tetrahydrocarbazoles Starting from Resin-Bonded Cyclohexanones:

Before the reaction, 0.1 mmol of cyclohexanone resin is washed twice with 2 ml of DMF and twice with 2 ml of acetic acid. Then, 1 ml of DMF and 2 ml of 0.5 M hydrazine/0.5 M of $ZnCl_2$ in acetic acid are added to the resin and stirred for 20 hours at 70° C. Then, it is suctioned off and washed twice with 2 ml of acetic acid and 2 ml of DMF.

J. Synthesis of Sulfonamides Starting from Resin-Bonded Amides:

The resin is washed twice with 2 ml each of DMF and DCE. 1 ml of 0.5 M sulfonic acid chloride in DCE as well as 400 µl of 2.5 M NMM/1 equivalent of 0.25 M DMAP in DMF are added to 0.1 mmol of resin-bonded amine. After 12 hours of stirring at 60° C., it is suctioned off, and the coupling is repeated. After being suctioned off, it is washed four times with 2000 ml of DMF.

K. Synthesis of Ureas by Reaction of Resin-Bonded Amine with Isocyanates:

2 ml of 0.5 M isocyanate in DCM is added to 0.11 mmol of resin-bonded amine and stirred for 18 hours at room temperature. After being suctioned off, it is washed four more times with DMF.

L. Synthesis of Carbamates by Reaction of Resin-Bonded Amine with Preactivated Alcohols:

For preactivation, 0.4 M alcohol and 0.39 M dibenzotriazolyl carbonate and 0.39 M pyridine in DMF are stirred at 40° C. for 15 minutes. 1 mmol of resin-bonded amine is mixed with 1 ml of preactivated alcohol, and 167 ml of 2.4 M NMM in DMF is added. After 4 hours of stirring at 60° C., it is suctioned off and washed four times with DMF.

M. Synthesis of N-Alkylamines by N-Alkylation of Resin-Bonded Amines with Alkyl Halides and Catalytic KI:

1 ml of 0.5 M halide/0.05 M KI in DMF and 416 µl of 2.4 M DIPEA in DMF are added to 0.1 mmol of resin-bonded amine and stirred for 12 hours at 90° C. After being suctioned off, the resin is washed four times with 2 ml of DMF.

N. N-Alkylation of Resin-Bonded Indole Nitrogens with Halide/NaH in DMF:

1 ml of DMF and 0.5 mmol of NAH (55% suspension in oil) is added to 0.1 mmol of resin-bonded amine. After 30 minutes of stirring at room temperature, 1 ml of 0.5 M halide in DMF is added and stirred for 8 hours at 45° C. Then, it is suctioned off and washed twice each with 2 ml of methanol, DMF, methanol and DMF.

O. Cleavage of Wang, Trityl, DHP, and Rink Amide Resins:

2 ml of a 95% TFA/5% $H_2O$ solution is added to 0.1 mmol of resin and shaken for 3 hours at room temperature. Then, the resin is filtered off and rewashed with another 2 ml of TFA. The combined TFA solutions are evaporated to the dry state and yield the crude products.

P. Aminolytic Cleavage of HMB Resin:

2 ml of DMF and 2 ml of 7 M $NH_3$ in methanol are added to 0.1 mmol of resin and shaken for 18 hours at room temperature. Then, the resin is filtered off and rewashed with DMF. The combined solutions are evaporated to the dry state and yield the crude product.

Production of Required Starting Compounds:

3-[[(9H-Fluoren-9-ylmethoxy)carbonyl]amino]-2,3,4,9-tetrahydro-1H-carbazole-3-carboxylic Acid I 38.4 mmol (6.0 g) of 4,4-ethylenedioxycyclohexanone and 39.8 mmol (4.3 g) of phenylhydrazine are dissolved separately in 50 ml or 10 ml of water and then mixed. After 10 minutes of stirring, the resulting milky emulsion is extracted five times with ethyl acetate, dried with $MgSO_4$ and evaporated to the dry state. Yield: 9.2 g of orange oil.

9.2 g of unpurified phenylhydrazone is dissolved at room temperature in 240 ml of toluene and mixed with 4.9 g of $ZnCl_2$ that is freshly ground in a mortar. After 90 minutes of reflux in a water separator, most of the toluene is distilled off, mixed with an excess of 2N NaOH and extracted three times with ethyl acetate. The extract is washed with brine, dried with $MgSO_4$, and the solvent is distilled off. The remaining black oil is purified on silica gel with ethyl acetate/hexane 1:9. Yield: 2.7 g of beige solid.

11.6 mmol (2.7 g) of 1,2,4,9-tetrahydrospiro[3H-carbazole-3,2*-[1,3]doxolane] and 640 mg of p-toluenesulfonic acid are taken up in 70 ml of acetone and stirred for 2.5 hours at room temperature. The solution is added to $NaHCO_3$ solution, extracted with ethyl acetate, washed with brine, dried with $MgSO_4$ and concentrated by evaporation. 2.13 g of reddish-brown solid remains. After recrystallization from ether, 1.1 g of beige-colored solid is obtained.

60.2 mmol (11.1 g) of 1,2,4,9-tetrahydrospiro-3H-carbazol-3-one, 8.3 g of KCN, and 22.0 g of $(NH_4)_2CO_3$ are heated at 80° C. in 550 ml of 60% ethanol for 3 hours in an autoclave. After cooling to room temperature, the reaction mixture is added to ice water, and the precipitated solid is filtered off. Yield: 10.1 g of gray solid.

44.2 mmol (11.3 g) of 1,2,4,9-tetrahydrospiro[3H-carbazole-3,4'-imidazolidine]-2',5'-dione is heated to 150° C. with 62 g of $Ba(OH)_2 \times 8H_2O$ in 145 ml of $H_2O$ for 13 hours. After cooling to room temperature, the viscous mass is mixed with 37 g of $(NH_4)_2CO_3$ while being stirred and heated for 30 minutes to 100° C. After cooling to room temperature, it is filtered off, rewashed with water, and the filtrate is evaporated to the dry state. Yield: 7.7 g of beige solid.

26 mmol (5.8 g) of 3-amino-2,3,4,9-tetrahydro-1H-carbazole-3-carboxylic acid in 26 ml of 1N NaOH and 26 mmol (8.76 g) of Fmoc-ONSu in 28 ml of acetonitrile are combined at room temperature and diluted with 130 ml of acetonitrile/$H_2O$ 1:1. After two hours, the pH is readjusted to 9 (1.5 ml) with $NEt_3$ and stirred overnight at room temperature. Then, another 6.3 g (18.7 mmol) of Fmoc-ONSu, dissolved in 19 ml of acetonitrile, is added and stirred for another two hours while the pH is monitored. After distillative removal of the acetonitrile, it is acidified with 0.01 M HCl and extracted with ethyl acetate. The extract is washed neutral, dried with $Na_2SO_4$ and spun in until a dry state is reached. Recrystallization is carried out from ether/hexane. Yield: 10.7 g.

$^1$H-NMR (d$^6$-DMSO): δ=2.07 ppm (m, 1H); 2.50 (m, 1H); 2.70 (bs; 2H); 3.04 (q, 2H); 4.17 (m, 2H); 4.28 (m, 2H); 6.92 (tr, 2H); 6.99 (tr, 2H); 7.23 (tr, 2H); 7.24–7.35 (m, 3H); 7.38 (tr, 2H); 7.62 (s, 1H); 7.68 (dd, 2H); 7.87 (d, 2H); 10.71 (s, 1H). Melting point: 119° C.

The separation into the two enantiomers is carried out by chiral HPLC.

(R)-3-[[(9H-Fluoren-2-ylmethoxy)carbonyl/amino]-2,3,4,9-tetrahydro-]H-carbazole-3-carboxylic Acid 1a $t_R$=6.4 minutes (Chiralcel OD 10 μm LC$_{50}$ 250×4.6 cm, hexane/isopropanol 75:25, 80 ml/minute)

(S)-3-[[(9H-Fluoren-9-ylmethoxy)carbonyl/amino]-2,3,4,9-tetrahydro-]H-carbazole-3-carboxylic Acid 1b $t_R$=7.5 minutes (Chiralcel OD 10 μm of LC$_{50}$ 250×4.6 cm, hexane/isopropanol 75:25, 80 ml/minute)

1-[[(9H-Fluoren-9-ylmethoxy)carbonyl]amino]-4-oxocyclohexanecarboxylic Acid 2

320 mmol (50 g) of 4,4-ethylenedioxycyclohexanone is suspended in 800 ml of 50% EtOH and mixed with 1500 mmol (144.5 g) of $(NH_4)_2CO_3$ and 640 mmol (41.7 g) of KCN. After 5 hours of stirring at 60° C., the ethanol is removed in a vacuum, and the aqueous residue is filtered off with ice after cooling, rewashed with water and dried. Yield: 72.4 g of 4,4-1,4-dioxa-9,11-diazadispiro[4.2.4.2]tetradecane-10,12-dione.

295 mmol (66.8 g) of 4,4–1,4-dioxa-9,11-diazadispiro[4.2.4.2]tetradecane-10,12-dione and 826 mmol (260.6 g) of $Ba(OH)_2\times 8H_2O$ are stirred in 2.5 l in an autoclave for 6 hours at 150° C. After cooling to room temperature, 1032 mmol (99.2 g) of $(NH_4)_2CO_3$ is added to the solution and stirred for one hour at 60° C. The suspension is filtered, rewashed, and the filtrate is freeze-dried. The residue is recrystallized from $H_2O$/MeOH. Yield: 45.4 g of 8-amino-1,4-dioxaspiro[4,5]decane-8-carboxylic acid.

213 mmol (42.9 g) of 8-amino-1,4-dioxaspiro[4,5]decane-8-carboxylic acid in 213 ml of 1N NaOH and 213 mmol (71.9 g) of Fmoc-ONSu in 240 ml of acetonitrile are combined and diluted with 1000 ml of acetonitrile/$H_2O$ 1:1. After the pH is set at 9, it is stirred overnight at room temperature. After the acetontrile is removed in a rotary evaporator, it is acidified with 0.01 M HCl and extracted with ethyl acetate. The extract is washed neutral, dried with $Na_2SO_4$ and evaporated to the dry state. The residue is recrystallized from ethyl acetate/hexane. Yield: 79.0 g of 8-[[(9H-fluoren-9-ylmethoxy)carbonyl]amino]-1,4-dioxaspiro[4,5]decane-8-carboxylic acid.

187 mmol (79 g) of 8-[[(9H-fluoren-9-ylmethoxy)carbonyl]amino]-1,4-dioxaspiro[4,5]decane-8-carboxylic acid is taken up in 3.5 l of acetone/0.1 M HCl 1:1 and stirred for 4 hours at room temperature. The acetone is drawn off in a rotary evaporator, and the precipitated product is filtered off, rewashed with water and dried. Yield: 68.7 g of 2.

$^1$H-NMR (d$^6$-DMSO): δ=1.52–1.73 (m, 4H); 1.82–2.14 (m, 4H); 4.27 (m, 3H); 7.85 (tr, 2H); 7.42 (tr, 2H); 7.67 (s, 1H); 7.75 (d, 2H); 7.91 (d; 2H) Melting point: 157° C.

4-Oxocyclohexanecarboxylic Acid 3

20 mmol (3.4 g) of 4-oxocyclohexanecarboxylic acid ethyl ester is suspended in 40 ml of 2% $H_2SO_4$ and stirred for 2 hours at 90° C. Then, it is extracted 4 times with ethyl acetate, dried with $Na_2SO_4$, and solvent is removed. Recrystallization is carried out from ether/hexane and yields 2.9 g of white solid 3.

$^1$H-NMR (d$^6$-DMSO): δ=1.72 (m, 2H); 2.08–2.18 (m, 2H); 2.19–2.47 (m, 4H); 2.72 (m: 1H); 12.23 (bs; 1H)

4-Chloro-3-[[(phenylamino)carbonyl]amino]benzeneacetic Acid 4

18.55 mmol (2.21 g) of $SOCl_2$ is added slowly while being cooled with ice and while being stirred to 18.55 mmol (4 g) of 4-chloro-3-nitrobenzeneacetic acid in 50 ml of MeOH. After 30 minutes of stirring, it is allowed to heat to room temperature, and another 3.71 mmol (0.44 g) of $SOCl_2$ is added. After being stirred overnight, it is refluxed for 30 minutes. After the solvent is drawn off, it is recrystallized from ether/hexane. Yield: 3.43 g of methyl 4-chloro-3-nitrobenzeneacetate as a yellowish solid.

13.07 mmol (3.0 g) of methyl 4-chloro-3-nitrobenzeneacetate and 198.8 mmol (13.0 g) of Zn dust are refluxed in 500 ml of MeOH for 10 minutes. Then, 13 ml of concentrated HCl is added in drops under reflux and refluxed for another 30 minutes. The suspension is hot-filtered, the methanol is distilled off, and the residue is set at pH 14 with $NaHCO_3$ solution. Extraction with ethyl acetate, drying with $Na_2SO_4$ and distillation of the solution yields 2.3 g of methyl 3-amino-4-chlorobenzeneacetate as a beige solid.

2.08 mmol (415 mg) of methyl 3-amino-3-chlorobenzeneacetate is dissolved in 40 ml of DCM, and mixed at 0° C. with 0.83 mmol (246.3 mg) of triphosgene and 0.6 ml of pyridine. After one hour of stirring at 0° C., 10.4 mmol (1.11 g) of benzylamine is added, and stirring is continued overnight at room temperature. It is extracted with DCM/$H_2O$, the organic phase is dried, and solvent is removed. Yield: 727 mg of methyl 4-chloro-3-[[(phenylamino)carbonyl]amino]bezeneacetate.

2.98 mmol (990 mg) of methyl 4-chloro-3-[[(phenylamino)carbonyl]-amino]benzeneacetate is taken up in 10 ml of methanol and mixed with 6 mmol of 1N NaOH. After 2 hours of stirring at room temperature, the methanol is distilled off, and the residue is acidified with 1 M HCl to pH 2–3. It is extracted with ethyl acetate, dried with $Na_2SO_4$, and solvent is removed. Recrystallization is carried out from boiling isopropanol. Yield: 830 mg of white solid 4.

$^1$H-NMR (d$^6$-DMSO): δ=3.57 (s, 2H); 6.92 (d, 1H); 6.99 (tr, 1H); 7.35–7.50 (m, 3H); 8.10 (s, 1H); 8.30 (s, 1H); 9.42 (s, 1H); 12.40 (bs, 1H).

4-Chloro-3-[[[(phenylmethyl)amino]carbonyl]amino]benzeneacetic Acid 5

2.08 mmol (415 mg) of methyl 3-amino-4-chlorobenzeneacetate is mixed and analogously worked up with 10.4 mmol (969 mg) of aniline as described under 4). Yield: 662 mg of solid.

For ester cleavage, analogously to the above instructions, 2.47 mmol (790 mg) of methyl 4-chloro-3-[[[(phenylmethyl)amino]carbonyl]amino]benzeneacetate is saponified with 1N-NaOH. Product 5 is obtained without recrystallization. Yield: 693 mg of yellowish solid.

ES-MS: 319 (M+H*)

4-Chloro-3-[[(4-pyridinylamino)carbonylamino] benzeneacetic Acid 6

2.08 mmol (415 mg) of methyl 3-amino-4-chlorobenzeneacetate is mixed and analogously worked up with 10.4 mmol (979 mg) of 4-aminopyridine as described under 4).
Yield: 664 mg of solid.

For ester cleavage, 2.63 mmol (840 mg) of methyl 4-chloro-3-[[(4-pyridinylamino)carbonyl]amino]benzeneacetate is saponified with 1N NaOH analogously to the instructions above. Product 6 is obtained without recrystallization. Yield: 481 mg of yellowish solid.

$^1$H-NMR (d$^6$-DMSO): δ=3.57 (s, 2H); 6.94 (d, 1H); 7.40 (m; 3H); 8.05 (s, 1H); 8.35 (d, 2H); 8.50 (s, 1H); 9.92 (s, 1H); 12.40 (bs, 1H)

4-Chloro-3-[[(2-pyridinylamino)carbonyl]amino] benzeneacetic Acid 7

2.08 mmol (415 mg) of methyl 3-amino-4-chlorobenzeneacetate is mixed and analogously worked up with 10.4 mmol (979 ng) of 2-aminopyridine as described under 4.).
Yield: 617 mg of solid.

For ester cleavage, 2.47 mmol (790 mg) of methyl 4-chloro-3-[[(2-pyridinylamino)carbonyl]amino]benzeneacetate is saponified with 1N NaOH analogously to the instructions above. Product 7 is obtained without recrystallization. Yield: 693 mg of yellowish solid.

$^1$H-NMR (d$^6$-DMSO): δ=3.59 (s, 2H); 6.94 (dd, 11H); 7.03 (dd, 1H); 7.22 (d, 1H); 7.42 (d, 1H); 7.78 (dtr, 1H); 8.29 (m, 2H); 10.02 (s, 1H); 11.82 (bs, 1H); 12.50 (s, 1H).

II. Examples of Compounds (I) According to the Invention

Example I 0.3 mmol (42.6 mg) of 4-oxocyclohexanecarboxylic acid is dissolved in 1 ml of acetic acid and added to a suspension of 0.3 mmol (43.3 mg) of phenylhydrazine hydrochloride and 0.3 mmol (40.0 mg) of ZnCl$_3$ in 1 ml of acetic acid. After 20 hours of stirring at 70° C., it is diluted with 20 ml of water and extracted with ethyl acetate. The ethyl acetate phase is washed with water, dried on Na$_2$SO$_4$ and evaporated to the dry state. Yield: 65.6 mg (100%) of white solid.

| Name | Number | $M_{gef}$ | $M_{calc}$ |
|---|---|---|---|
| 2,3,4,9-Tetrahydro-1H-carbazole-3-carboxylic acid | 8 | 215 | 215.2507 |

The column headings that are used here also apply to the examples below (Name, Number of the compound, $M_{gef}$ (determined molecular mass), $M_{calc}$ (calculated molecular mass)), which therefore are no longer repeated.

Example 2

The synthesis is carried out on a 0.2 mmol scale according to instructions A, I and O.

| | | | |
|---|---|---|---|
| 2,3,4,9-Tetrahydro-1H-carbazole-3-carboxylic acid amide | 9 | 214 | 214.2666 |

Example 3

The synthesis is carried out on a 0.2 mmol scale according to instructions A, F, G, I and O.

| | | | |
|---|---|---|---|
| N-[(1S)-1-(Aminocarbonyl)-2-methylpropyl]-(3S)-2,3,4,9-tetrahydro-1H-carbazole-3-carboxamide | 10a | 314 | 313.3987 |
| N-[(1S)-1-(Aminocarbonyl)-2-methylpropyl]-(3R)-2,3,4,9-tetrahydro-1H-carbazole-3-carboxamide | 10b | 314 | 313.3987 |
| N-(2-Amino-2-oxoethyl)-2,3,4,9-tetrahydro-1H-carbazole-3-carboxamide | 11 | 271 | 271.3183 |

Example 4

The synthesis is carried out on a 0.2 mmol scale according to instructions D, F, G, F, G, I and O.

| | | | |
|---|---|---|---|
| N-[(3S)-(2,3,4,9-Tetrahydro-1H-carbazol-3-yl)carbonyl]-L-valyl-L-glutamine | 12a | 442 | 442.513 |
| N-[(3R)-(2,3,4,9-Tetrahydro-1H-carbazol-3-yl)carbonyl]-L-valyl-L-glutamine, isomer B | 12b | 442 | 442.513 |

Example 5

The synthesis is carried out on a 0.2 mmol scale according to instructions D, F, G, I, F and O:

| | | | |
|---|---|---|---|
| N-[[(3S)-3-Amino-2,3,4,9-tetrahydro-1H-carbazol-3-yl]-carbonyl]-L-alanine | 13 | 301 | 301.3441 |

Example 6

0.1 mmol of carboxylic acid, 0.1 mmol of HOBt, and 0.15 mmol of amine components are dissolved in 15 ml of dry DMF (also THF, DCM), and 0.5 mmol of NMM is added while being cooled with ice and stirred. After about 15 minutes, 0.15 mmol of EDCI×HCl is added, it is stirred for one more hour, it is heated to room temperature, and stirring is continued overnight. For working-up, the solvent is drawn off, the product is dissolved in ethyl acetate, and washed twice each with 0.1N HCl and saturated NaCl solution. After the solvent is dried and drawn off, it is recrystallized, if necessary.

| | | | |
|---|---|---|---|
| 9H-Fluoren-9-ylmethyl [(3S)-3-[[[(4-bromophenyl)-methyl]amino]carbonyl]-2,3,4,9-tetrahydro-1H-carbazol-3-yl]carbamate | 14 | 620 | 620.5439 |
| Methyl N-[[(3S)-3-[[(9H-fluoren-9-ylmethoxy)carbonyl]-amino]-2,3,4,9-tetrahydro-1H-carbazol-3-yl]carbonyl]-L-alaninate | 15 | 537 | 537.6129 |

Example 7

The synthesis is carried out on a 0.2 mmol scale according to instructions A, F, G, F, G, F, G and O.

| Compound | No. | MW | Mass |
|---|---|---|---|
| N-[[(3R)-3-[[(2S,3S)-2-[[(9H-Fluoren-9-ylmethoxy)-carbonyl]amino]-3-methyl-1-oxopentyl]amino]-2,3,4,9-tetrahydro-1H-carbazol-3-yl]carbonyl]-L-valyl-L-aspartamide | 16 | 779 | 777.9178 |
| N-[[(3S)-3-[[(2S,3S)-2-[[(9H-Fluoren-9-ylmethoxy)-carbonyl]amino]-3-methyl-1-oxopentyl]amino]-2,3,4,9-tetrahydro-1H-carbazol-3-yl]carbonyl]-L-valyl-L-aspartamide | 17 | 779 | 777.9178 |
| N-[[(3R)-2,3,4,9-Tetrahydro-3-[(1-oxo-2,3-diphenyl-propyl)amino]-1H-carbaol-3-yl]-carbonyl]-L-valyl-L-aspartamide | 18 | 651 | 650.7758 |
| N-[[(3S)-2,3,4,9-Tetrahydro-3-[(1-oxo-2,3-diphenyl-propyl)amino]-1H-carbazol-3-yl]-carbonyl]-L-valyl-L-aspartamide, isomer A | 19 | 651 | 650.7758 |
| N-[[(3S)-2,3,4,9-Tetrahydro-3-[(1-oxo-2,3-diphenyl-propyl)amino]-1H-carbazol-3-yl]-carbonyl]-L-valyl-L-aspartamide, isomer B | 20 | 651 | 650.7758 |
| N-[[(3S)-2,3,4,9-Tetrahydro-3-[[(2S,3S)-3-methyl-1-oxo-2-[(1-oxo-3-phenylpropyl)amino]-pentyl]amino]-1H-carbazol-3-yl]carbonyl]-L-valyl-L-aspartamide | 21 | 688 | 687.8371 |
| N-[[(3R)-2,3,4,9-Tetrahydro-3-[[(2S,3S)-3-methyl-1-oxo-2-[(1-oxo-3-phenylpropyl)amino]-pentyl]amino]-1H-carbazol-3-yl]carbonyl]-L-valyl-L-aspartamide | 22 | 688 | 687.8371 |
| N-[[(3S)-2,3,4,9-Tetrahydro-3-[[(2S)-1-oxo-2-[[(phenylmethoxy)carbonyl]amino]propyl]-amino]-1H-carbazol-3-yl]carbonyl]-L-valyl-L-aspartamide | 23 | 648 | 647.7289 |
| N-[[(3R)-2,3,4,9-Tetrahydro-3-[[(2S)-1-oxo-2-[[(phenylmethoxy)carbonyl]amino]propyl]-amino]-1H-carbazol-3-yl]carbonyl]-L-valyl-L-aspartamide | 24 | 648 | 647.7289 |
| N-[[(3R)-2,3,4,9-Tetrahydro-3-[[(2S,3S)-3-methyl-1-oxo-2-[[(phenylmethoxy)carbonyl]-amino]pentyl]amino]-1H-carbazol-3-yl]carbonyl]-L-alanyl-L-aspartamide | 25 | 662 | 661.7557 |
| N-[[(3R)-2,3,4,9-Tetrahydro-3-[[(2S,3S)-3-methyl-1-oxo-2-[[(phenylmethoxy)carbonyl]-amino]pentyl]amino]-1H-carbazol-3-yl]carbonyl]-L-valyl-L-alaninamide | 26 | 647 | 646.7844 |
| N-[[(3S)-2,3,4,9-Tetrahydro-3-[[(2S,3S)-3-methyl-1-oxo-2-[[(phenylmethoxy)carbonyl]-amino]pentyl]amino]-1H-carbazol-3-yl]carbonyl]-D-valyl-L-aspartamide | 27 | 690 | 689.8093 |
| N-[[(3R)-2,3,4,9-Tetrahydro-3-[[(2S,3S)-3-methyl-1-oxo-2-[[(phenylmethoxy)carbonyl]-amino]pentyl]amino]-1H-carbazol-3-yl]carbonyl]-D-valyl-L-aspartamide | 28 | 690 | 689.8093 |
| N-[[(3R)-2,3,4,9-Tetrahydro-3-[[(2S,3S)-3-methyl-1-oxo-2-[[(phenylmethoxy)carbonyl]-amino]pentyl]amino]-1H-carbazol-3-yl]carbonyl]-L-valyl-D-aspartamide | 29 | 690 | 689.8093 |
| N-[[(3S)-2,3,4,9-Tetrahydro-3-[[(2S,3S)-3-methyl-1-oxo-2-[[(phenylmethoxy)carbonyl]-amino]pentyl]amino]-1H-carbazol-3-yl]carbonyl]-L-valyl-D-aspartamide | 30 | 690 | 689.8093 |
| N-[[(3S)-2,3,4,9-Tetrahydro-3-[[(2S,3S)-3-methyl-1-oxo-2-[[(phenylmethoxy)carbonyl]-amino]pentyl]amino]-1H-carbazol-3-yl]carbonyl]-L-alanyl-L-aspartamide | 31 | 662 | 661.7557 |
| N-[[(3S)-2,3,4,9-Tetrahydro-3-[(phenylacetyl)-amino]-1H-carbazol-3-yl]carbonyl]-L-valyl-L-aspartamide | 32 | 651 | 560.6514 |
| N-[[(3R)-2,3,4,9-Tetrahydro-3-[(1-oxo-3-phenylpropyl)amino]-1H-carbazol-3-yl]carbonyl]-L-valyl-L-aspartamide | 33 | 575 | 574.6782 |
| N-[[(3S)-2,3,4,9-Tetrahydro-3-[(1-oxo-3-phenylpropyl)amino]-1H-carbazol-3-yl]carbonyl]-L-valyl-L-aspartamide | 34 | 575 | 574.6782 |
| N-[[(3S)-2,3,4,9-Tetrahydro-3-[[(2S,3S)-3-methyl-1-oxo-2-[[(phenylmethoxy)carbonyl]-amino]pentyl]amino]-1H-carbazol-3-yl]carbonyl]-L-valyl-L-alaninamide | 35 | 647 | 646.7844 |
| N-[[(3R)-2,3,4,9-Tetrahydro-3-[(phenylacetyl)-amino]-1H-carbazol-3-yl]carbonyl]-L-valyl-L-aspartamide | 36 | 561 | 560.6514 |
| N-[[(3R)-2,3,4,9-Tetrahydro-3-[(1-oxo-4-phenylbutyl)amino]-1H-carbazol-3-yl]carbonyl]-L-valyl-L-aspartamide | 37 | 589 | 588.705 |
| N-[[(3S)-2,3,4,9-Tetrahydro-3-[(1-oxo-4-phenylbutyl)amino]-1H-carbazol-3-yl]carbonyl]-L-valyl-L-aspartamide | 38 | 589 | 588.705 |
| N-[[(3R)-3-[(Diphenylacetyl)amino]-2,3,4,9-tetrahydro-1H-carbazol-3-yl]carbonyl]-L-valyl-L-aspartamide | 39 | 637 | 636.749 |
| N-[[(3S)-3-[(Diphenylacetyl)amino]-2,3,4,9-tetrahydro-1H-carbazol-3-yl]carbonyl]-L-valyl-L-aspartamide | 40 | 637 | 636.749 |
| N-[[(3R)-2,3,4,9-Tetrahydro-3-[(1-oxo-2-phenylpropyl)amino]-1H-carbazol-3-yl]carbonyl]-L-valyl-L-aspartamide, Isomer A | 41 | 575 | 574.6782 |
| N-[[(3R)-2,3,4,9-Tetrahydro-3-[(3-methyl-1-oxo-2-phenylpentyl)amino]-1H-carbazol-3-yl]-carbonyl]-L-valyl-L-aspartamide, Isomer B | 42 | 617 | 616.7586 |
| N-[[(3S)-2,3,4,9-Tetrahydro-3-[(3-methyl-1-oxo-2-phenylpentyl)amino]-1H-carbazol-3-yl]-carbonyl]-L-valyl-L-aspartamide, Isomer A | 43 | 617 | 616.7586 |
| N-[[(3S)-2,3,4,9-Tetrahydro-3-[(3-methyl-1-oxo-2-phenylpentyl)amino]-1H-carbazol-3-yl]-carbonyl]-L-valyl-L-aspartamide, Isomer B | 44 | 617 | 616.7586 |
| Phenylmethyl [(1S,2S)-1-[[[(3R)-3-[[[(1S)-1-[[[4-(aminocarbonyl)phenyl]amino]carbonyl]-2-methylpropyl]amino]carbonyl]-2,3,4,9-tetrahydro-1H-carbazol-3-yl]amino]carbonyl]-2-methylbutyl]carbamate | 45 | 695 | 694.8284 |
| Phenylmethyl [(1S,2S)-1-[[[(3S)-3-[[[(1S)-1-[[[[4-(aminocarbonyl)phenyl]amino]carbonyl]-2-methylpropyl]amino]carbonyl]-2,3,4,9-tetrahydro-1H-carbazol-3-yl]amino]carbonyl]-2-methyl-butyl]carbamate | 46 | 695 | 694.8284 |
| N-[[(3S)-2,3,4,9-Tetrahydro-3-[(3-methyl-1-oxo-2-phenylbutyl)amino]-1H-carbazol-3-yl]-carbonyl]-L-valyl-L-aspartamide, Isomer A | 47 | 603 | 602.7318 |
| N-[[(3S)-2,3,4,9-Tetrahydro-3-[(3-methyl-1-oxo-2-phenylbutyl)amino]-1H-carbazol-3-yl]-carbonyl]-L-valyl-L-aspartamide, Isomer B | 48 | 603 | 602.7318 |
| N-[[(3R)-2,3,4,9-Tetrahydro-3-[(3-methyl-1-oxo-2-phenylbutyl)amino]-1H-carbazol-3-yl]-carbonyl]-L-valyl-L-aspartamide | 49 | 603 | 602.7318 |
| Phenylmethyl [(1S,2S)-1-[[[(3S)-3-[[[(1S)-1-[[[[4-(aminocarbonyl)cyclohexyl]methyl]-amino]carbonyl]-2-methylpropyl]amino]-carbonyl]-2,3,4,9-tetrahydro-1H-carbazol-3-yl]-amino]carbonyl]-2-methylbutyl]carbamate | 50 | 715 | 714.9026 |
| N-[[(3R)-2,3,4,9-Tetrahydro-3-[[(3-phenoxyphenyl)acetyl]-amino]-1H-carbazol-3-yl]-carbonyl]-L-valyl-L-aspartamide | 51 | 653 | 652.748 |
| N-[[(3S)-2,3,4,9-Tetrahydro-3-[[(3-phenoxyphenyl)acetyl]-amino]-1H-carbazol-3-yl]-carbonyl]-L-valyl-L-aspartamide | 52 | 653 | 652.748 |
| Phenylmethyl [(1S,2S)-1-[[[(3R)-3-[[[(1S)-1-[[[[3-(aminocarbonyl)phenyl]methyl]amino]-carbonyl]-2-methylpropyl]amino]carbonyl]-2,3,4,9-tetrahydro-1H-carbazol-3-yl]amino]-carbonyl]-2-methylbutyl]carbamate | 53 | 709 | 708.8552 |
| Phenylmethyl [(1S,2S)-1-[[[(3S)-3-[[[(1S)-1-[[[[3-(aminocarbonyl)phenyl]methyl]amino]-carbonyl]-2-methylpropyl]amino]carbonyl]-2,3,4,9-tetrahydro-1H-carbazol-3-yl]amino]-carbonyl]-2-methylbutyl]carbamate | 54 | 709 | 708.8552 |
| (3R)-N-[(1S)-1-(Aminocarbonyl)-2-methylpropyl]-2,3,4,9-tetrahydro-3-[[(2R)-1-oxo-2-[(1-oxo-3-phenylpropyl)-amino]-3-phenylpropyl]amino]-1H-carbazole-3-carboxamide | 55 | 608 | 607.7509 |
| N-[[(3S)-2,3,4,9-Tetrahydro-3-[(1-oxo-2-phenylpropyl)-amino]-1H-carbazol-3-yl]-carbonyl]-L-valyl-L-aspartamide | 56 | 575 | 574.6782 |

| Compound | No. | MW | Mass |
|---|---|---|---|
| Phenylmethyl [(1S,2S)-1-[[[(3R)-3-[[[(1S)-1-[[[[4-(aminocarbonyl)cyclohexyl]methyl]-amino]carbonyl]-2-methylpropyl]amino]-carbonyl]-2,3,4,9-tetrahydro-1H-carbazol-3-yl]-amino]carbonyl]-2-methylbutyl]carbamate | 57 | 715 | 714.9026 |

Example 8

The synthesis is carried out on a 0.2 mmol-scale according to instructions A, F, G, F, G and O.

| Compound | No. | MW | Mass |
|---|---|---|---|
| Phenylmethyl [(1S,2S)-1-[[[(3R)-3-[[[(1S)-1-(aminocarbonyl)-2-methylpropyl]amino]-carbonyl]-2,3,4,9-tetrahydro-1H-carbazol-3-yl]-amino]carbonyl]-2-methylbutyl]carbamate | 58 | 576 | 575.7059 |
| N-[[(3S)-3[[(9H-Fluoren-9-ylmethoxy)-carbonyl]amino]-2,3,4,9-tetrahydro-1H-carbazol-3-yl]carbonyl]-L-valyl-L-aspartamide | 59 | 665 | 664.759 |
| N-[[(3R)-3-[[(9H-Fluoren-9-ylmethoxy)-carbonyl]amino]-2,3,4,9-tetrahydro-1H-carbazol-3-yl]carbonyl]-L-valyl-L-aspartamide | 60 | 665 | 664.759 |
| Phenylmethyl [(1S,2S)-1-[[[(3S)-3-[[[(1S)-1-(aminocarbonyl)-2-methylpropyl]amino]-carbonyl]-2,3,4,9-tetrahydro-1H-carbazol-3-yl]-amino]carbonyl]-2-methylbutyl]carbamate | 61 | 576 | 575.7059 |
| Phenylmethyl [(1S,2S)-1-[[[(3R)-3-[[[4-(aminocarbonyl)phenyl]amino]carbonyl]-2,3,4,9-tetrahydro-1H-carbazol-3-yl]amino]-carbonyl]-2-methylbutyl]carbamate | 62 | 596 | 595.6963 |
| Phenylmethyl [(1S,2S)-1-[[[(3S)-3-[[[4-(aminocarbonyl)phenyl]amino]carbonyl]-2,3,4,9-tetrahydro-1H-carbazol-3-yl]amino]-carbonyl]-2-methylbutyl]carbamate | 63 | 596 | 595.6963 |
| Phenylmethyl [(1S,2S)-1-[[[(3R)-3-[[[(1S,2S)-1-(aminocarbonyl)-2-methylbutyl]amino]-carbonyl]-2,3,4,9-tetrahydro-1H-carbazol-3-yl]-amino]carbonyl]-2-methylbutyl]carbamate | 64 | 590 | 589.7327 |
| Phenylmethyl [(1S,2S)-1-[[[(3S)-3-[[[(1S,2S)-1-(aminocarbonyl)-2-methylbutyl]amino]-carbonyl]-2,3,4,9-tetrahydro-1H-carbazol-3-yl]-amino]carbonyl]-2-methylbutyl]carbamate | 65 | 590 | 589.7327 |
| Phenylmethyl [(1S,2S)-1-[[[(3R)-3-[[[(1S)-2-amino-2-oxo-1-(phenylmethyl)ethyl]amino]-carbonyl]-2,3,4,9-tetrahydro-1H-carbazol-3-yl]-amino]carbonyl]-2-methylbutyl]carbamate | 66 | 623 | 623.7499 |
| Phenylmethyl [(1S,2S)-1-[[[(3S)-3-[[[(1S)-2-amino-2-oxo-1-(phenylmethyl)ethyl]amino]-carbonyl]-2,3,4,9-tetrahydro-1H-carbazol-3-yl]-amino]carbonyl]-2-methylbutyl]carbamate | 67 | 623 | 623.7499 |
| (3R)-N-[(1S)-1-(Aminocarbonyl)-2-methyl-propyl]-2,3,4,9-tetrahydro-3-[(1-oxo-2-phenyl-propyl)amino]-1H-carbazole-3-carboxamide | 68 | 460 | 460.5748 |
| Phenylmethyl [(1S,2S)-1-[[[(3S)-3-[[[3-(aminocarbonyl)phenyl]methyl]amino]-carbonyl]-2,3,4,9-tetrahydro-1H-carbazol-3-yl]-amino]carbonyl]-2-methylbutyl]carbamate | 69 | 610 | 609.7231 |
| Phenylmethyl [(1S,2S)-1-[[[(3R)-3-[[[3-(aminocarbonyl)phenyl]methyl]amino]-carbonyl]-2,3,4,9-tetrahydro-1H-carbazol-3-yl]-amino]carbonyl]-2-methylbutyl]carbamate | 70 | 610 | 609.7231 |
| Phenylmethyl [(1S,2S)-1-[[[(3S)-3-[[[4-(aminocarbonyl)cyclohexyl]methyl]amino]-carbonyl]-2,3,4,9-tetrahydro-1H-carbazol-3-yl]-amino]carbonyl]-2-methylbutyl]carbamate | 71 | 615 | 615.7705 |
| Phenylmethyl [(1S,2S)-1-[[[(3R)-3-[[[4-(aminocarbonyl)cyclohexyl]methyl]amino]-carbonyl]-2,3,4,9-tetrahydro-1H-carbazol-3-yl]-amino]carbonyl]-2-methylbutyl]carbamate | 72 | 615 | 615.7705 |
| Phenylmethyl [(1S,2S)-1-[[[(3S)-3-[[[3-(aminocarbonyl)phenyl]amino]carbonyl]-2,3,4,9-tetrahydro-1H-carbazol-3-yl]amino]-carbonyl]-2-methylbutyl]carbamate | 73 | 596 | 595.6963 |
| Phenylmethyl [(1S,2S)-1-[[[(3R)-3-[[[3-(aminocarbonyl)phenyl]amino]carbonyl]-2,3,4,9-tetrahydro-1H-carbazol-3-yl]amino]-carbonyl]-2-methylbutyl]carbamate | 74 | 596 | 595.6963 |
| Phenylmethyl [(1S,2S)-1-[[[(3S)-3-[[[(1S)-2-amino-2-oxo-1-phenylethyl]amino]carbonyl]-2,3,4,9-tetrahydro-1H-carbazol-3-yl]amino]-carbonyl]-2-methylbutyl]carbamate | 75 | 610 | 609.7231 |
| Phenylmethyl [(1S,2S)-1-[[[(3S)-3-[[[(1R)-2-amino-2-oxo-1-phenylethyl]amino]carbonyl]-2,3,4,9-tetrahydro-1H-carbazol-3-yl]amino]-carbonyl]-2-methylbutyl]carbamate | 76 | 610 | 609.7231 |
| Phenylmethyl [(1S,2S)-1-[[[(3R)-3-[[(2-amino-2-oxo-1-phenylethyl)amino]carbonyl]-2,3,4,9-tetrahydro-1H-carbazol-3-yl]amino]carbonyl]-2-methylbutyl]carbamate, Isomer A | 77 | 609 | 609.7231 |
| Phenylmethyl [(1S,2S)-1-[[[(3R)-3-[[(2-amino-2-oxo-1-phenylethyl)amino]carbonyl]-2,3,4,9-tetrahydro-1H-carbazol-3-yl]amino]carbonyl]-2-methylbutyl]carbamate, Isomer B | 78 | 609 | 609.7231 |
| (3R)-N-[(1S)-1-(Aminocarbonyl)-2-methyl-propyl]-2,3,4,9-tetrahydro-3-[[(3-hydroxy-phenyl)acetyl]amino]-1H-carbazole-3-carboxamide | 79 | 462 | 462.547 |
| (3R)-3-[[[3-(Acetyloxy)phenyl]acetyl]-amino]-N-[(1S)-1-(aminocarbonyl)-2-methyl-propyl]-2,3,4,9-tetrahydro-1H-carbazole-3-carboxamide | 80 | 504 | 504.5838 |
| 3-[2-[[(3R)-3-[[[(1S)-1-(Aminocarbonyl)-2-methylpropyl]amino]carbonyl]-2,3,4,9-tetrahydro-1H-carbazol-3-yl]amino]-2-oxoethyl]phenyl 3-hydroxybenzeneacetate | 81 | 597 | 596.6804 |
| (3R)-N-[(1S)-1-(Aminocarbonyl)-2-methyl-propyl]-2,3,4,9-tetrahydro-3-[(hydroxyphenyl-acetyl)amino]-1H-carbazole-3-carboxamide | 82 | 462 | 462.547 |
| (3R)-N-[(1S)-1-(Aminocarbonyl)-2-methyl-propyl]-3-[[(4-bromophenyl)acetyl]amino]-2,3,4,9-tetrahydro-1H-carbazole-3-carboxamide | 83 | 525 | 525.4441 |
| (3R)-N-[(1S)-1-(Aminocarbonyl)-2-methyl-propyl]-3-[[(2-chlorophenyl)acetyl]-amino]-2,3,4,9-tetrahydro-1H-carbazole-3-carboxamide | 84 | 481 | 480.9931 |
| (3R)-N-[(1S)-1-(Aminocarbonyl)-2-methyl-propyl]-3-[[(3-chloro-4-hydroxyphenyl)-acetyl]amino]-2,3,4,9-tetrahydro-1H-carbazole-3-carboxamide | 85 | 497 | 496.9921 |
| (3R)-3-[[[4-(Acetyloxy)-3-chlorophenyl]-acetyl]amino]-N-[(1S)-1-(aminocarbonyl)-2-methylpropyl]-2,3,4,9-tetrahydro-1H-carbazole-3-carboxamide | 86 | 539 | 539.0289 |
| (3R)-N-[(1S)-1-(Aminocarbonyl)-2-methyl-propyl]-3-[[(3-fluoro-4-hydroxyphenyl)acetyl]-amino]-2,3,4,9-tetrahydro-1H-carbazole-3-carboxamide | 87 | 481 | 480.5371 |
| (3R)-3-[[[4-(Acetyloxy)-3-fluorophenyl]acetyl]-amino]-N-[(1S)-1-(aminocarbonyl)-2-methyl-propyl]-2,3,4,9-tetrahydro-1H-carbazole-3-carboxamide | 88 | 523 | 522.5739 |
| (3R)-N-[(1S)-1-(Aminocarbonyl)-2-methyl-propyl]-2,3,4,9-tetrahydro-3-[[(4-nitrophenyl)-acetyl]amino]-1H-carbazole-3-carboxamide | 89 | 492 | 491.5451 |
| (3R)-N-[(1S)-1-(Aminocarbonyl)-2-methyl-propyl]-3-[[(2,4-dichlorophenyl)acetyl]amino]-2,3,4,9-tetrahydro-1H-carbazole-3-carboxamide | 90 | 515 | 515.4382 |
| (3R)-N-[(1S)-1-(Aminocarbonyl)-2-methyl-propyl]-3-[[(4-fluorophenyl)acetyl]amino]-2,3,4,9-tetrahydro-1H-carbazole-3-carboxamide | 91 | 464 | 464.5381 |
| (3R)-N-[(1S)-1-(Aminocarbonyl)-2-methyl-propyl]-2,3,4,9-tetrahydro-3-[[(4-hydroxy-phenyl)acetyl]amino]-1H-carbazole-3-carboxamide | 92 | 462 | 462.547 |
| (3R)-N-[(1S)-1-(Aminocarbonyl)-2-methyl-propyl]-3-[[(2-bromophenyl)acetyl]amino]-2,3,4,9-tetrahydro-1H-carbazole-3-carboxamide | 93 | 525 | 525.4441 |
| (3R)-N-[(1S)-1-(Aminocarbonyl)-2-methyl-propyl]-2,3,4,9-tetrahydro-3-[[(2-nitrophenyl)-acetyl]amino]-1H-carbazole-3-carboxamide | 94 | 491 | 491.5451 |

-continued

| Compound | No. | MW | Mass |
|---|---|---|---|
| (3R)-N-[(1S)-1-(Aminocarbonyl)-2-methyl-propyl]-2,3,4,9-tetrahydro-3-[[(3-nitrophenyl)-acetyl]amino]-1H-carbazole-3-carboxamide | 95 | 491 | 491.5451 |
| (3R)-N-[(1S)-1-(Aminocarbonyl)-2-methyl-propyl]-3-[[(3-bromophenyl)acetyl]-amino]-2,3,4,9-tetrahydro-1H-carbazole-3-carboxamide | 96 | 525 | 525.4441 |
| (3R)-N-[(1S)-1-(Aminocarbonyl)-2-methyl-propyl]-3-[[(2-chloro-4-fluorophenyl)acetyl]-amino]-2,3,4,9-tetrahydro-1H-carbazole-3-carboxamide | 97 | 499 | 498.9832 |
| (3R)-N-[(1S)-1-(Aminocarbonyl)-2-methyl-propyl]-3-[([1,1'-biphenyl]-4-ylacetyl)amino]-2,3,4,9-tetrahydro-1H-carbazole-3-carboxamide | 98 | 523 | 522.6456 |
| (3R)-N-[(1S)-1-(Aminocarbonyl)-2-methyl-propyl]-3-[[(3,5-dimethylphenyl)acetyl]amino]-2,3,4,9-tetrahydro-1H-carbazole-3-carboxamide | 99 | 475 | 474.6016 |
| (3R)-N-[(1S)-1-(Aminocarbonyl)-2-methyl-propyl]-3-[(1,3-benzodioxol-5-ylacetyl)amino]-2,3,4,9-tetrahydro-1H-carbazole-3-carboxamide | 100 | 490 | 490.557 |
| (3R)-N-[(1S)-1-(Aminocarbonyl)-2-methyl-propyl]-3-[[(3-chlorophenyl)acetyl]amino]-2,3,4,9-tetrahydro-1H-carbazole-3-carboxamide | 101 | 481 | 480.9931 |
| (3R)-N-[(1S)-1-(Aminocarbonyl)-2-methyl-propyl]-2,3,4,9-tetrahydro-3-[[(3-methyl-phenyl)acetyl]amino]-1H-carbazole-3-carboxamide | 102 | 461 | 460.5748 |
| (3R)-N-[(1S)-1-(Aminocarbonyl)-2-methyl-propyl]-3-[[(2-fluorophenyl)acetyl]amino]-2,3,4,9-tetrahydro-1H-carbazole-3-carboxamide | 103 | 464 | 464.5381 |
| (3R)-N-[(1S)-1-(Aminocarbonyl)-2-methyl-propyl]-2,3,4,9-tetrahydro-3-[[(2-methyl-phenyl)acetyl]amino]-1H-carbazole-3-carboxamide | 104 | 461 | 460.5748 |
| (3R)-N-[(1S)-1-(Aminocarbonyl)-2-methyl-propyl]-2,3,4,9-tetrahydro-3-[[[4-(1-methyl-ethyl)phenyl]acetyl]amino]-1H-carbazole-3-carboxamide | 105 | 489 | 488.6284 |
| (3R)-N-[(1S)-1-(Aminocarbonyl)-2-methyl-propyl]-3-[[[4-(dimethylamino)phenyl]acetyl]-amino]-2,3,4,9-tetrahydro-1H-carbazole-3-carboxamide | 106 | 490 | 489.6165 |
| (3R)-N-[(1S)-1-(Aminocarbonyl)-2-methyl-propyl]-2,3,4,9-tetrahydro-3-[[[4-(methyl-sulfonyl)phenyl]acetyl]amino]-1H-carbazole-3-carboxamide | 107 | 524 | 524.6388 |
| (3R)-N-[(1S)-1-(Aminocarbonyl)-2-methyl-propyl]-3-[[(3-fluoro-4-methylphenyl)acetyl]-amino]-2,3,4,9-tetrahydro-1H-carbazole-3-carboxamide | 108 | 478 | 478.5649 |

Example 9

The synthesis is carried out on a 0.2 mmol-scale according to instructions B, F, G, F, G, F, G and O.

| Compound | No. | MW | Mass |
|---|---|---|---|
| N-[[(3R)-2,3,4,9-Tetrahydro-3-[[(2S,3S)-3-methyl-1-oxo-2-[[(phenylmethoxy)carbonyl]-amino]pentyl]amino]-1H-carbazol-3-yl]-carbonyl]-L-valyl-L-asparagine | 109 | 691 | 690.7934 |
| N-[[(3S)-2,3,4,9-Tetrahydro-3-[[(2S,3S)-3-methyl-1-oxo-2-[[(phenylmethoxy)carbonyl]-amino]pentyl]amino]-1H-carbazol-3-yl]-carbonyl]-L-valyl-L-asparagine | 110 | 691 | 690.7934 |

Example 10

The synthesis is carried out on a 0.2 mmol-scale according to instructions A, F, G, F, G, F, G, F, H and O.

| Compound | No. | MW | Mass |
|---|---|---|---|
| N-[[(3R)-3-[[(2S,3S)-2-(Acetylamino)-3-methyl-1-oxopentyl]amino]-2,3,4,9-tetrahydro-1H-carbazol-3-yl]carbonyl]-L-valyl-L-aspartamide | 111 | 598 | 597.7127 |
| N-[[(3S)-3-[[(2S,3S)-2-(Acetylamino)-3-methyl-1-oxopentyl]amino]-2,3,4,9-tetrahydro-1H-carbazol-3-yl]carbonyl]-L-valyl-L-aspartamide | 112 | 598 | 597.7127 |
| N-[[(3R)-3-[[(2R,3R)-2-(Acetylamino)-3-methyl-1-oxopentyl]amino]-2,3,4,9-tetrahydro-1H-carbazol-3-yl]carbonyl]-L-valyl-L-aspartamide | 113 | 598 | 597.7127 |
| N-[[(3S)-3-[[(2R,3R)-2-(Acetylamino)-3-methyl-1-oxopentyl]amino]-2,3,4,9-tetrahydro-1H-carbazol-3-oxopentyl]amino]-2,3,4,9-tetrahydro-1H-carbazol-3-yl]carbonyl]-L-valyl-L-aspartamide | 114 | 598 | 597.7127 |

Example 11

The synthesis is carried out on a 0.2 mmol-scale according to instructions A, F, G, F, G, F, H and O.

| Compound | No. | MW | Mass |
|---|---|---|---|
| N-[[(3R)-3-(Acetylamino)-2,3,4,9-tetrahydro-1H-carbazol-3-yl]carbonyl]-L-valyl-L-aspartamide | 115 | 484 | 484.5538 |
| N-[[(3S)-3-(Acetylamino)-2,3,4,9-tetrahydro-1H-carbazol-3-yl]carbonyl]-L-valyl-L-aspartamide | 116 | 484 | 484.5538 |
| N-[[(3S)-3-(Acetylamino)-2,3,4,9-tetrahydro-1H-carbazol-3-yl]carbonyl]-D-valyl-L-aspartamide | 117 | 484 | 484.5538 |
| N-[[(3S)-3-(Acetylamino)-2,3,4,9-tetrahydro-1H-carbazol-3-yl]carbonyl]-L-valyl-D-aspartamide | 118 | 484 | 484.5538 |

Example 12

The synthesis is carried out on a 0.2 mmol-scale according to instructions A, F, G and O.

| Compound | No. | MW | Mass |
|---|---|---|---|
| Phenylmethyl [(1S,2S)-1-[[[(3R)-3-(aminocarbonyl)-2,3,4,9-tetrahydro-1H-carbazol-3-yl]amino]carbonyl]-2-methylbutyl]carbamate | 119 | 476 | 476.5738 |
| Phenylmethyl [(1S,2S)-1-[[[(3S)-3-(aminocarbonyl)-2,3,4,9-tetrahydro-1H-carbazol-3-yl]amino]carbonyl]-2-methylbutyl]carbamate | 120 | 476 | 476.5738 |

Example 13

The synthesis is carried out on a 0.2 mmol-scale according to instructions A, F, G, F, G, F, G, F, G and O.

| | | | |
|---|---|---|---|
| N-[[(3R)-2,3,4,9-Tetrahydro-3-[[(2S)-1-oxo-2-[(1-oxo-3-phenylpropyl)amino]-3-phenylpropyl]amino]-1H-carbazol-3-yl]carbonyl]-L-valyl-L-aspartamide | 121 | 722 | 721.8543 |
| N-[[(3R)-2,3,4,9-Tetrahydro-3-[[2R,3R)-3-methyl-1-oxo-2-[(1-oxo-3-phenylpropyl)amino]pentyl]amino]-1H-carbazol-3-yl]carbonyl]-L-valyl-L-aspartamide | 122 | 688 | 687.8371 |

Example 14

The synthesis is carried out on a 0.2 mmol-scale according to instructions D, F, G, F, G and O.

| | | | |
|---|---|---|---|
| N-[[(3R)-2,3,4,9-Tetrahydro-3-[[(2S,3S)-3-methyl-1-oxo-2-[[(phenylmethoxy)carbonyl]amino]pentyl]amino]-1H-carbazol-3-yl]carbonyl]-L-valine, N-[[(3R)-2,3,4,9-Tetrahydro-3-[[(2S)-3-methyl-1-oxo-2-[[(phenylmethoxy)carbonyl]amino]pentyl]amino]-1H-carbazol-3-yl]carbonyl]-L-valine | 123 | 577 | 576.69 |
| N-[[(3S)-2,3,4,9-Tetrahydro-3-[[(2S,3S)-3-methyl-1-oxo-2-[[(phenylmethoxy)carbonyl]amino]pentyl]amino]-1H-carbazol-3-yl]carbonyl]-L-valine | 124 | 577 | 576.69 |

Example 15

The synthesis is carried out on a 0.2 mmol-scale according to instructions C, F, G, F, G, F, G and P.

| | | | |
|---|---|---|---|
| N-[[(3R)-3-[[(2S,3S)-2-[[(1,1-Dimethylethoxy)carbonyl]amino]-3-methyl-1-oxopentyl]amino]-2,3,4,9-tetrahydro-1H-carbazol-3-yl]carbonyl]-L-valyl-L-aspartamide | 125 | 656 | 655.7921 |

Example 16

The synthesis is carried out on a 0.2 mmol-scale according to instructions A, F, G, F, G, F and O.

| | | | |
|---|---|---|---|
| N-[[(3S)-3-Amino-2,3,4,9-tetrahydro-1H-carbazol-3-yl]carbonyl]-L-valyl-L-aspartamide | 126 | 442 | 442.517 |
| N-[[(3R)-3-Amino-2,3,4,9-tetrahydro-1H-carbazol-3-yl]carbonyl]-L-valyl-L-aspartamide | 127 | 442 | 442.517 |
| (3S)-N-[(1S)-1-(Aminocarbonyl)-2-methylpropyl]-3-[[(2S,3S)-2-amino-3-methyl-1-oxopentyl]amino]-2,3,4,9-tetrahydro-1H-carbazole-3-carboxamide | 128 | 441 | 441.5725 |

Example 17

The synthesis is carried out on a 0.2 mmol-scale according to instructions D, F, G, F, G, F, H and O.

| | | | |
|---|---|---|---|
| N-[[(3S)-3-(Acetylamino)-2,3,4,9-tetrahydro-1H-carbazol-3-yl]carbonyl]-L-valyl-L-asparagine | 129 | 435 | 485.5379 |

Example 18

The synthesis is carried out on a 0.2 mmol-scale according to instructions A, F, G, F, H and O.

| | | | |
|---|---|---|---|
| (3R)-3-(Acetylamino)-N-[(1S)-2-amino-2-oxo-1-(phenylmethyl)ethyl]-2,3,4,9-tetrahydro-1H-carbazole-3-carboxamide | 130 | 418 | 418.4944 |
| (3S)-3-(Acetylamino)-N-[(1S)-2-amino-2-oxo-1-(phenylmethyl)ethyl]-2,3,4,9-tetrahydro-1H-carbazole-3-carboxamide | 131 | 418 | 418.4944 |

Example 19

The synthesis is carried out on a 0.2 mmol-scale according to instructions B, F, G and O.

| | | | |
|---|---|---|---|
| (3S)-2,3,4,9-Tetrahydro-3-[[(2S,3S)-3-methyl-1-oxo-2-[[(phenylmethoxy)carbonyl]amino]pentyl]amino]-1H-carbazole-3-carboxylic acid | 132 | 478 | 477.5579 |

Example 20

The synthesis is carried out on a 0.2 mmol-scale according to instructions B, F, G, F and O.

| | | | |
|---|---|---|---|
| (3S)-3-[[[(2,2-Diphenylethyl)amino]acetyl]amino]-2,3,4,9-tetrahydro-1H-carbazole-3-carboxylic acid | <u>134</u> | 468 | 467.5661 |

Example 21

The synthesis is carried out on a 0.2 mmol-scale according to instructions A, F, G, F, H and O.

| | | | |
|---|---|---|---|
| (3S)-3-(Acetylamino)-N-[[3-(aminocarbonyl)phenyl]-methyl]-2,3,4,9-tetrahydro-1H-carbazole-3-carboxamide | <u>135</u> | 404 | 404.4676 |
| (3S)-3-(Acetylamino)-N-[[4-(aminocarbonyl)cyclohexyl]-methyl]-2,3,4,9-tetrahydro-1H-carbazole-3-carboxamide | <u>136</u> | 410 | 410.515 |
| (3R)-3-(Acetylamino)-N-[[4-(aminocarbonyl)cyclohexyl]-methyl]-2,3,4,9-tetrahydro-1H-carbazole-3-carboxamide | <u>137</u> | 410 | 410.515 |
| (3S)-3-(Acetylamino)-N-[(1S)-2-amino-2-oxo-1-phenylethyl]-2,3,4,9-tetrahydro-1H-carbazole-3-carboxamide | <u>138</u> | 404 | 404.4676 |

Example 22

The synthesis is carried out on a 0.2 mmol-scale according to Examples 18 and 6.

| | | | |
|---|---|---|---|
| Phenylmethyl [(1S,2S)-1-[[[(3R)-3-[(ethylamino)carbonyl]-2,3,4,9-tetrahydro-1H-carbazol-3-yl]amino]carbonyl]-2-methylbutyl]carbamate | 139 | 505 | 504.6274 |
| Phenylmethyl [(1S,2S)-2-methyl-1-[[[(3R)-2,3,4,9-tetrahydro-3-[[(1-methylethyl)amino]-carbonyl]-1H-carbazol-3-yl]amino]carbonyl]-butyl]carbamate | 140 | 519 | 518.6542 |
| Phenylmethyl [(1S,2S)-2-methyl-1-[[[(3R)-2,3,4,9-tetrahydro-3-[[(2-methylpropyl)amino]-carbonyl]-1H-carbazol-3-yl]amino]carbonyl]-butyl]carbamate | 141 | 533 | 532.681 |
| Phenylmethyl [(1S,2S)-1-[[[(3R)-3-[[2,2-dimethylpropyl)amino]carbonyl]-2,3,4,9-tetrahydro-1H-carbazol-3-yl]amino]carbonyl]-2-methylbutyl]carbamate | 142 | 547 | 546.7078 |
| Phenylmethyl [(1S,2S)-2-methyl-1-[[[(3R)-2,3,4,9-tetrahydro-3-[(phenylamino)carbonyl]-1H-carbazol-3-yl]amino]carbonyl]butyl]-carbamate | 143 | 553 | 552.6714 |
| Phenylmethyl [(1S,2S)-2-methyl-1-[[[(3R)-2,3,4,9-tetrahydro-3-[[(phenylmethyl)amino]-carbonyl]-1H-carbazol-3-yl]amino]carbonyl]-butyl]carbamate | 144 | 567 | 566.6982 |
| Phenylmethyl [(1S,2S)-2-methyl-1-[[[(3R)-2,3,4,9-tetrahydro-3-[[(2-phenylethyl)amino]-carbonyl]-1H-carbazol-3-yl]amino]carbonyl]-butyl]carbamate | 145 | 581 | 580.725 |
| Phenylmethyl [(1S,2S)-2-methyl-1-[[[(3R)-2,3,4,9-tetrahydro-3-[[(3-phenylpropyl)amino]-carbonyl]-1H-carbazol-3-yl]amino]carbonyl]-butyl]carbamate | 146 | 595 | 594.7518 |

Example 23

The synthesis is carried out on a 0.2 mmol-scale according to instructions A, F, G, I, F, G and O.

| | | | |
|---|---|---|---|
| Phenylmethyl [(1S,2S)-1-[[[(3R)-3-[[[(1S)-1-(aminocarbonyl)-2-methypropyl]amino]-carbonyl]-2,3,4,9-tetrahydro-8-methoxy-1H-carbazol-3-yl]amino]carbonyl]-2-methylbutyl]carbamate | 147a | 606 | 605.7317 |
| Phenylmethyl [(1S,2S)-1-[[[(3S)-3-[[[(1S)-1-(aminocarbonyl)-2-methy-propyl]amino]-carbonyl]-2,3,4,9-tetrahydro-8-methoxy-1H-carbazol-3-yl]amino]carbonyl]-2-methylbutyl]carbamate | 147b | 606 | 605.7317 |
| Phenylmethyl [(1S,2S)-1-[[[(3R)-3-[[[(1S)-1-(aminocarbonyl)-2-methylpropyl]amino]-carbonyl]-6-chloro-2,3,4,9-tetrahydro-1H-carbazol-3-yl]amino]carbonyl]-2-methylbutyl]carbamate | 148a | 610 | 610.151 |
| Phenylmethyl [(1S,2S)-1-[[[(3S)-3-[[[(1S)-1-(aminocarbonyl)-2-methylpropyl]amino]-carbonyl]-6-chloro-2,3,4,9-tetrahydro-1H-carbazol-3-yl]amino]carbonyl]-2-methylbutyl]carbamate | 148b | 610 | 610.151 |
| Phenylmethyl [(1S,2S)-1-[[[(3R)-3-[[[(1S)-1-(aminocarbonyl)-2-methylpropyl]amino]-carbonyl]-8-chloro-2,3,4,9-tetrahydro-1H-carbazol-3-yl]amino]carbonyl]-2-methylbutyl]carbamate | 180a | 610 | 610.151 |
| Phenylmethyl [(1S,2S)-1-[[[(3S)-3-[[[(1S)-1-(aminocarbonyl)-2-methylpropyl]amino]-carbonyl]-8-chloro-2,3,4,9-tetrahydro-1H-carbazol-3-yl]amino]carbonyl]-2-methylbutyl]carbamate | 180b | 610 | 610.151 |
| Phenylmethyl [(1S,2S)-1-[[[(3R)-3-[[[(1S)-1-(aminocarbonyl)-2-methypropyl]amino]-carbonyl]-2,3,4,9-tetrahydro-8-(trifluoro-methyl)-1H-carbazol-3-yl]amino]carbonyl]-2-methylbutyl]carbamate | 149a | 644 | 643.703 |
| Phenylmethyl [(1S,2S)-1-[[[(3S)-3-[[[(1S)-1-(aminocarbonyl)-2-methylpropyl]amino]-carbonyl]-2,3,4,9-tetrahydro-8-(trifluoro-methyl)-1H-carbazol-3-yl]amino]carbonyl]-2-methylbutyl]carbamate | 149b | 644 | 643.703 |
| Phenylmethyl [(1S,2S)-1-[[[(3R)-3-[[[(1S)-1-(aminocarbonyl)-2-methylpropyl]amino]-carbonyl]-2,3,4,9-tetrahydro-8-methyl-1H-carbazol-3-yl]amino]carbonyl]-2-methylbutyl]carbamate | 150a | 590 | 589.7327 |
| Phenylmethyl [(1S,2S)-1-[[[(3S)-3-[[[(1S)-1-(aminocarbonyl)-2-methylpropyl]amino]-carbonyl]-2,3,4,9-tetrahydro-8-methyl-1H-carbazol-3-yl]amino]carbonyl]-2-methylbutyl]carbamate | 150b | 590 | 589.7327 |
| Phenylmethyl [(1S,2S)-1-[[[(3R)-3-[[[(1S)-1-(aminocarbonyl)-2-methylpropyl]amino]-carbonyl]-2,3,4,9-tetrahydro-5-methyl-1H-carbazol-3-yl]amino]carbonyl]-2-methylbutyl]carbamate | 151a | 590 | 589.7327 |
| Phenylmethyl [(1S,2S)-1-[[[(3S)-3-[[[(1S)-1-(aminocarbonyl)-2-methylpropyl]amino]-carbonyl]-2,3,4,9-tetrahydro-5-methyl-1H-carbazol-3-yl]amino]carbonyl]-2-methylbutyl]carbamate | 151b | 590 | 589.7327 |
| Phenylmethyl [(1S,2S)-1-[[[(3R)-3-[[[(1S)-1-(aminocarbonyl)-2-methylpropyl]amino]-carbonyl]-2,3,4,9-tetrahydro-7-methyl-1H-carbazol-3-yl]amino]carbonyl]-2-methylbutyl]carbamate | 151c | 590 | 589.7327 |
| Phenylmethyl [(1S,2S)-1-[[[(3S)-3-[[[(1S)-1-(aminocarbonyl)-2-methylpropyl]amino]-carbonyl]-2,3,4,9-tetrahydro-7-methyl-1H-carbazol-3-yl]amino]carbonyl]-2-methylbutyl]carbamate | 151d | 590 | 589.7327 |
| Phenylmethyl [(1S,2S)-1-[[[(3R)-3-[[[(1S)-1-(aminocarbonyl)-2-methylpropyl]amino]-carbonyl]-5-chloro-2,3,4,9-tetrahydro-1H-carbazol-3-yl]amino]carbonyl]-2-methylbutyl]carbamate | 152a | 610 | 610.151 |
| Phenylmethyl [(1S,2S)-1-[[[(3S)-3-[[[(1S)-1-(aminocarbonyl)-2-methylpropyl]amino]-carbonyl]-7-chloro-2,3,4,9-tetrahydro-1H-carbazol-3-yl]amino]carbonyl]-2-methylbutyl]carbamate | 152b | 610 | 610.151 |
| Phenylmethyl [(1S,2S)-1-[[[(3R)-3-[[[(1S)-1-(aminocarbonyl)-2-methy-propyl]amino]-carbonyl]-7-chloro-2,3,4,9-tetrahydro-1H-carbazol-3-yl]amino]carbonyl]-2-methylbutyl]carbamate | 152c | 610 | 610.151 |
| (3R)-3-[[[(1S)-1-(Aminocarbonyl)-2-methyl-propyl]-amino]carbonyl]-2,3,4,9-tetrahydro-3-[[(2S,3S)-3-methyl-1-oxo-2-[[(phenyl-methoxy)carbonyl]amino]pentyl]amino]-1H-carbazole-8-carboxylic acid | 153a | 620 | 619.7149 |
| (3S)-3-[[[(1S)-1-(Aminocarbonyl)-2-methyl-propyl]-amino]carbonyl]-2,3,4,9-tetrahydro-3-[[(2S,3S)-3-methyl-1-oxo-2-[[(phenyl-methoxy)carbonyl]amino]pentyl]amino]-1H-carbazole-8-carboxylic acid | 153b | 620 | 619.7149 |
| Phenylmethyl [(1S,2S)-1-[[[(3R)-3-[[[(1S)-1-(aminocarbonyl)-2-methylpropyl]amino]-carbonyl]-6-fluoro-2,3,4,9-tetrahydro-1H-carbazol-3-yl]amino]carbonyl]-2-methylbutyl]carbamate | 154a | 593 | 593.696 |
| Phenylmethyl [(1S,2S)-1-[[[(3S)-3-[[[(1S)-1-(aminocarbonyl)-2-methylpropyl]amino]-carbonyl]-6-fluoro-2,3,4,9-tetrahydro-1H-carbazol-3-yl]amino]carbonyl]-2-methylbutyl]carbamate | 154b | 593 | 593.696 |

| -continued | | | |
|---|---|---|---|
| Phenylmethyl [(1S,2S)-1-[[[(3R)-3-[[[(1S)-1-(aminocarbonyl)-2-methylpropyl]amino]carbonyl]-2,3,4,9-tetrahydro-6-methoxy-1H-carbazol-3-yl]amino]carbonyl]-2-methylbutyl]carbamate | 155a | 605 | 605.7317 |
| Phenylmethyl [(1S,2S)-1-[[[(3S)-3-[[[(1S)-1-(aminocarbonyl)-2-methylpropyl]amino]carbonyl]-2,3,4,9-tetrahydro-6-methoxy-1H-carbazol-3-yl]amino]carbonyl]-2-methylbutyl]carbamate | 155b | 605 | 605.7317 |
| Phenylmethyl [(1S,2S)-1-[[[(3R)-3-[[[(1S)-1-(aminocarbonyl)-2-methylpropyl]amino]carbonyl]-2,3,4,9-tetrahydro-6-methyl-1H-carbazol-3-yl]amino]carbonyl]-2-methylbutyl]carbamate | 156a | 589 | 589.7327 |
| Phenylmethyl [(1S,2S)-1-[[[(3S)-3-[[[(1S)-1-(aminocarbonyl)-2-methylpropyl]amino]carbonyl]-2,3,4,9-tetrahydro-6-methyl-1H-carbazol-3-yl]amino]carbonyl]-2-methylbutyl]carbamate | 156b | 589 | 589.7327 |
| Phenylmethyl [(1S,2S)-1-[[[(3R)-3-[[[(1S)-1-(aminocarbonyl)-2-methylpropyl]amino]carbonyl]-2,3,4,9-tetrahydro-6-nitro-1H-carbazol-3-yl]amino]carbonyl]-2-methylbutyl]carbamate | 157a | 621 | 620.703 |
| Phenylmethyl [(1S,2S)-1-[[[(3S)-3-[[[(1S)-1-(aminocarbonyl)-2-methylpropyl]amino]carbonyl]-2,3,4,9-tetrahydro-6-nitro-1H-carbazol-3-yl]amino]carbonyl]-2-methylbutyl]carbamate | 157b | 621 | 620.703 |
| Phenylmethyl [(1S,2S)-1-[[[(3R)-3-[[[(1S)-1-(aminocarbonyl)-4-[(aminoiminomethyl)amino]butyl]amino]carbonyl]-2,3,4,9-tetrahydro-1H-carbazol-3-yl]amino]carbonyl]-2-methylbutyl]carbamate | 158 | 633 | 632.7616 |
| (3R)-N-[(1S)-1-(Aminocarbonyl)-2-methylpropyl]-2,3,4,9-tetrahydro-3-[(3-pyridinylacetyl)amino]-1H-carbazole-3-carboxamide | 159a | 447 | 447.5361 |
| (3S)-N-[(1S)-1-(Aminocarbonyl)-2-methylpropyl]-2,3,4,9-tetrahydro-3-[(3-pyridinylacetyl)amino]-1H-carbazole-3-carboxamide | 159b | 447 | 447.5361 |
| (3R)-N-[(1S)-1-(Aminocarbonyl)-2-methylpropyl]-2,3,4,9-tetrahydro-3-[(1-naphthalenylacetyl)amino]-1H-carbazole-3-carboxamide | 160a | 496 | 496.6078 |
| (3S)-N-[(1S)-1-(Aminocarbonyl)-2-methylpropyl]-2,3,4,9-tetrahydro-3-[(1-naphthalenylacetyl)amino]-1H-carbazole-3-carboxamide | 160b | 496 | 496.6078 |
| (3R)-N-[(1S)-1-(Aminocarbonyl)-2-methylpropyl]-2,3,4,9-tetrahydro-3-[(2-naphthalenylacetyl)amino]-1H-carbazole-3-carboxamide | 161a | 496 | 496.6078 |
| (3S)-N-[(1S)-1-(Aminocarbonyl)-2-methylpropyl]-2,3,4,9-tetrahydro-3-[(2-naphthalenylacetyl)amino]-1H-carbazole-3-carboxamide | 161b | 496 | 496.6078 |
| (3R)-N-[(1S)-1-(Aminocarbonyl)-2-methylpropyl]-3-[[(2,3-dihydro-1H-inden-1-yl)carbonyl]amino]-2,3,4,9-tetrahydro-1H-carbazole-3-carboxamide | 162a | 472 | 472.5858 |
| (3S)-N-[(1S)-1-(Aminocarbonyl)-2-methylpropyl]-3-[[(2,3-dihydro-1H-inden-1-yl)carbonyl]amino]-2,3,4,9-tetrahydro-1H-carbazole-3-carboxamide | 162b | 472 | 472.5858 |
| (3R)-N-[(1S)-1-(Aminocarbonyl)-2-methylpropyl]-2,3,4,9-tetrahydro-3-[(1H-imidazol-4-ylacetyl)amino]-1H-carbazole-3-carboxamide | 163a | 436 | 436.5132 |
| (3S)-N-[(1S)-1-(Aminocarbonyl)-2-methylpropyl]-2,3,4,9-tetrahydro-3-[(1H-imidazol-4-ylacetyl)amino]-1H-carbazole-3-carboxamide | 163b | 436 | 436.5132 |
| (3R)-N-[(1S)-1-(Aminocarbonyl)-2-methylpropyl]-2,3,4,9-tetrahydro-3-[(1H-indol-3-ylacetyl)amino]-1H-carbazole-3-carboxamide | 164a | 486 | 485.5849 |
| (3S)-N-[(1S)-1-(Aminocarbonyl)-2-methylpropyl]-2,3,4,9-tetrahydro-3-[(1H-indol-3-ylacetyl)amino]-1H-carbazole-3-carboxamide | 164b | 486 | 485.5849 |
| (3R)-N-[(1S)-1-(Aminocarbonyl)-2-methylpropyl]-2,3,4,9-tetrahydro-3-[[(4-methylphenyl)acetyl]amino]-1H-carbazole-3-carboxamide | 165a | 461 | 460.5748 |
| (3S)-N-[(1S)-1-(Aminocarbonyl)-2-methylpropyl]-2,3,4,9-tetrahydro-3-[[(4-methylphenyl)acetyl]amino]-1H-carbazole-3-carboxamide | 165b | 461 | 460.5748 |
| (3R)-N-[(1S)-1-(Aminocarbonyl)-2-methylpropyl]-2,3,4,9-tetrahydro-3-[[[4-(trifluoromethyl)phenyl]acetyl]amino]-1H-carbazole-3-carboxamide | 166a | 515 | 514.5451 |
| (3S)-N-[(1S)-1-(Aminocarbonyl)-2-methylpropyl]-2,3,4,9-tetrahydro-3-[[[4-(trifluoromethyl)phenyl]acetyl]amino]-1H-carbazole-3-carboxamide | 166b | 515 | 514.5451 |
| (3R)-N-[(1S)-1-(Aminocarbonyl)-2-methylpropyl]-3-[[(4-chlorophenyl)acetyl]amino]-2,3,4,9-tetrahydro-1H-carbazole-3-carboxamide | 167a | 481 | 480.9931 |
| (3S)-N-[(1S)-1-(Aminocarbonyl)-2-methylpropyl]-3-[[(4-chlorophenyl)acetyl]amino]-2,3,4,9-tetrahydro-1H-carbazole-3-carboxamide | 167b | 481 | 480.9931 |
| (3S)-N-[(1S)-1-(Aminocarbonyl)-2-methylpropyl]-2,3,4,9-tetrahydro-3-[[[3-(trifluoromethyl)phenyl]acetyl]amino]-1H-carbazole-3-carboxamide | 168a | 515 | 514.5451 |
| (3R)-N-[(1S)-1-(Aminocarbonyl)-2-methylpropyl]-2,3,4,9-tetrahydro-3-[[[3-(trifluoromethyl)phenyl]acetyl]amino]-1H-carbazole-3-carboxamide | 168b | 515 | 514.5451 |
| (3R)-N-[(1S)-1-(Aminocarbonyl)-2-methylpropyl]-3-[[(3-fluorophenyl)acetyl]amino]-2,3,4,9-tetrahydro-1H-carbazole-3-carboxamide | 169a | 465 | 464.5381 |
| (3S)-N-[(1S)-1-(Aminocarbonyl)-2-methylpropyl]-3-[[(3-fluorophenyl)acetyl]amino]-2,3,4,9-tetrahydro-1H-carbazole-3-carboxamide | 169b | 465 | 464.5381 |
| (3R)-N-[(1S)-1-(Aminocarbonyl)-2-methylpropyl]-2,3,4,9-tetrahydro-3-[[(3-methoxyphenyl)acetyl]amino]-1H-carbazole-3-carboxamide | 170a | 477 | 476.5738 |
| (3S)-N-[(1S)-1-(Aminocarbonyl)-2-methylpropyl]-2,3,4,9-tetrahydro-3-[[(3-methoxyphenyl)acetyl]amino]-1H-carbazole-3-carboxamide | 170b | 477 | 476.5738 |
| (3R)-N-[(1S)-1-(Aminocarbonyl)-2-methylpropyl]-2,3,4,9-tetrahydro-3-[[(2-methoxyphenyl)acetyl]amino]1H-carbazole-3-carboxamide- | 171a | 477 | 476.5738 |
| (3S)-N-[(1S)-1-(Aminocarbonyl)-2-methylpropyl]-2,3,4,9-tetrahydro-3-[[(2-methoxyphenyl)acetyl]amino]1H-carbazole-3-carboxamide- | 171b | 477 | 476.5738 |
| (3R)-N-[(1S)-1-(Aminocarbonyl)-2-methylpropyl]-3-[[3-(4-fluorophenyl)-1-oxopropyl]amino]-2,3,4,9-tetrahydro-1H-carbazole-3-carboxamide | 172a | 479 | 478.5649 |
| (3S)-N-[(1S)-1-(Aminocarbonyl)-2-methylpropyl]-3-[[3-(4-fluorophenyl)-1-oxopropyl]amino]-2,3,4,9-tetrahydro-1H-carbazole-3-carboxamide | 172b | 479 | 478.5649 |
| (3R)-N-[(1S)-1-(Aminocarbonyl)-2-methylpropyl]-3-[[3-(3,4-difluorophenyl)-1-oxopropyl]amino]-2,3,4,9-tetrahydro-1H-carbazole-3-carboxamide | 173a | 497 | 496.555 |
| (3S)-N-[(1S)-1-(Aminocarbonyl)-2-methylpropyl]-3-[[3-(3,4-difluorophenyl)-1-oxopropyl]amino]-2,3,4,9-tetrahydro-1H-carbazole-3-carboxamide | 173b | 497 | 496.555 |
| (3R)-N-[(1S)-1-(Aminocarbonyl)-2-methylpropyl]-3-[[3-[3,4-bis(trifluoromethyl)phenyl]-1-oxopropyl]amino]-2,3,4,9-tetrahydro-1H-carbazole-3-carboxamide | 174a | 593 | 592.6057 |
| (3S)-N-[(1S)-1-(Aminocarbonyl)-2-methylpropyl]-3-[[3-[3,4-bis(trifluoromethyl)phenyl]-1-oxopropyl]amino]-2,3,4,9-tetrahydro-1H-carbazole-3-carboxamide | 174b | 593 | 592.6057 |
| N-[(1S)-1-(Aminocarbonyl)-2-methylpropyl]-2,3,4,9-tetrahydro-3-[[(4-methoxyphenyl)acetyl]amino]-1H-carbazole-3-carboxamide | 175 | 477 | 476.5738 |
| (3R)-N-[(1S)-1-(Aminocarbonyl)-2-methylpropyl]-2,3,4,9-tetrahydro-3-[[3-(4-methoxyphenyl)-1-oxopropyl]amino]-1H-carbazole-3-carboxamide | 176a | 491 | 490.6006 |

-continued

| | | | |
|---|---|---|---|
| (3S)-N-[(1S)-1-(Aminocarbonyl)-2-methyl-propyl]-2,3,4,9-tetrahydro-3-[[3-(4-methoxy-phenyl)-1-oxopropyl]amino]-1H-carbazole-3-carboxamide | 176b | 491 | 490.6006 |
| (3R)-N-[(1S)-1-(Aminocarbonyl)-2-methyl-propyl]-2,3,4,9-tetrahydro-3-[[3-(2-methoxy-phenyl)-1-oxopropyl]amino]-1H-carbazole-3-carboxamide | 177a | 491 | 490.6006 |
| (3S)-N-[(1S)-1-(Aminocarbonyl)-2-methyl-propyl]-2,3,4,9-tetrahydro-3-[[3-(2-methoxy-phenyl)-1-oxopropyl]amino]-1H-carbazole-3-carboxamide | 177b | 491 | 490.6006 |
| (3R)-N-[(1S)-1-(Aminocarbonyl)-2-methyl-propyl]-2,3,4,9-tetrahydro-3-[[3-(1H-indol-3-yl)-1-oxopropyl]amino]-1H-carbazole-3-carboxamide | 178a | 500 | 499.6117 |
| (3S)-N-[(1S)-1-(Aminocarbonyl)-2-methyl-propyl]-2,3,4,9-tetrahydro-3-[[3-(1H-indol-3-yl)-1-oxopropyl]amino]-1H-carbazole-3-carboxamide | 178b | 500 | 499.6117 |
| (3R)-N-[(1S)-1-(Aminocarbonyl)-2-methyl-propyl]-2,3,4,9-tetrahydro-3-[(1-oxo-6-phenyl-hexyl)amino]-1H-carbazole-3-carboxamide | 179a | 503 | 502.6552 |
| (3S)-N-[(1S)-1-(Aminocarbonyl)-2-methyl-propyl]-2,3,4,9-tetrahydro-3-[(1-oxo-6-phenyl-hexyl)amino]-1H-carbazole-3-carboxamide | 179b | 503 | 502.6552 |
| Phenylmethyl [(1S,2S)-1-[[[(3R)-3-[[(2S)-2-(aminocarbonyl)-1-pyrrolidinyl]carbonyl]-2,3,4,9-tetrahydro-1H-carbazol-3-yl]amino]-carbonyl]-2-methylbutyl]carbamate | 181a | 574 | 573.6901 |
| Phenylmethyl [(1S,2S)-1-[[[(3S)-3-[[(2S)-2-(aminocarbonyl)-1-pyrrolidinyl]carbonyl]-2,3,4,9-tetrahydro-1H-carbazol-3-yl]amino]-carbonyl]-2-methylbutyl]carbamate | 181b | 574 | 573.6901 |
| Phenylmethyl [(1S,2S)-1-[[[(3R)-3-[[[(1S)-1-(aminocarbonyl)-2-methylpropyl]amino]-carbonyl]-7,8-dichloro-2,3,4,9-tetrahydro-1H-carbazol-3-yl]amino]-carbonyl]-2-methylbutyl]-carbamate | 182a | 645 | 644.5961 |
| Phenylmethyl [(1S,2S)-1-[[[(3S)-3-[[[(1S)-1-(aminocarbonyl)-2-methylpropyl]amino]-carbonyl]-7,8-dichloro-2,3,4,9-tetrahydro-1H-carbazol-3-yl]amino]-carbonyl]-2-methylbutyl]-carbamate | 182b | 645 | 644.5961 |
| Phenylmethyl [(1S,2S)-1-[[[(3R)-3-[[[(1S)-1-(aminocarbonyl)-2-methylpropyl]amino]-carbonyl]-2,3,4,9-tetrahydro-5,8-dimethyl-1H-carbazol-3-yl]amino]-carbonyl]-2-methylbutyl]-carbamate | 183a | 604 | 603.7595 |
| Phenylmethyl [(1S,2S)-1-[[[(3S)-3-[[[(1S)-1-(aminocarbonyl)-2-methylpropyl]amino]-carbonyl]-2,3,4,9-tetrahydro-5,8-dimethyl-1H-carbazol-3-yl]amino]-carbonyl]-2-methylbutyl]-carbamate | 183b | 604 | 603.7595 |
| Phenylmethyl [(1S,2S)-1-[[[(3R)-3-[[[(1S)-1-(aminocarbonyl)-2-methylpropyl]amino]-carbonyl]-6,8-dichloro-2,3,4,9-tetrahydro-1H-carbazol-3-yl]amino]-carbonyl]-2-methylbutyl]-carbamate | 184a | 645 | 644.5961 |
| Phenylmethyl [(1S,2S)-1-[[[(3S)-3-[[[(1S)-1-(aminocarbonyl)-2-methylpropyl]amino]-carbonyl]-6,8-dichloro-2,3,4,9-tetrahydro-1H-carbazol-3-yl]amino]-carbonyl]-2-methylbutyl]-carbamate | 184b | 645 | 644.5961 |
| Phenylmethyl [(1S,2S)-1-[[[(3R)-3-[[[(1S)-1-(aminocarbonyl)-2-methylpropyl]amino]-carbonyl]-6-bromo-2,3,4,9-tetrahydro-1H-carbazol-3-yl]amino]-carbonyl]-2-methylbutyl]-carbamate | 185a | 655 | 654.602 |
| Phenylmethyl [(1S,2S)-1-[[[(3S)-3-[[[(1S)-1-(aminocarbonyl)-2-methylpropyl]amino]-carbonyl]-6-bromo-2,3,4,9-tetrahydro-1H-carbazol-3-yl]amino]-carbonyl]-2-methylbutyl]-carbamate | 185b | 655 | 654.602 |
| (3R)-N-[(1S)-1-(Aminocarbonyl)-2-methyl-propyl]-3-[[(4-chlorophenyl)acetyl]amino]-2,3,4,9-tetrahydro-8-methoxy-1H-carbazole-3-carboxamide | 186a | 511 | 511.0189 |
| (3S)-N-[(1S)-1-(Aminocarbonyl)-2-methyl-propyl]-3-[[(4-chlorophenyl)acetyl]amino]-2,3,4,9-tetrahydro-8-methoxy-1H-carbazole-3-carboxamide | 186b | 511 | 511.0189 |
| Phenylmethyl [(1S,2S)-1-[[[(3R)-3-[[[(1R)-2-amino-1-[(4-chlorophenyl)methyl]-2-oxoethyl]-amino]carbonyl]-2,3,4,9-tetrahydro-1H-carbazol-3-yl]amino]carbonyl]-2-methylbutyl]-carbamate | 187a | 658 | 658.195 |
| Phenylmethyl [(1S,2S)-1-[[[(3S)-3-[[[(1R)-2-amino-1-[(4-chlorophenyl)methyl]-2-oxoethyl]-amino]carbonyl]-2,3,4,9-tetrahydro-1H-carbazol-3-yl]amino]carbonyl]-2-methylbutyl]-carbamate | 187b | 658 | 658.195 |
| Phenylmethyl [(1S,2S)-1-[[[3-[[(3-amino-3-oxopropyl)amino]carbonyl]-2,3,4,9-tetrahydro-1H-carbazol-3-yl]amino]carbonyl]-2-methyl-butyl]carbamate | 188 | 548 | 547.6523 |
| (2S)-1-[[(3R)-3-[[(4-Chlorophenyl)acetyl]-amino]-2,3,4,9-tetrahydro-8-methoxy-1H-carbazol-3-yl]carbonyl]-2-pyrrolidine-carboxamide | 189a | 509 | 509.0031 |
| (2S)-1-[[(3S)-3-[[(4-Chlorophenyl)acetyl]-amino]-2,3,4,9-tetrahydro-8-methoxy-1H-carbazol-3-yl]carbonyl]-2-pyrrolidine-carboxamide | 189b | 509 | 509.0031 |
| Phenylmethyl [(1S,2S)-1-[[[(3R)-3-[[(2S)-2-(aminocarbonyl)octahydro-1H-indol-1-yl]-carbonyl]-2,3,4,9-tetrahydro-1H-carbazol-3-yl]-amino]carbonyl]-2-methylbutyl]carbamate | 190a | 628 | 627.7815 |
| Phenylmethyl [(1S,2S)-1-[[[(3S)-3-[[(2S)-2-(aminocarbonyl)octahydro-1H-indol-1-yl]-carbonyl]-2,3,4,9-tetrahydro-1H-carbazol-3-yl]-amino]carbonyl]-2-methylbutyl]carbamate | 190b | 628 | 627.7815 |
| Phenylmethyl [(1S,2S)-1-[[[(3R)-3-[[(2S,4R)-2-(aminocarbonyl)-4-hydroxy-1-pyrrolidinyl]-carbonyl]-2,3,4,9-tetrahydro-1H-carbazol-3-yl]-amino]carbonyl]-2-methylbutyl]carbamate | 191a | 590 | 589.6891 |
| Phenylmethyl [(1S,2S)-1-[[[(3S)-3-[[(2S,4R)-2-(aminocarbonyl)-4-hydroxy-1-pyrrolidinyl]-carbonyl]-2,3,4,9-tetrahydro-1H-carbazol-3-yl]-amino]carbonyl]-2-methylbutyl]carbamate | 191b | 590 | 589.6891 |
| Phenylmethyl [(1S,2S)-1-[[[(3R)-3-[[[(1S,2R)-1-(aminocarbonyl)-2-hydroxypropyl]amino]-carbonyl]-2,3,4,9-tetrahydro-1H-carbazol-3-yl]-amino]carbonyl]-2-methylbutyl]carbamate | 291a | 578 | 577.6781 |
| Phenylmethyl [(1S,2S)-1-[[[(3S)-3-[[[(1S,2R)-1-(aminocarbonyl)-2-hydroxypropyl]amino]-carbonyl]-2,3,4,9-tetrahydro-1H-carbazol-3-yl]-amino]carbonyl]-2-methylbutyl]carbamate | 291b | 578 | 577.6781 |
| Phenylmethyl [(1S,2S)-1-[[[(3S)-3-[[(2-amino-2-oxoethyl)amino]carbonyl]-2,3,4,9-tetrahydro-1H-carbazol-3-yl]amino]carbonyl]-2-methyl-butyl]carbamate | 292 | 534 | 533.6255 |
| Phenylmethyl [(1S,2S)-1-[[[3-[[[2-(amino-carbonyl)phenyl]-amino]carbonyl]-2,3,4,9-tetrahydro-1H-carbazol-3-yl]amino]carbonyl]-2-methylbutyl]carbamate | 192 | 596 | 595.6963 |
| (3R)-N-[(1S)-1-(Aminocarbonyl)-2-methyl-propyl]-3-[[[4-chloro-3-[[(4-pyridinyl-amino)-carbonyl]amino]phenyl]-acetyl]amino]-2,3,4,9-tetrahydro-1H-carbazole-3-carboxamide | 193a | 616 | 616.119 |
| (3S)-N-[(1S)-1-(Aminocarbonyl)-2-methyl-propyl]-3-[[[4-chloro-3-[[(4-pyridinyl-amino)carbonyl]amino-phenyl]-acetyl]amino]-2,3,4,9-tetrahydro-1H-carbazole-3-carboxamide | 193b | 616 | 616.119 |
| (3R)-N-[(1S)-1-(Aminocarbonyl)-2-methyl-propyl]-3-[[[4-chloro-3-[[(phenylamino)-carbonyl]amino]phenyl]-acetyl]amino]-2,3,4,9-tetrahydro-1H-carbazole-3-carboxamide | 194a | 615 | 615.13 |
| (3S)-N-[(1S)-1-(Aminocarbonyl)-2-methyl-propyl]-3-[[[4-chloro-3-[[(phenylamino)-carbonyl]amino]phenyl]acetyl]-amino]-2,3,4,9-tetrahydro-1H-carbazole-3-carboxamide | 194b | 615 | 615.13 |
| (3R)-N-[(1S)-1-(Aminocarbonyl)-2-methyl-propyl]-3-[[[4-chloro-3-[[[(phenylmethyl)-amino]-carbonyl]amino]phenyl]-acetyl]amino]-2,3,4,9-tetrahydro-1H-carbazole-3-carboxamide | 195a | 629 | 629.157 |

| | | | |
|---|---|---|---|
| (3S)-N-[(1S)-1-(Aminocarbonyl)-2-methyl-propyl]-3-[[[4-chloro-3-[[[(phenylmethyl)-amino]carbonyl]amino]-phenyl]acetyl]amino]-2,3,4,9-tetrahydro-1H-carbazole-3-carboxamide | 195b | 629 | 629.157 |
| (3R)-N-[(1S)-1-(Aminocarbonyl)-2-methyl-propyl]-3-[[[4-chloro-3-[[(2-pyridinyl-amino)carbonyl]amino]phenyl]acetyl]amino]-2,3,4,9-tetrahydro-1H-carbazole-3-carboxamide | 196a | 616 | 616.119 |
| (3S)-N-[(1S)-1-(Aminocarbonyl)-2-methyl-propyl]-3-[[[4-chloro-3-[[(2-pyridinyl-amino)carbonyl]amino]phenyl]-acetyl]-amino]-2,3,4,9-tetrahydro-1H-carbazole-3-carboxamide | 196b | 616 | 616.119 |

Example 24

The synthesis is carried out on a 0.2 mmol-scale according to instructions A, F, G, I, F, H and O.

| | | | |
|---|---|---|---|
| (3R)-3-(Acetylamino)-N-[(1S)-1-(aminocarbonyl)-2-methylpropyl]-2,3,4,9-tetrahydro-8-methoxy-1H-carbazole-methylpropyl]-2,3,4,9-tetrahydro-8-methoxy-1H-carbazole-3-carboxamide | 197a | 400 | 400.4762 |
| (3S)-3-(Acetylamino)-N-[(1S)-1-(aminocarbonyl)-2-methylpropyl]-2,3,4,9-tetrahydro-8-methoxy-1H-carbazole-3-carboxamide | 197b | 400 | 400.4762 |
| 3-(Acetylamino)-N-[(1S)-1-(aminocarbonyl)-2-methylpropyl]-6-chloro-2,3,4,9-tetrahydro-1H-carbazole-3-carboxamide | 198 | 405 | 404.8955 |
| 3-(Acetylamino)-N-[(1S)-1-(aminocarbonyl)-2-methylpropyl]-2,3,4,9-tetrahydro-5-methyl-1H-carbazole-3-carboxamide | 199 | 769 | 768.9544 |
| 3-(Acetylamino)-N-[(1S)-1-(aminocarbonyl)-2-methylpropyl]-2,3,4,9-tetrahydro-8-methyl-1H-carbazole-3-carboxamide | 200 | 769 | 768.9544 |
| 3-(Acetylamino)-N-[(1S)-1-(aminocarbonyl)-2-methylpropyl]-5-chloro-2,3,4,9-tetrahydro-1H-carbazole-3-carboxamide | 201 | 810 | 809.7911 |
| 3-(Acetylamino)-N-[(1S)-1-(aminocarbonyl)-2-methylpropyl]-7-chloro-2,3,4,9-tetrahydro-1H-carbazole-3-carboxamide | 202 | 810 | 809.7911 |
| (3R)-3-(Acetylamino)-N-[(1S)-1-(aminocarbonyl)-2-methylpropyl]-6-fluoro-2,3,4,9-tetrahydro-1H-carbazole-3-carboxamide | 203a | 388 | 388.4405 |
| (3S)-3-(Acetylamino)-N-[(1S)-1-(aminocarbonyl)-2-methylpropyl]-6-fluoro-2,3,4,9-tetrahydro-1H-carbazole-3-carboxamide | 203b | 388 | 388.4405 |
| (3R)-3-(Acetylamino)-N-[(1S)-1-(aminocarbonyl)-2-methylpropyl]-2,3,4,9-tetrahydro-6-methoxy-1H-carbazole-3-carboxamide | 204a | 400 | 400.4762 |
| (3S)-3-(Acetylamino)-N-[(1S)-1-(aminocarbonyl)-2-methylpropyl]-2,3,4,9-tetrahydro-6-methoxy-1H-carbazole-3-carboxamide | 204b | 400 | 400.4762 |
| (3R)-3-(Acetylamino)-N-[(1S)-1-(aminocarbonyl)-2-methylpropyl]-2,3,4,9-tetrahydro-6-methyl-1H-carbazole-3-carboxamide | 205a | 384 | 384.4772 |
| (3S)-3-(Acetylamino)-N-[(1S)-1-(aminocarbonyl)-2-methylpropyl]-2,3,4,9-tetrahydro-6-methyl-1H-carbazole-3-carboxamide | 205b | 384 | 384.4772 |
| (3R)-3-(Acetylamino)-N-[(1S)-1-(aminocarbonyl)-2-methylpropyl]-2,3,4,9-tetrahydro-1H-carbazole-3-carboxamide | 206a | 370 | 370.4504 |
| (3S)-3-(Acetylamino)-N-[(1S)-1-(aminocarbonyl)-2-methylpropyl]-2,3,4,9-tetrahydro-1H-carbazole-3-carboxamide | 206b | 370 | 370.4504 |
| (3R)-3-(Acetylamino)-N-[(1S)-1-(aminocarbonyl)-2-methylpropyl]-7,8-dichloro-2,3,4,9-tetrahydro-1H-carbazole-3-carboxamide | 207a | 439 | 439.3406 |
| (3S)-3-(Acetylamino)-N-[(1S)-1-(aminocarbonyl)-2-methylpropyl]-7,8-dichloro-2,3,4,9-tetrahydro-1H-carbazole-3-carboxamide | 207b | 439 | 439.3406 |
| (3R)-3-(Acetylamino)-N-[(1S)-1-(aminocarbonyl)-2-methylpropyl]-2,3,4,9-tetrahydro-5,8-dimethyl-1H-carbazole-3-carboxamide | 208a | 399 | 398.504 |
| (3S)-3-(Acetylamino)-N-[(1S)-1-(aminocarbonyl)-2-methylpropyl]-2,3,4,9-tetrahydro-5,8-dimethyl-1H-carbazole-3-carboxamide | 208b | 399 | 398.504 |
| (3R)-3-(Acetylamino)-N-[(1S)-1-(aminocarbonyl)-2-methylpropyl]-6,8-dichloro-2,3,4,9-tetrahydro-1H-carbazole-3-carboxamide | 209a | 439 | 439.3406 |
| (3S)-3-(Acetylamino)-N-[(1S)-1-(aminocarbonyl)-2-methylpropyl]-6,8-dichloro-2,3,4,9-tetrahydro-1H-carbazole-3-carboxamide | 209b | 439 | 439.3406 |

Example 25

The synthesis is carried out on a 0.2 mmol-scale according to instructions A, F, G, I, F, G, F and O.

| | | | |
|---|---|---|---|
| (3R)-3-[[(2S)-2-Amino-5-[(aminoiminomethyl)amino]-1-oxopentyl]amino]-N-[(1S)-1-(aminocarbonyl)-2-methylpropyl]-2,3,4,9-tetrahydro-1H-carbazole-3-carboxamide | 210a | 485 | 484.6014 |
| (3S)-3-[[(2S)-2-Amino-5-[(aminoiminomethyl)amino]-1-oxopentyl]amino]-N-[(1S)-1-(aminocarbonyl)-2-methylpropyl]-2,3,4,9-tetrahydro-1H-carbazole-3-carboxamide | 210b | 485 | 484.6014 |
| (3R)-N-[(1S)-1-(Aminocarbonyl)-2-methyl-propyl]-2,3,4,9-tetrahydro-3-[[[[2-(1-piperidin-yl)ethyl]amino]acetyl]amino]-1H-carbazole-3-carboxamide | 211a | 497 | 496.652 |
| (3S)-N-[(1S)-1-(Aminocarbonyl)-2-methyl-propyl]-2,3,4,9-tetrahydro-3-[[[[2-(1-piperidin-yl)ethyl]amino]acetyl]amino]-1H-carbazole-3-carboxamide | 211b | 497 | 496.652 |
| (3R)-N-[(1S)-1-(Aminocarbonyl)-2-methyl-propyl]-2,3,4,9-tetrahydro-3-[[[[2-(1H-indol-3-yl)ethyl]amino]acetyl]amino]-1H-carbazole-3-carboxamide | 212a | 529 | 528.6534 |
| (3S)-N-[(1S)-1-(Aminocarbonyl)-2-methylprop-yl]-2,3,4,9-tetrahydro-3-[[[[2-(1H-indol-3-yl)-ethyl]amino]acetyl]amino]-1H-carbazole-3-carboxamide | 212b | 529 | 528.6534 |
| (3R)-N-[(1S)-1-(Aminocarbonyl)-2-methyl-propyl]-3-[[[(1,3-benzodioxol-5-ylmethyl)-amino]acetyl]amino]-2,3,4,9-tetrahydro-1H-carbazole-3-carboxamide | 213a | 520 | 519.5987 |
| (3S)-N-[(1S)-1-(Aminocarbonyl)-2-methylprop-yl]-3-[[[(1,3-benzodioxol-5-ylmethyl)amino]-acetyl]amino]-2,3,4,9-tetrahydro-1H-carbazole-3-carboxamide | 213b | 520 | 519.5987 |
| (3R)-N-[(1S)-1-(Aminocarbonyl)-2-methyl-propyl]-3-[[[(2,2-diphenylethyl)amino]-acetyl]amino]-2,3,4,9-tetrahydro-1H-carbazole-3-carboxamide | 214a | 566 | 565.7141 |
| (3S)-N-[(1S)-1-(Aminocarbonyl)-2-methyl-propyl]-3-[[[(2,2-diphenylethyl)amino]-acetyl]amino]-2,3,4,9-tetrahydro-1H-carbazole-3-carboxamide | 214b | 566 | 565.7141 |
| (3R)-N-[(1S)-1-(Aminocarbonyl)-2-methyl-propyl]-2,3,4,9-tetrahydro-3-[[[[2-[methyl-(phenylmethyl)amino]ethyl]amino]acetyl]-amino]-1H-carbazole-3-carboxamide | 215a | 533 | 532.685 |
| (3S)-N-[(1S)-1-(Aminocarbonyl)-2-methylprop-yl]-2,3,4,9-tetrahydro-3-[[[[2-[methyl-(phenylmethyl)amino]ethyl]amino]acetyl]-amino]-1H-carbazole-3-carboxamide | 215b | 533 | 532.685 |

Example 26

The synthesis is carried out on a 0.2 mmol-scale according to instructions A, F, G, I, F, G, F, H and O.

| | | | |
|---|---|---|---|
| 3-[[[Acetyl[2-(1-piperidinyl)ethyl]amino]acetyl]amino]-N-[(1S)-1-(aminocarbonyl)-2-methylpropyl]-2,3,4,9-tetrahydro-1H-carbazole-3-carboxamide | 216 | 539 | 538.6888 |
| (3R)-3-[[[Acetyl[2-[methyl(phenylmethyl)amino]ethyl]amino]acetyl]amino]-N-[(1S)-1-(aminocarbonyl)-2-methylpropyl]-2,3,4,9-tetrahydro-1H-carbazole-3-carboxamide | 217a | 575 | 574.7217 |
| (3S)-3-[[[Acetyl[2-[methyl(phenylmethyl)amino]ethyl]amino]acetyl]amino]-N-[(1S)-1-(aminocarbonyl)-2-methylpropyl]-2,3,4,9-tetrahydro-1H-carbazole-3-carboxamide | 217b | 575 | 574.7217 |
| (3R)-3-[[[Acetyl(2,2-diphenylethyl)amino]acetyl]amino]-N-[(1S)-1-(aminocarbonyl)-2-methylpropyl]-2,3,4,9-tetrahydro-1H-carbazole-3-carboxamide | 218a | 608 | 607.7509 |
| (3S)-3-[[[Acetyl(2,2-diphenylethyl)amino]acetyl]amino]-N-[(1S)-1-(aminocarbonyl)-2-methylpropyl]-2,3,4,9-tetrahydro-1H-carbazole-3-carboxamide | 218b | 608 | 607.7509 |
| (3R)-3-[[[Acetyl(1,3-benzodioxol-5-ylmethyl)amino]acetyl]-amino]-N-[(1S)-1-(aminocarbonyl)-2-methylpropyl]-2,3,4,9-tetrahydro-1H-carbazole-3-carboxamide | 219a | 562 | 561.6355 |
| (3S)-3-[[[Acetyl(1,3-benzodioxol-5-ylmethyl)amino]acetyl]-amino]-N-[(1S)-1-(aminocarbonyl)-2-methylpropyl]-2,3,4,9-tetrahydro-1H-carbazole-3-carboxamide | 219b | 562 | 561.6355 |
| (3R)-3-[[[Acetyl[2-(1H-indol-3-yl)ethyl]amino]acetyl]-amino]-N-[(1S)-1-(aminocarbonyl)-2-methylpropyl]-2,3,4,9-tetrahydro-1H-carbazole-3-carboxamide | 220a | 571 | 570.6902 |
| (3S)-3-[[[Acetyl[2-(1H-indol-3-yl)ethyl]amino]acetyl]-amino]-N-[(1S)-1-(aminocarbonyl)-2-methylpropyl]-2,3,4,9-tetrahydro-1H-carbazole-3-carboxamide | 220b | 571 | 570.6902 |
| 3-[[(2S)-2-(Acetylamino)-5-[(aminoiminomethyl)amino]-1-oxopentyl]amino]-N-[(1S)-1-(aminocarbonyl)-2-methylpropyl]-2,3,4,9-tetrahydro-1H-carbazole-3-carboxamide | 221 | 527 | 526.6382 |

Example 27

The synthesis is carried out on a 0.2 mmol-scale according to instructions C, F, G, I, F, G and P.

| | | | |
|---|---|---|---|
| Phenylmethyl [(1S,2S)-2-methyl-1-[[[(3R)-2,3,4,9-tetrahydro-3-[[[(1S)-2-methyl-1-[(methylamino)carbonyl]-propyl]amino]carbonyl]-1H-carbazol-3-yl]amino]carbonyl]-butyl]carbamate | 222a | 589 | 589.7327 |
| Phenylmethyl [(1S,2S)-2-methyl-1-[[[(3S)-2,3,4,9-tetrahydro-3-[[[(1S)-2-methyl-1-[(methylamino)carbonyl]-propyl]amino]carbonyl]-1H-carbazol-3-yl]amino]-carbonyl]butyl]carbamate | 222b | 589 | 589.7327 |

Example 28

The synthesis is carried out on a 0.2 mmol-scale according to instructions A, F, G, I, F, J and O.

| | | | |
|---|---|---|---|
| (3R)-N-[(1S)-1-(Aminocarbonyl)-2-methylpropyl]-3-[[(4-chlorophenyl)sulfonyl]amino]-2,3,4,9-tetrahydro-1H-carbazole-3-carboxamide | 223a | 503 | 503.0203 |
| (3S)-N-[(1S)-1-(Aminocarbonyl)-2-methylpropyl]-3-[[(4-chlorophenyl)sulfonyl]amino]-2,3,4,9-tetrahydro-1H-carbazole-3-carboxamide | 223b | 503 | 503.0203 |
| (3R)-N-[(1S)-1-(Aminocarbonyl)-2-methylpropyl]-2,3,4,9-tetrahydro-3-[(methylsulfonyl)amino]-1H-carbazole-3-carboxamide | 224a | 407 | 406.5044 |
| (3S)-N-[(1S)-1-(Aminocarbonyl)-2-methylpropyl]-2,3,4,9-tetrahydro-3-[(methylsulfonyl)amino]-1H-carbazole-3-carboxamide | 224b | 407 | 406.5044 |
| (3R)-N-[(1S)-1-(Aminocarbonyl)-2-methylpropyl]-2,3,4,9-tetrahydro-3-[(phenylsulfonyl)amino]-1H-carbazole-3-carboxamide | 225a | 469 | 468.5752 |
| (3S)-N-[(1S)-1-(Aminocarbonyl)-2-methylpropyl]-2,3,4,9-tetrahydro-3-[(phenylsulfonyl)amino]-1H-carbazole-3-carboxamide | 225b | 469 | 468.5752 |
| (3R)-N-[(1S)-1-(Aminocarbonyl)-2-methylpropyl]-2,3,4,9-tetrahydro-3-[[(phenylmethyl)sulfonyl]amino]-1H-carbazole-3-carboxamide | 226a | 483 | 482.602 |
| (3S)-N-[(1S)-1-(Aminocarbonyl)-2-methylpropyl]-2,3,4,9-tetrahydro-3-[[(phenylmethyl)sulfonyl]amino]-1H-carbazole-3-carboxamide | 226b | 483 | 482.602 |

Example 29

The synthesis is carried out on a 0.2 mmol-scale according to instructions A, F, G, I, F, L and O.

| | | | |
|---|---|---|---|
| 3-Phenylpropyl [(3R)-3-[[[(1S)-1-(aminocarbonyl)-2-methylpropyl]amino]carbonyl]-2,3,4,9-tetrahydro-1H-carbazol-3-yl]carbamate | 227a | 491 | 490.6006 |
| 3-Phenylpropyl [(3S)-3-[[[(1S)-1-(aminocarbonyl)-2-methylpropyl]amino]carbonyl]-2,3,4,9-tetrahydro-1H-carbazol-3-yl]carbamate | 227b | 491 | 490.6006 |
| Phenylmethyl [(3R)-3-[[[(1S)-1-(aminocarbonyl)-2-methylpropyl]amino]carbonyl]-2,3,4,9-tetrahydro-1H-carbazol-3-yl]carbamate | 228a | 463 | 462.547 |
| Phenylmethyl [(3S)-3-[[[(1S)-1-(aminocarbonyl)-2-methylpropyl]amino]carbonyl]-2,3,4,9-tetrahydro-1H-carbazol-3-yl]carbamate | 228b | 463 | 462.547 |
| Phenyl [(3R)-3-[[[(1S)-1-(aminocarbonyl)-2-methylpropyl]amino]carbonyl]-2,3,4,9-tetrahydro-1H-carbazol-3-yl]carbamate | 229a | 449 | 448.5202 |
| Phenyl [(3S)-3-[[[(1S)-1-(aminocarbonyl)-2-methylpropyl]amino]carbonyl]-2,3,4,9-tetrahydro-1H-carbazol-3-yl]carbamate | 229b | 449 | 448.5202 |

Example 30

The synthesis is carried out on a 0.2 mmol-scale according to instructions A, F, G, I, F, M and O.

| Compound | No. | MW | Mass |
|---|---|---|---|
| (3R)-N-[(1S)-1-(Aminocarbonyl)-2-methylpropyl]-2,3,4,9-tetrahydro-3-[[(4-nitrophenyl)methyl]amino]-1H-carbazole-3-carboxamide | 230a | 464 | 463.5351 |
| (3S)-N-[(1S)-1-(Aminocarbonyl)-2-methylpropyl]-2,3,4,9-tetrahydro-3-[[(4-nitrophenyl)methyl]amino]-1H-carbazole-3-carboxamide | 230b | 464 | 463.5351 |
| (3R)-N-[(1S)-1-(Aminocarbonyl)-2-methylpropyl]-3-(ethylamino)-2,3,4,9-tetrahydro-1H-carbazole-3-carboxamide | 231a | 356 | 356.4672 |
| (3S)-N-[(1S)-1-(Aminocarbonyl)-2-methylpropyl]-3-(ethylamino)-2,3,4,9-tetrahydro-1H-carbazole-3-carboxamide | 231b | 356 | 356.4672 |
| (3R)-N-[(1S)-1-(Aminocarbonyl)-2-methylpropyl]-2,3,4,9-tetrahydro-3-[(2-phenylethyl)amino]-1H-carbazole-3-carboxamide | 232a | 433 | 432.5648 |
| (3S)-N-[(1S)-1-(Aminocarbonyl)-2-methylpropyl]-2,3,4,9-tetrahydro-3-[(2-phenylethyl)amino]-1H-carbazole-3-carboxamide | 232b | 433 | 432.5648 |
| (3R)-N-[(1S)-1-(Aminocarbonyl)-2-methylpropyl]-2,3,4,9-tetrahydro-3-[(3-phenylpropyl)amino]-1H-carbazole-3-carboxamide | 233a | 447 | 446.5916 |
| (3S)-N-[(1S)-1-(Aminocarbonyl)-2-methylpropyl]-2,3,4,9-tetrahydro-3-[(3-phenylpropyl)amino]-1H-carbazole-3-carboxamide | 233b | 447 | 446.5916 |
| (3R)-N-[(1S)-1-(Aminocarbonyl)-2-methylpropyl]-3-[bis(3-phenylpropyl)amino]-2,3,4,9-tetrahydro-1H-carbazole-3-carboxamide | 233c | 565 | 564.7696 |
| (3R)-N-[(1S)-1-(Aminocarbonyl)-2-methylpropyl]-2,3,4,9-tetrahydro-3-[(6-phenylhexyl)amino]-1H-carbazole-3-carboxamide | 234a | 489 | 488.672 |
| (3S)-N-[(1S)-1-(Aminocarbonyl)-2-methylpropyl]-2,3,4,9-tetrahydro-3-[(6-phenylhexyl)amino]-1H-carbazole-3-carboxamide | 234b | 489 | 488.672 |
| (3R)-N-[(1S)-1-(Aminocarbonyl)-2-methylpropyl]-2,3,4,9-tetrahydro-3-[(1-methylethyl)amino]-1H-carbazole-3-carboxamide | 235a | 370 | 370.494 |
| (3S)-N-[(1S)-1-(Aminocarbonyl)-2-methylpropyl]-2,3,4,9-tetrahydro-3-[(1-methylethyl)amino]-1H-carbazole-3-carboxamide | 235b | 370 | 370.494 |
| (3R)-N-[(1S)-1-(Aminocarbonyl)-2-methylpropyl]-2,3,4,9-tetrahydro-3-[(1-methylpropyl)amino]-1H-carbazole-3-carboxamide | 236a | 385 | 384.5208 |
| (3S)-N-[(1S)-1-(Aminocarbonyl)-2-methylpropyl]-2,3,4,9-tetrahydro-3-[(1-methylpropyl)amino]-1H-carbazole-3-carboxamide | 236b | 385 | 384.5208 |
| (3R)-N-[(1S)-1-(Aminocarbonyl)-2-methylpropyl]-2,3,4,9-tetrahydro-3-[(3-methylbutyl)amino]-1H-carbazole-3-carboxamide | 237a | 399 | 398.5476 |
| (3S)-N-[(1S)-1-(Aminocarbonyl)-2-methylpropyl]-2,3,4,9-tetrahydro-3-[(3-methylbutyl)amino]-1H-carbazole-3-carboxamide | 237b | 399 | 398.5476 |
| (3R)-N-[(1S)-1-(Aminocarbonyl)-2-methylpropyl]-2,3,4,9-tetrahydro-3-(methylamino)-1H-carbazole-3-carboxamide | 238a | 342 | 342.4404 |
| (3S)-N-[(1S)-1-(Aminocarbonyl)-2-methylpropyl]-2,3,4,9-tetrahydro-3-(methylamino)-1H-carbazole-3-carboxamide | 238b | 342 | 342.4404 |
| (3R)-N-[(1S)-1-(Aminocarbonyl)-2-methylpropyl]-3-(dimethylamino)-2,3,4,9-tetrahydro-1H-carbazole-3-carboxamide | 238c | 356 | 356.4672 |
| (3S)-N-[(1S)-1-(Aminocarbonyl)-2-methylpropyl]-3-(dimethylamino)-2,3,4,9-tetrahydro-1H-carbazole-3-carboxamide | 238d | 356 | 356.4672 |

Example 31

The synthesis is carried out on a 0.2 mmol-scale according to instructions A, F, G, I, F, K and O.

| Compound | No. | MW | Mass |
|---|---|---|---|
| (3R)-N-[(1S)-1-(Aminocarbonyl)-2-methylpropyl]-2,3,4,9-tetrahydro-3-[[(methylamino)carbonyl]amino]-1H-carbazole-3-carboxamide | 239a | 385 | 385.4653 |
| (3S)-N-[(1S)-1-(Aminocarbonyl)-2-methylpropyl]-2,3,4,9-tetrahydro-3-[[(methylamino)carbonyl]amino]-1H-carbazole-3-carboxamide | 239b | 385 | 385.4653 |
| (3R)-N-[(1S)-1-(Aminocarbonyl)-2-methylpropyl]-2,3,4,9-tetrahydro-3-[[(phenylamino)carbonyl]amino]-1H-carbazole-3-carboxamide | 240a | 448 | 447.5361 |
| (3S)-N-[(1S)-1-(Aminocarbonyl)-2-methylpropyl]-2,3,4,9-tetrahydro-3-[[(phenylamino)carbonyl]amino]-1H-carbazole-3-carboxamide | 240b | 448 | 447.5361 |
| (3R)-N-[(1S)-1-(Aminocarbonyl)-2-methylpropyl]-2,3,4,9-tetrahydro-3-[[[(phenylmethyl)amino]carbonyl]amino]-1H-carbazole-3-carboxamide | 241a | 462 | 461.5629 |
| (3S)-N-[(1S)-1-(Aminocarbonyl)-2-methylpropyl]-2,3,4,9-tetrahydro-3-[[[(phenylmethyl)amino]carbonyl]amino]-1H-carbazole-3-carboxamide | 241b | 462 | 461.5629 |
| (3R)-N-[(1S)-1-(Aminocarbonyl)-2-methylpropyl]-2,3,4,9-tetrahydro-3-[[[(2-phenylethyl)amino]carbonyl]amino]-1H-carbazole-3-carboxamide | 242a | 476 | 475.5897 |
| (3S)-N-[(1S)-1-(Aminocarbonyl)-2-methylpropyl]-2,3,4,9-tetrahydro-3-[[[(2-phenylethyl)amino]carbonyl]amino]-1H-carbazole-3-carboxamide | 242b | 476 | 475.5897 |
| (3R)-N-[(1S)-1-(Aminocarbonyl)-2-methylpropyl]-3-[[(cyclohexylamino)carbonyl]amino]-2,3,4,9-tetrahydro-1H-carbazole-3-carboxamide | 243a | 454 | 453.5835 |
| (3S)-N-[(1S)-1-(Aminocarbonyl)-2-methylpropyl]-3-[[(cyclohexylamino)carbonyl]amino]-2,3,4,9-tetrahydro-1H-carbazole-3-carboxamide | 243b | 454 | 453.5835 |
| (3R)-N-[(1S)-1-(Aminocarbonyl)-2-methylpropyl]-2,3,4,9-tetrahydro-3-[[[(1-methylethyl)amino]carbonyl]amino]-1H-carbazole-3-carboxamide | 244a | 414 | 413.5189 |
| (3S)-N-[(1S)-1-(Aminocarbonyl)-2-methylpropyl]-2,3,4,9-tetrahydro-3-[[[(1-methylethyl)amino]carbonyl]amino]-1H-carbazole-3-carboxamide | 244b | 414 | 413.5189 |
| (3R)-N-[(1S)-1-(Aminocarbonyl)-2-methylpropyl]-2,3,4,9-tetrahydro-3-[[[(1-methylpropyl)amino]carbonyl]amino]-1H-carbazole-3-carboxamide | 245a | 428 | 427.5457 |
| (3S)-N-[(1S)-1-(Aminocarbonyl)-2-methylpropyl]-2,3,4,9-tetrahydro-3-[[[(1-methylethyl)amino]carbonyl]amino]-1H-carbazole-3-carboxamide | 245b | 428 | 427.5457 |
| (3R)-N-[(1S)-1-(Aminocarbonyl)-2-methylpropyl]-2,3,4,9-tetrahydro-3-[[[[(1R)-1-phenylethyl]amino]carbonyl]amino]-1H-carbazole-3-carboxamide | 246a | 476 | 475.5897 |
| (3S)-N-[(1S)-1-(Aminocarbonyl)-2-methylpropyl]-2,3,4,9-tetrahydro-3-[[[[(1R)-1-phenylethyl]amino]carbonyl]amino]-1H-carbazole-3-carboxamide | 246b | 476 | 475.5897 |

| Compound | No. | MW | Mass |
|---|---|---|---|
| (3R)-N-[(1S)-1-(Aminocarbonyl)-2-methylpropyl]-3-[[[(4-chlorophenyl)amino]carbonyl]amino]-2,3,4,9-tetrahydro-1H-carbazole-3-carboxamide | 247a | 482 | 481.9812 |
| (3S)-N-[(1S)-1-(Aminocarbonyl)-2-methylpropyl]-3-[[[(4-chlorophenyl)amino]carbonyl]amino]-2,3,4,9-tetrahydro-1H-carbazole-3-carboxamide | 247b | 482 | 481.9812 |
| (3R)-N-[(1S)-1-(Aminocarbonyl)-2-methylpropyl]-2,3,4,9-tetrahydro-3-[[[[(1S)-1-phenylethyl]amino]carbonyl]amino]-1H-carbazole-3-carboxamide | 248a | 476 | 475.5897 |
| (3S)-N-[(1S)-1-(Aminocarbonyl)-2-methylpropyl]-2,3,4,9-tetrahydro-3-[[[[(1S)-1-phenylethyl]amino]carbonyl]amino]-1H-carbazole-3-carboxamide | 248b | 476 | 475.5897 |

Example 32

The synthesis is carried out on a 0.2 mmol-scale according to instructions A, F, G, I, F, G, N and O.

| Compound | No. | MW | Mass |
|---|---|---|---|
| Ethyl (3R)-3-[[[(1S)-1-(aminocarbonyl)-2-methylpropyl]amino]carbonyl]-3-[[(4-chlorophenyl)acetyl]amino]-1,2,3,4-tetrahydro-9H-carbazole-9-acetate | 249a | 567 | 567.0825 |
| Ethyl (3S)-3-[[[(1S)-1-(aminocarbonyl)-2-methylpropyl]amino]carbonyl]-3-[[(4-chlorophenyl)acetyl]amino]-1,2,3,4-tetrahydro-9H-carbazole-9-acetate | 249b | 567 | 567.0825 |
| (3R)-N-[(1S)-1-(Aminocarbonyl)-2-methylpropyl]-3-[[(4-chlorophenyl)acetyl]amino]-2,3,4,9-tetrahydro-9-(3-phenylpropyl)-1H-carbazole-3-carboxamide | 250a | 599 | 599.1711 |
| (3S)-N-[(1S)-1-(Aminocarbonyl)-2-methylpropyl]-3-[[(4-chlorophenyl)acetyl]amino]-2,3,4,9-tetrahydro-9-(3-phenylpropyl)-1H-carbazole-3-carboxamide | 250b | 599 | 599.1711 |
| (3R)-3-[[[(1S)-1-(Aminocarbonyl)-2-methylpropyl]-amino]carbonyl]-3-[[(4-chlorophenyl)acetyl]amino]-1,2,3,4-tetrahydro-9H-carbazole-9-acetic acid | 251a | 539 | 539.0289 |
| (3S)-3-[[[(1S)-1-(Aminocarbonyl)-2-methylpropyl]amino]carbonyl]-3-[[(4-chlorophenyl)acetyl]amino]-1,2,3,4-tetrahydro-9H-carbazole-9-acetic acid | 251b | 539 | 539.0289 |
| (3R)-N-[(1S)-1-(Aminocarbonyl)-2-methylpropyl]-3-[[(4-chlorophenyl)acetyl]amino]-2,3,4,9-tetrahydro-9-(3-methylbutyl)-1H-carbazole-3-carboxamide | 252a | 551 | 551.1271 |
| (3S)-N-[(1S)-1-(Aminocarbonyl)-2-methylpropyl]-3-[[[(4-chlorophenyl)acetyl]amino]-2,3,4,9-tetrahydro-9-(3-methylbutyl)-1H-carbazole-3-carboxamide | 252b | 551 | 551.1271 |
| (3R)-N-[(1S)-1-(Aminocarbonyl)-2-methylpropyl]-3-[[(4-chlorophenyl)acetyl]amino]-2,3,4,9-tetrahydro-9-(4-pyridinylmethyl)-1H-carbazole-3-carboxamide | 253a | 572 | 572.1056 |
| (3S)-N-[(1S)-1-(Aminocarbonyl)-2-methylpropyl]-3-[[(4-chlorophenyl)acetyl]amino]-2,3,4,9-tetrahydro-9-(4-pyridinylmethyl)-1H-carbazole-3-carboxamide | 253b | 572 | 572.1056 |
| (3R)-N-[(1S)-1-(Aminocarbonyl)-2-methylpropyl]-3-[[(4-chlorophenyl)acetyl]amino]-2,3,4,9-tetrahydro-9-(3-pyridinylmethyl)-1H-carbazole-3-carboxamide | 254a | 572 | 572.1056 |
| (3S)-N-[(1S)-1-(Aminocarbonyl)-2-methylpropyl]-3-[[(4-chlorophenyl)acetyl]amino]-2,3,4,9-tetrahydro-9-(3-pyridinylmethyl)-1H-carbazole-3-carboxamide | 254b | 572 | 572.1056 |
| (3R)-N-[(1S)-1-(Aminocarbonyl)-2-methylpropyl]-3-[[(4-chlorophenyl)acetyl]amino]-2,3,4,9-tetrahydro-9-(2-naphthalenylmethyl)-1H-carbazole-3-carboxamide | 255a | 621 | 621.1773 |
| (3S)-N-[(1S)-1-(Aminocarbonyl)-2-methylpropyl]-3-[[(4-chlorophenyl)acetyl]amino]-2,3,4,9-tetrahydro-9-(2-naphthalenylmethyl)-1H-carbazole-3-carboxamide | 255b | 621 | 621.1773 |
| (3R)-N-[(1S)-1-(Aminocarbonyl)-2-methylpropyl]-3-[[(4-chlorophenyl)acetyl]amino]-2,3,4,9-tetrahydro-9-(2-methylpropyl)-1H-carbazole-3-carboxamide | 256a | 537 | 537.1003 |
| (3S)-N-[(1S)-1-(Aminocarbonyl)-2-methylpropyl]-3-[[(4-chlorophenyl)acetyl]amino]-2,3,4,9-tetrahydro-9-(2-methylpropyl)-1H-carbazole-3-carboxamide | 256b | 537 | 537.1003 |
| (3R)-N-[(1S)-1-(Aminocarbonyl)-2-methylpropyl]-3-[[(4-chlorophenyl)acetyl]amino]-2,3,4,9-tetrahydro-9-(2-phenylethyl)-1H-carbazole-3-carboxamide | 257a | 585 | 585.1443 |
| (3S)-N-[(1S)-1-(Aminocarbonyl)-2-methylpropyl]-3-[[(4-chlorophenyl)acetyl]amino]-2,3,4,9-tetrahydro-9-(2-phenylethyl)-1H-carbazole-3-carboxamide | 257b | 585 | 585.1443 |
| (3R)-N-[(1S)-1-(Aminocarbonyl)-2-methylpropyl]-3-[[(4-chlorophenyl)acetyl]amino]-9-ethyl-2,3,4,9-tetrahydro-1H-carbazole-3-carboxamide | 258a | 509 | 509.0467 |
| (3S)-N-[(1S)-1-(Aminocarbonyl)-2-methylpropyl]-3-[[(4-chlorophenyl)acetyl]amino]-9-ethyl-2,3,4,9-tetrahydro-1H-carbazole-3-carboxamide | 258b | 509 | 509.0467 |
| (3R)-N-[(1S)-1-(Aminocarbonyl)-2-methylpropyl]-3-[[(4-chlorophenyl)acetyl]amino]-9-(cyclohexylmethyl)-2,3,4,9-tetrahydro-1H-carbazole-3-carboxamide | 259a | 577 | 577.1649 |
| (3S)-N-[(1S)-1-(Aminocarbonyl)-2-methylpropyl]-3-[[(4-chlorophenyl)acetyl]amino]-9-(cyclohexylmethyl)-2,3,4,9-tetrahydro-1H-carbazole-3-carboxamide | 259b | 577 | 577.1649 |
| (3R)-N-[(1S)-1-(Aminocarbonyl)-2-methylpropyl]-3-[[(4-chlorophenyl)acetyl]amino]-9-[(2,6-difluorophenyl)methyl]-2,3,4,9-tetrahydro-1H-carbazole-3-carboxamide | 260a | 607 | 607.0977 |
| (3S)-N-[(1S)-1-(Aminocarbonyl)-2-methylpropyl]-3-[[(4-chlorophenyl)acetyl]amino]-9-[(2,6-difluorophenyl)methyl]-2,3,4,9-tetrahydro-1H-carbazole-3-carboxamide | 260b | 607 | 607.0977 |

Example 33

The synthesis is carried out on a 0.2 mmol-scale according to instructions A, F, G, I, F, H, N and O.

| Compound | No. | MW | Mass |
|---|---|---|---|
| (3R)-3-(Acetylamino)-N-[(1S)-1-(aminocarbonyl)-2-methylpropyl]-2,3,4,9-tetrahydro-9-(3-phenylpropyl)-1H-carbazole-3-carboxamide | 261a | 489 | 488.6284 |
| (3S)-3-(Acetylamino)-N-[(1S)-1-(aminocarbonyl)-2-methylpropyl]-2,3,4,9-tetrahydro-9-(3-phenylpropyl)-1H-carbazole-3-carboxamide | 261b | 489 | 488.6284 |
| (3R)-3-(Acetylamino)-N-[(1S)-1-(aminocarbonyl)-2-methylpropyl]-2,3,4,9-tetrahydro-9-(3-methylbutyl)-1H-carbazole-3-carboxamide | 262a | 441 | 440.5844 |
| (3S)-3-(Acetylamino)-N-[(1S)-1-(aminocarbonyl)-2-methylpropyl]-2,3,4,9-tetrahydro-9-(3-methylbutyl)-1H-carbazole-3-carboxamide | 262b | 441 | 440.5844 |

-continued

| | | | |
|---|---|---|---|
| (3R)-3-(Acetylamino)-N-[(1S)-1-(aminocarbonyl)-2-methylpropyl]-2,3,4,9-tetrahydro-9-(2-naphthalenylmethyl)-1H-carbazole-3-carboxamide | 263a | 511 | 510.6346 |
| (3S)-3-(Acetylamino)-N-[(1S)-1-(aminocarbonyl)-2-methylpropyl]-2,3,4,9-tetrahydro-9-(2-naphthalenylmethyl)-1H-carbazole-3-carboxamide | 263b | 511 | 510.6346 |
| 3-(Acetylamino)-N-[(1S)-1-(aminocarbonyl)-2-methylpropyl]-2,3,4,9-tetrahydro-9-(1-naphthalenylmethyl)-1H-carbazole-3-carboxamide | 264 | 511 | 510.6346 |
| 3-(Acetylamino)-N-[(1S)-1-(aminocarbonyl)-2-methylpropyl]-9-(cyclohexylmethyl)-2,3,4,9-tetrahydro-1H-carbazole-3-carboxamide | 265 | 467 | 466.6222 |
| (3R)-3-(Acetylamino)-N-[(1S)-1-(aminocarbonyl)-2-methylpropyl]-2,3,4,9-tetrahydro-9-(2-methylpropyl)-1H-carbazole-3-carboxamide | 266a | 427 | 426.5576 |
| (3S)-3-(Acetylamino)-N-[(1S)-1-(aminocarbonyl)-2-methylpropyl]-2,3,4,9-tetrahydro-9-(2-methylpropyl)-1H-carbazole-3-carboxamide | 266b | 427 | 426.5576 |

Example 34

The synthesis is carried out on a 0.2 mmol-scale according to instructions D, F, G, I, F, O and subsequent coupling according to Example 6.

| | | | |
|---|---|---|---|
| Phenylmethyl [(1S,2S)-1-[[[(3R)-3-[[[(1S)-1-(hydroxymethyl)-2-methylpropyl]amino]-carbonyl]-2,3,4,9-tetrahydro-1H-carbazol-3-yl]amino]carbonyl]-2-methylbutyl]carbamate | 267a | 563 | 562.7068 |
| Phenylmethyl [(1S,2S)-1-[[[(3S)-3-[[[(1S)-1-(hydroxymethyl)-2-methylpropyl]amino]-carbonyl]-2,3,4,9-tetrahydro-1H-carbazol-3-yl]amino]carbonyl]-2-methylbutyl]carbamate | 267b | 563 | 562.7068 |

Example 35

Ethyl 2,3,4,9-tetrahydro-3-(3-phenylpropyl)-1H-carbazole-3-carboxylate 268

10 mmol (1.6 ml) of ethyl 4-oxocyclohexanecarboxylate, 25 mmol (1.4 ml) of glycol and 10 μmol of pTsOH are refluxed for 24 hours in dry toluene in a water separator. Solvent is removed and taken up in ethyl acetate/water. The organic phase is washed with water, dried and evaporated to the dry state. The product is distilled under high vacuum at 120° C. and 0.03 mbar in the ball tube still.

Yield: 1.52 g of 4-ethyl 1,4-dioxaspiro[4,5]decane-8-carboxylate 269.

85 μl of diisopropylamine in 500 μl of dry THF is added in drops to 0.6 mmol of a 1.6 molar solution of butyllithium in heptane at −20° C. under argon, and it is stirred for 10 more minutes. After cooling to −70° C., 0.5 mmol (107 mg) of 269 in 200 μl of dry THF is added in drops, allowed to reach 0° C. within one hour, and stirred for another 30 minutes. After cooling to −70° C., 0.7 mmol (106 μl) of 1-bromo-3-phenylpropane in 300 μl of dry THF is added, and it is allowed to reach room temperature and stirred for one more hour. The organic phase is carefully mixed with saturated NH$_4$Cl solution and n-hexane, and it is stirred for 10 minutes. The organic phase is separated and washed with water. After filtration with a Whatman filter, it is evaporated to the dry state.

Yield: 165 mg of ethyl 8-(3-phenylpropyl)-1,4-dioxaspiro[4,5]decane-8-carboxylate 270.

0.6 mmol (200 mg) of 270 is taken up in 25 ml of acetone/0.1 M HCl 1:1 and stirred with catalytic amounts of pTsOH for 48 hours at 50° C. The acetone is drawn off in a rotary evaporator, and the precipitated product is filtered off, rewashed with water and dried.

Yield: 156 mg of ethyl 4-oxo-8-(3-phenylpropyl)cyclohexanecarboxylate 271.

The indolization is carried out as described under Example 1 with phenylhydrazine.

The yield after evaporation and preparative HPLC: 65 mg of ethyl 2,3,4,9-tetrahydro-3-(3-phenylpropyl)-1H-carbazole-3-carboxylate 268.

ES-MS: 362 (M+H$^+$)

80 mg of ethyl 6,8-dichloro-2,3,4,9-tetrahydro-3-(3-phenylpropyl)-1H-carbazole-3-carboxylate 272 is produced analogously with use of 2,4-dichlorophenylhydrazine.

ES-MS: 430 (M+H$^+$)

Example 36

2,3,4,9-Tetrahydro-3-(3-phenylpropyl)-1H-carbazole-3-carboxylic Acid 273

3.94 mmol (1.31 g) of 269 is stirred in 50 ml of methanol and 30 ml of 50% sodium hydroxide solution for 4 hours at 60° C. It is acidified with dilute HCl and extracted with ether. Drying with Na$_2$SO$_4$ and evaporation yields 1.02 g (85%) of white solid 8-(3-phenylpropyl)-1,4-dioxaspiro[4,5]decane-8-carboxylic acid 274.

65 mg of 274 is first deprived of protection with HCl as described for 270 and 271 and then reacted with phenylhydrazine for indolization.

Yield after evaporation and preparative HPLC: 15 mg of 273.

ES-MS: 334 (M+H$^+$)

39 mg of 6,8-dichloro-2,3,4,9-tetrahydro-3-(3-phenylpropyl)-1H-carbazole-3-carboxylic acid 275 is produced analogously with use of 2,4-dichlorophenylhydrazine.

ES-MS: 478 (M+H$^+$)

Example 37

2,3,4,9-Tetrahydro-N-[(1S)-1-(hydroxymethyl)-2-methylpropyl]-3-(3-phenylpropyl)-1H-carbazole-3-carboxamide 276

0.66 mmol (200 mg) of 274 is reacted analogously to Example 6 with 1.5 equivalents of valinol. 277 mg of white solid N-[(1S)-1-(hydroxymethyl)-2-methylpropyl]-8-(3-phenylpropyl)-1,4-dioxaspiro [4,5]decane-8-carboxamide 277 is obtained.

Then, as described for 270 and 271, 0.3 mmol (117 mg) of 277 is first deprived of protection with HCl and then reacted with phenylhydrazine for indolization.

Yield after evaporation and preparative HPLC: 15 mg of 276.

ES-MS: 418 (M+H$^+$)

25 mg of 6,8-dichloro-2,3,4,9-tetrahydro-N-[(1S)-1-(hydroxymethyl)-2-methylpropyl]-3-(3-phenylpropyl)-1H-carbazole-3-carboxamide 278 is produced analogously with use of 2,4-dichlorophenylhydrazine.

ES-MS: 486 (M+H$^+$)

Example 38

2,3,4,9-Tetrahydro-3-(3-phenylpropyl)-N-(2-pyridinylmethyl)-1H-carbazole-3-methanamine 279

54 ml of a 1 M solution of $LiAlH_4$ in dry THF is carefully added to a solution of 18 mmol (6 g) of 270 in 250 ml of dry THF under argon at room temperature. After 3 hours of refluxing, it is carefully hydrolyzed with 300 ml of saturated $NH_4Cl$ solution and mixed with 250 ml of ether. The aluminum salts are filtered off and washed with ether. Drying the ether phase with $Na_2SO_4$ and evaporation of the solvent yield 3.4 g of 8-(3-phenylpropyl)-1,4-dioxaspiro[4,5]decane-8-methanol 280.

5.86 mmol (1.7 g) of 280 is dissolved in 60 ml of dry DCM and 20 ml of dry DMSO. First 44 mmol (6.1 ml) of TEA and then 17.6 mmol (2.8 g) of $SO_3$-pyridine complex are carefully added at room temperature under nitrogen and stirred for one hour. Then, it is mixed with 200 ml of saturated $NH_4Cl$ solution and extracted with 150 ml of ether. Drying the ether phase with $Na_2SO_4$ and evaporation of the solvent yield 1.9 g of 8-(3-phenylpropyl)-1,4-dioxaspiro[4,5]decane-8-carbaldehyde 281 as a colorless oil.

0.719 mmol of sodium triacetoxy borohydride is added to a mixture of 0.359 mmol (103 mg) of 281 and 0.359 mmol (37 ml) of 2-pyridinemethanamine in 2.5 ml of 1,2-dichloroethane. The mixture is stirred under $N_2$ for 3 hours at room temperature. It is mixed with saturated $NaHCO_3$ solution and extracted with ether. The dried and evaporated ether extract yields 101 mg (76%) of white solid N-[8—(3-phenylpropyl)-1,4-dioxaspiro[4,5]dec-8-yl]-2-pyridinemethanamine 282.

Then, 101 mg of 282 is first removed from protection with HCl as described for 270 and 271 and then reacted with phenylhydrazine for indolization.

Yield after evaporation and preparative HPLC: 71 mg of 279.

ES-MS: 410 (M+H$^+$)

54 mg of 6,8-dichloro-2,3,4,9-tetrahydro-3-(3-phenylpropyl)-N-(2-pyridinylmethyl)-1H-carbazole-3-methanamine 283 is produced analogously with use of 2,4-dichlorophenylhydrazine.

ES-MS: 478 (M+H$^+$)

Example 39

(2S)-3-Methyl-2-[[[2,3,4,9-tetrahydro-3-(3-phenylpropyl)-1H-carbazol-3-yl]methyl]-amino]-1-butanol 284

0.368 mmol (106 mg) of 281 and 0.368 mmol (38 mg) of valinol are dissolved in 1.5 ml of dry methanol and stirred for 30 minutes at room temperature. After cooling to 0° C., 0.557 mmol (21 mg) of $NaBH_4$ is added, and it is stirred for 1 hour at room temperature. 0.437 mmol (25 μl) of acetic acid is added, and it is stirred at pH 6 for another 2 hours. It is mixed with saturated $NaHCO_3$ solution and extracted with ether. Drying the organic phase with $Na_2SO_4$ and evaporation yield 106 mg (77%) of a colorless oil for 270 and 271.

Then, protection is removed as described for 270 and 271, and indolization is done. Yield after evaporation and preparative HPLC: 18 mg of white solid 284.

ES-MS: 405 (M+H$^+$)

17 mg of (2S)-2-[[[6,8-dichloro-2,3,4,9-tetrahydro-3-(3-phenylpropyl)-1H-carbazol-3-yl]methyl]amino]-3-methyl-1-butanol 286 is produced analogously with use of 2,4-dichlorophenylhydrazine.

ES-MS: 473 (M+H$^+$)

Example 40

2,3,4,9-Tetrahydro-3-(3-phenylpropyl)-O-(4-pyridinylmethyl)-1H-carbazole-3-methanol 287

0.689 mmol of NaH (as 55% suspension in mineral oil) is added to a solution of 0.344 mmol (100 mg) of 280 in 10 ml of dry DMF at 0° C. under $N_2$ atmosphere. It is allowed to reach room temperature and stirred for 30 more minutes. 1.377 mmol of 4-(chloromethyl)pyridine is added, and it is stirred overnight at 95–100° C. After cooling to room temperature, it is hydrolyzed with 2 ml of water and extracted with ether. Drying of the LM and evaporation yield 115 mg of yellow oil 288.

Then, protection is removed as described for 270 and 271, and indolization is done.

Yield after evaporation and preparative HPLC: 14 mg of white solid 287.

ES-MS: 411 (M+H$^+$)

Example 41

Ethyl 3-[2,3,4,9-tetrahydro-3-(3-phenylpropyl)-1H-carbazol-3-yl]-2-propenoate 289

0.347 mmol of 281 in 0.5 ml of THF is added in drops while being cooled with ice to a solution of 0.378 mmol of ethyl(triphenylphosphoranylidene)acetate in 1 ml of absolute THF. After the addition is completed, it is allowed to heat to room temperature and stirred for another 2 days. Then, it is hydrolyzed with water and extracted with ether. It is dried with $Na_2SO_4$, phosphane oxide and dessicant are filtered off, and solvent is removed.

Yield: 80% ethyl 3-[8-(3-phenylpropyl)-1,4-dioxaspiro[4,5]dec-8-yl]-2-propenoate 290.

Then, protection is removed as described for 270 and 271, and indolization is done.

Yield after evaporation and preparative HPLC: 9 mg of white solid 289.

ES-MS: 388 (M+H$^+$)

In addition, compounds nos. 293 to 300, 302 as well as 304 to 306 according to the invention that fall under general formula (I) are obtained according to instructions A, F, G, F, G and O, compound 301 is obtained according to instructions B, F, G, F, G and O, and compound 303 is obtained according to instructions A, F, G, F, G, F, L and O on a 0.2 mmol scale.

| Compound Name | Number | $M_{Fnd}$ | $M_{Cld}$ |
| --- | --- | --- | --- |
| Phenylmethyl [(1S,2S)-1-[[[(3R)-3-[[[(1S)-1-(aminocarbonyl)-2-methylpropyl]amino]carbonyl]-6,8-difluoro-2,3,4,9-tetrahydro-1H-carbazol-3-yl]amino]carbonyl]-2-methylbutyl]carbamate | 293 | 612 | 611.6861 |
| Phenylmethyl [(1S,2S)-1-[[[(3R)-3-[[[(1S,2S)-1-(aminocarbonyl)-2-methylbutyl]amino]carbonyl]- | 294 | 620 | 619.7585 |

-continued

| Compound Name | Number | M_Fnd | M_Cld |
|---|---|---|---|
| 8-methoxy-2,3,4,9-tetrahydro-1H-carbazol-3-yl]amino]carbonyl]-2-methylbutyl]carbamate | | | |
| Phenylmethyl [(1S,2S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-2-methylbutyl]carbamate | 295 | 659 | 658.6229 |
| Phenylmethyl [(1S,2S)-1-[[[(3R)-3-[[[(1S)-1-(aminocarbonyl)-3-methylbutyl]amino]carbonyl]-6,8-dichloro-2,3,4,9-tetrahydro-1H-carbazol-3-yl]amino]carbonyl]-2-methylbutyl]carbamate | 296 | 659 | 658.6229 |
| Phenylmethyl [(1S,2S)-1-[[[(3R)-3-[[[(1S)-1-(aminocarbonyl)-2-cyclohexylethyl]amino]carbonyl]-6,8-dichloro-2,3,4,9-tetrahydro-1H-carbazol-3-yl]amino]carbonyl]-2-methylbutyl]carbamate | 297 | 699 | 698.6875 |
| Phenylmethyl [(1S,2S)-1-[[[(3R)-3-[[[(1S)-1-(aminocarbonyl)-2,2-dimethylpropyl]amino]carbonyl]-6,8-dichloro-2,3,4,9-tetrahydro-1H-carbazol-3-yl]amino]carbonyl]-2-methylbutyl]carbamate | 298 | 659 | 658.6229 |
| Phenylmethyl [(1S,2S)-1-[[[(3R)-3-[[[(1S)-1-(aminocarbonyl)-3-phenylpropyl]amino]carbonyl]-6,8-dichloro-2,3,4,9-tetrahydro-1H-carbazol-3-yl]amino]carbonyl]-2-methylbutyl]carbamate | 299 | 707 | 706.6669 |
| Phenylmethyl [(1S,2S)-1-[[[(3R)-3-[[[(1S)-1(aminocarbonyl)-2-methylbutyl]amino]carbonyl]-6,8-dichloro-2,3,4,9-tetrahydro-1H-carbazol-3-yl]amino]carbonyl]-2-cyclohexylmethyl]carbamate | 300 | 685 | 684.6607 |
| Phenylmethyl [(1S,2S)-1-[[[(3R)-3-[[[(1S,2S)-1-(carboxy)-2-methylbutyl]amino]carbonyl]-6,8-dichloro-2,3,4,9-tetrahydro-1H-carbazol-3-yl]amino]carbonyl]-2-methylbutyl]carbamate | 301 | 660 | 659.607 |
| Phenylmethyl [(1S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-2-(4-hydroxyphenyl)-ethyl]carbamate | 302 | 709 | 708.6391 |
| Phenylmethyl [(1S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-3-(4-hydroxyphenyl)-propyl]carbamate | 303 | 723 | 722.6659 |
| Phenylmethyl [(1S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-3-phenylpropyl]carbamate | 304 | 707 | 706.6669 |
| Phenylmethyl [(1S)-1-[[[(3R)-3-[[[(1S,2S)-1-(aminocarbonyl)-2-methylbutyl]amino]carbonyl]-6,8-dichloro-2-3,4,9-tetrahydro-1H-carbazol-3-yl]amino]carbonyl]-3-methylbutyl]carbamate | 305 | 659 | 658.6229 |
| Phenylmethyl [(1S)-1-[[[(3R)-3-[[[(1S)-1-(aminocarbonyl)-3-methylbutyl]amino]carbonyl]-6,8-dichloro-2,3,4,9-tetrahydro-1H-carbazol-3-yl]amino]carbonyl]-3-methylbutyl]carbamate | 306 | 659 | 658.6229 |

III. Detection of the GnRH-Antagonistic Action of Compounds (I) According to the Invention Materials:

Buserelin is ordered from Welding (Frankfurt/Main, Germany). The compound is labeled with $^{125}$I by use of the chloramine T-method and Na$^{125}$I (4000 Ci/mmol; Amersham-Buchler, Brunswick, Germany). The labeled substance is purified by reverse phase HPLC on a Spherisorb ODS II column (250×4 mm, particle size 3 μm) by elution with 50% acetonitrile/0.15% trifluoroacetic acid at a flow rate of 0.5 ml/minute. The specific activity is 2000 Ci/mmol.

All other chemicals are ordered from commercial sources at the highest available purity.

Cell Culture:

Alpha T3-1 cells (Bilezikjian et al., *Mol. Endocrinol* 5 (1991), 347–355) are cultivated in DMEM medium (Gibco-BRL, Eggenstein-Leopoldshafen, Germany) with penicillin (100 I.U./ml), streptomycin (0.1 mg/ml) and glutamine (0.01 mol/l) and 10% fetal calf serum (FCS; PAA Laboratories, Coelbe, Germany) on plastic tissue culture plates (Nunc, 245×245×20 mm). CHO-3 cells (Schmid et al., *J. Biol. Chem.* 275 (2000), 9193–9200) are cultivated under identical conditions, apart from the fact that Ham's F12 medium (Gibco-BRL) is used.

Ten confluent cell culture plates are flushed twice with 50 ml of phosphate-buffered salt solution (PBS). The cells are harvested by scraping them off with a rubber scraper in 5 ml of PBS and sedimented by centrifuging in a laboratory centrifuge (Heraeus) at 800 rpm for 10 minutes. The cell pellet is resuspended in 5 ml of 0.25 mol/l of saccharose/0.01 mol/l of triethanolamine, pH 7.4. The cells are lysed by three cycles of freezing in dry ice/ethanol bath and thawing at room temperature. The lysate is centrifuged at 900 rpm for 10 minutes, and the sediment is discarded. The supernatant is centrifuged at 18,000 rpm in a Sorvall SS34 rotor for 30 minutes. The pellet (cell membranes) is suspended by Potters in 5 ml of assay buffer (0.25 mol/l of saccharose, 0.01 mol/l of triethanolamine, pH 7.5, 1 mg/ml of ovalbumin) and stored in 200 μl of aliquots at −20° C. The determination of protein is carried out according to the Bradford method (*Anal. Biochem.* 72 (1976), 248–254).

Receptor Assay:

Binding studies for competition curves are performed as triplicates. A test sample contains 60 μl of cell membrane suspension (10 μg of protein for αT3-1 cells or 40 μg of protein for CHO3 cells), 20 μl of $^{125}$I-labeled buserelin (100,000 Ipm per sample for competition curves and between 1,500 and 200,000 Ipm for saturation experiments) and 20 μl of test buffer or test compound solution. The test compounds are dissolved in distilled water or 50% ethanol. Serial dilutions ($5 \times 10^{-6}$ mol/l to $5 \times 10^{-2}$ mol/l) are produced in test buffer. The unspecific binding is determined in the presence of excess unlabeled buserelin ($10^{-6}$ mol/1). The test samples are incubated for 30 minutes at room temperature. Bonded and free ligands are separated by filtration (Whatman GF/C-filter, 2.5 cm diameter) with use of an Amicon 10x collecting device and washed twice with 5 ml of 0.02 mol/l of Tris/HCl, pH 7.4. The filters are moistened with 0.3% polyethylenimine (Serva; Heidelberg, Germany) for 30 minutes to reduce the unspecific binding. The radioactivity that was held up by the filter is determined in a 5-channel gamma-counter (Wallac-LKB 1470 Wizard).

In the table below, the $IC_{50}$ values that are obtained for the preferred compounds, as defined above, are indicated.

| Compound Name | Example No. | hGnRH-Receptor $IC_{50}$ [M] | $Ca^{2+}$ Release Human $IC_{50}$ [M] |
|---|---|---|---|
| N-[[(3R)-2,3,4,9-Tetrahydro-3-[(1-oxo-2,3-diphenylpropyl)amino]-1H-carbazol-3-yl]carbonyl]-L-valyl-L-aspartamide | 18 | 0.0000009 | 0.000005 |
| (3S)-N-[(1S)-1-(Aminocarbonyl)-2-methylpropyl]-2,3,4,9-tetrahydro-3-[(1H-indol-3-ylacetyl)amino]-1H-carbazole-3-carboxamide | 164b | 0.000006 | 0.0000065 |
| (3S)-N-[(1S)-1-(Aminocarbonyl)-2-methylpropyl]-2,3,4,9-tetrahydro-3-[(2-naphthalenylacetyl)amino]-1H-carbazole-3-carboxamide | 161b | 0.0000037 | 0.0000036 |
| N-[[(3R)-2,3,4,9-Tetrahydro-3-[[(2S,3S)-3-methyl-1-oxo-2-[(1-oxo-3-phenylpropyl)-amino]pentyl]amino]-1H-carbazol-3-yl]carbonyl]-L-valyl-L-aspartamide | 22 | 0.000002 | 0.000001 |
| Phenylmethyl [(1S,2S)-1-[[[(3R)-3-[[[(1S,2S)-1-(aminocarbonyl)-2-methylbutyl]amino]-carbonyl]-2,3,4,9-tetrahydro-1H-carbazol-3-yl]amino]carbonyl]-2-methylbutyl]carbamate | 64 | 0.0000017 | 0.0000015 |
| Phenylmethyl [(1S,2S)-1-[[[(3R)-3-[[[(1S)-1-[[[4-(aminocarbonyl)phenyl]amino]carbonyl]-2-methylpropyl]amino]carbonyl]-2,3,4,9-tetrahydro-1H-carbazol-3-yl]amino]carbonyl]-2-methylbutyl]carbamate | 45 | 0.0000003 | 0.000001 |
| Phenylmethyl [(1S,2S)-2-methyl-1-[[[(3R)-2,3,4,9-tetrahydro-3-[[[(1S)-2-methyl-1-[(methylamino)carbonyl]propyl]amino]carbonyl]-1H-carbazol-3-yl]amino]carbonyl]-butyl]-carbamate | 222a | 0.0000025 | 0.000003 |
| Phenylmethyl [(1S,2S)-1-[[[(3R)-3-[[[(1S)-1-(aminocarbonyl)-2-methylpropyl]amino]-carbonyl]-2,3,4,9-tetrahydro-1H-carbazol-3-yl]amino]carbonyl]-2-methylbutyl]carbamate | 58 | 0.0000003 | 0.00000037 |
| Phenylmethyl [(1S,2S)-1-[[[(3R)-3-[[[(2S)-2-(aminocarbonyl)-1-pyrrolidinyl]carbonyl]-2,3,4,9-tetrahydro-1H-carbazol-3-yl]amino]carbonyl]-2-methylbutyl]carbamate | 181a | 0.0000007 | 0.000003 |
| Phenylmethyl [(1S,2S)-1-[[[(3R)-3-[[(2S)-2-(aminocarbonyl)octahydro-1H-indol-1-yl]carbonyl]-2,3,4,9-tetrahydro-1H-carbazol-3-yl]amino]carbonyl]-2-methylbutyl]carbamate | 190a | 0.000002 | 0.0000005 |
| 2,3,4,9-Tetrahydro-3-(3-phenylpropyl)-N-(2-pyridinylmethyl)-1H-carbazole-3-methanamine | 279 | 0.000002 | 0.000003 |
| (2S)-3-Methyl-2-[[[2,3,4,9-tetrahydro-3-(3-phenylpropyl)-1H-carbazol-3-yl]methyl]-amino]-1-butanol | 284 | 0.000007 | 0.000007 |
| N-[(1S)-1-(Aminocarbonyl)-2-methylpropyl]-2,3,4,9-tetrahydro-3-[[(4-methoxyphenyl)-acetyl]amino]-1H-carbazole-3-carboxamide | 175 | 0.000008 | 0.0000018 |
| (3R)-N-[(1S)-1-(Aminocarbonyl)-2-methylpropyl]-3-[[(3-bromophenyl)acetyl]-amino]-2,3,4,9-tetrahydro-1H-carbazole-3-carboxamide | 96 | 0.000004 | 0.000003 |
| (3R)-N-[(1S)-1-(Aminocarbonyl)-2-methylpropyl]-3-[[(4-fluorophenyl)acetyl]-amino]-2,3,4,9-tetrahydro-1H-carbazole-3-carboxamide | 91 | 0.0000024 | 0.000002 |
| (3R)-N-[(1S)-1-(Aminocarbonyl)-2-methylpropyl]-3-[[(4-chlorophenyl)acetyl]-amino]-2,3,4,9-tetrahydro-1H-carbazole-3-carboxamide | 167a | 0.000001 | 0.0000026 |
| (3R)-N-[(1S)-1-(Aminocarbonyl)-2-methylpropyl]-2,3,4,9-tetrahydro-3-[(6-phenylhexyl)amino]-1H-carbazole-3-carboxamide | 234a | 0.000009 | 0.000001 |

-continued

| Compound Name | Example No. | hGnRH-Receptor IC$_{50}$ [M] | Ca$^{2+}$ Release Human IC$_{50}$ [M] |
|---|---|---|---|
| Phenylmethyl [(1S,2S)-1-[[[(3R)-3-[[[(1S)-1-(aminocarbonyl)-2-methylpropyl]amino]-carbonyl]-2,3,4,9-tetrahydro-8-methyl-1H-carbazol-3-yl]amino]carbonyl]-2-methylbutyl]carbamate | 150a | 0.00000011 | 0.00000028 |
| Phenylmethyl [(1S,2S)-1-[[[(3R)-3-[[[(1S)-1-(aminocarbonyl)-2-methylpropyl]amino]-carbonyl]-6-chloro-2,3,4,9-tetrahydro-1H-carbazol-3-yl]amino]carbonyl]-2-methylbutyl]carbamate | 148a | 0.00000008 | 0.00000014 |
| Phenylmethyl [(1S,2S)-1-[[[(3R)-3-[[[(1S)-1-(aminocarbonyl)-2-methylpropyl]amino]-carbonyl]-2,3,4,9-tetrahydro-8-methoxy-1H-carbazol-3-yl]amino]carbonyl]-2-methylbutyl]carbamate | 147a | 0.000000076 | 0.00000025 |
| Phenylmethyl [(1S,2S)-1-[[[(3R)-3-[[[(1S)-1-(aminocarbonyl)-2-methylpropyl]amino]-carbonyl]-6,8-dichloro-2,3,4,9-tetrahydro-1H-carbazol-3-yl]amino]carbonyl]-2-methylbutyl]carbamate | 184a | 0.000000015 | 0.000000045 |
| Phenylmethyl [(1S,2S)-1-[[[(3R)-3-[[[(1S)-1-(hydroxymethyl)-2-methylpropyl]-amino]carbonyl]-2,3,4,9-tetrahydro-1H-carbazol-3-yl]amino]carbonyl]-2-methylbutyl]carbamate | 267a | 0.0000004 | 0.0000005 |
| (2S)-1-[[(3R)-3-[[(4-Chlorophenyl)acetyl]-amino]-2,3,4,9-tetrahydro-8-methoxy-1H-carbazol-3-yl]carbonyl]-2-pyrrolidinecarboxamide | 189a | 0.0000007 | 0.0000005 |
| 6,8-Dichloro-2,3,4,9-tetrahydro-3-(3-phenylpropyl)-N-(2-pyridinylmethyl)-1H-carbazole-3-methanamine | 283 | 0.000001 | 0.000003 |

The compounds of numbers 293 to 306 are tested according to the methods that are indicated below:

Receptor Binding Assay

Materials:

$^{125}$I-Triptorelin [$^{125}$I-(D)-Trp6-GnRH] is ordered from the Biotrend Company (Cologne, Germany). The specific activity in each case is 2.13 Ci/mmol. All other chemicals are ordered from commercial sources at the highest available purity.

Cell Culture:

Transfixed LTK' cells (ATCC No. CCL-11.3) are cultivated in DMEM medium (Invitrogen Life Technologies, Germany) with penicillin (100 I.U./ml), streptomycin (0.1 mg/ml) and glutamine (0.01 mol/l) and 10% fetal calf serum (FCS; Invitrogen Life Technologies, Germany) on plastic tissue culture plates (Nunc, Germany, 245×245×20 nun).

Testing:

80% confluent cell culture plates are washed twice with 50 ml of phosphate-buffered salt solution (PBS) and dissolved below with 0.01 M EDTA solution. The cells are pelletized by centrifuging at 200×g for 5 minutes in a laboratory centrifuge (Kendro, Germany). The cell pellet is resuspended in 3 ml of binding medium (DMEM; 10 mmol of Hepes; 0.5% BSA; 0.1% NaN$_3$; 1 g/l of bacitracin (freshly added, stock 100×); 0.1 g/l of SBTI (freshly added, stock 1000×), and the cell count is determined by means of trypan blue staining in a Neubauer counting chamber. The cell suspension is set with binding medium to a concentration of 5×10$^5$ Z/0.05 ml.

Binding tests for competition curves are performed as duplicates. The test substances are used as 10 mmol DMSO solutions. They are diluted with binding medium to 4× the final concentration used. 25 μl of the substance dilution is mixed with 25 μl of tracer solution ($^{125}$I-triptorelin). The concentration of tracer is set to about 50,000 cpm (measured in Cobra II, γ-counter, PE Liefe Science, Germany) in the final reaction volume of 100 μl.

200 μl of a silicone/paraffin oil mixture (84%:16%) is introduced into 650 μl pointed-bottom tubes (Roth, Germany). 50 μl of the cell suspension is pipetted thereto and subsequently 50 μl of the test substance/tracer mixture. The tubes are sealed and incubated for 60 minutes at 37° C. in an incubator that rotates via the top. After incubation, the samples are centrifuged in a centrifuge (Kendro, Germany) at 900 rpm and subsequently flash-frozen in liquid N$_2$. The tip with the cell pellet is cut off and inserted into the prepared counting tube (Roth, Germany). The remainder of the pointed-bottom tube with the remaining supernatant is also inserted into a counting tube. The measurement is made in a γ-counter for 1 minute/sample.

The evaluation of the samples is carried out after calculating the specific bond in comparison to untreated cells, after the unspecific bond (excess unlabeled ligand, 1 mmol) is removed by means of GraphPad Prism (GraphPad Software Inc., USA).

Functional Reporter Gene Assay

Materials:

All chemicals are ordered from commercial sources at the highest available purity.

Cell Culture:

For performing functional tests, stable, transfixed LTK cells carrying GnRH receptors (ATCC No. CCL-1.3) with a heterologous expression of cAMP responsible elements as well as a CMV minimal promoter-driven luciferase reporter gene are used.

The cells are cultivated in DMEM medium (Invitrogen Life Technologies, Germany) with penicillin (100 I.U./ml), streptomycin (0.1 mg/ml) and glutamine (0.01 mol/l) and 10% fetal calf serum (FCS; Invitrogen Life Technologies, Germany) on plastic tissue culture plates (Nunc, Germany, 245×245×20 mm).

Testing:

80% confluent cell culture plates are washed twice with 50 ml of phosphate-buffered salt solution (PBS) and subsequently dissolved with trypsin EDTA solution (Invitrogen Life Technologies, Germany). The cells are pelletized by centrifuging at 200×g for 5 minutes in a laboratory centrifuge (Kendro, Germany). The cell pellet is resuspended in 3 ml of assay medium (Invitrogen Life Technologies, Germany) with penicillin (100 I.U./ml), streptomycin (0.1 mg/ml) and glutamine (0.01 mol/l) and 10% fetal calf serum (FCS; Invitrogen Life Technologies, Germany), and the cell count is determined by means of trypan blue staining in a Neubauer counting chamber. The cell suspension is set with assay medium to a concentration of $1\times10^4$ Z/100 µl. The cells are suspended on white 96-well microtiter plates (Costar, Germany) and incubated for 18 hours in an incubator.

To perform tests, test substances are diluted as 10 mmol DMSO solutions in assay medium to 6× the final concentration used. 25 µl of the test substance is added to 100 µl cells and incubated for 60 minutes at 37° C., 5% $CO_2$. Then, the addition of triptorelin (D-Trp6-GnRH)/Rolipram solution (6 mmol/6 mmol) and a renewed incubation are carried out for 6 hours at 37° C., 5% $CO_2$.

After incubation, the addition of 50 µl of lysis/detection buffer (LucLite, PE Life Science) and the measurement in a Lumistar luminometer (BMG Labtechnologies GmBH, Germany) are carried out.

The evaluation of the samples is carried out after calculating the inhibition in comparison to untreated stimulated cells, after removal of non-stimulated controls, by means of GraphPad Prism (GraphPad Software, Inc., USA) or alternately by means of OMMM (Accelrys, Germany) Software.

In the table below, $EC_{50}$-values obtained for compounds 293 to 306 are indicated.

| Compound Name | Example No. | Functional Human $EC_{50}$ [M] | Human Binding Triptorelin $EC_{50}$ [M] |
|---|---|---|---|
| Phenylmethyl [(1S,2S)-1-[[[(3R)-3-[[[(1S)-1-(aminocarbonyl)-2-methylpropyl]amino]-carbonyl]-6,8-difluoro-2,3,4,9-tetrahydro-1H-carbazol-3-yl[amino]carbonyl]-2-methylbutyl]-carbamate | 293 | 0.000000762 | 0.000000332 |
| Phenylmethyl [(1S,2S)-1-[[[(3R)-3-[[[(1S,2S)-1-(aminocarbonyl)-2-methylbutyl]amino]-carbonyl]-8-methoxy-2,3,4,9-tetrahydro-1H-carbazol-3-yl]amino]carbonyl]-2-methylbutyl]-carbamate | 294 | 0.000000089 | 0.000000036 |
| Phenylmethyl [(1S,2S)-1-[[[(3R)-3-[[[(1S,2S)-1-(aminocarbonyl)-2-methylbutyl]amino]-carbonyl]-6,8-dicloro-2,3,4,9-tetrahydro-1H-carbazol-3-yl]amino]carbonyl]-2-methylbutyl]-carbamate | 295 | 0.000000007 | 0.000000018 |
| Phenylmethyl [(1S,2S)-1-[[[(3R)-3-[[[(1S)-1-(aminocarbonyl)-3-methylbutyl]amino]-carbonyl]-6,8-dichloro-2,3,4,9-tetrahydro-1H-carbazol-3-yl]amino]carbonyl]-2-methylbutyl]-carbamate | 296 | 0.000000014 | 0.000000022 |
| Phenylmethyl (1S,2S)-1-[[[(3R)-3-[[[(1S)-1-(aminocarbonyl)-2-cyclohexylethyl]amino]-carbonyl]-6,8-dichloro-2,3,4,9-tetrahydro-1H-carbazol-3-yl]amino]carbonyl]-2-methylbutyl]carbamate | 297 | 0.000000284 | 0.000000482 |
| Phenylmethyl [(1S,2S)-1-[[[(3R)-3-[[[(1S)-1-(aminocarbonyl)-2,2-dimethylpropyl]amino]-carbonyl]-6,8-dichloro-2,3,4,9-tetrahydro-1H-carbazol-3-yl]amino]carbonyl]-2-methylbutyl]-carbamate | 298 | | 0.000000288 |
| Phenylmethyl [(1S,2S)-1-[[[(3R)-3-[[[(1S)-1-(aminocarbonyl)-3-phenylpropyl]-amino]carbonyl]-6,8-dichloro-2,3,4,9-tetrahydro-1H-carbazol-3-yl]amino]carbonyl]-2-methylbutyl]carbamate | 299 | 0.000001497 | 0.000001307 |
| Phenylmethyl [(1S,2S)-1-[[[(3R)-3-[[[(1S)-1-(aminocarbonyl)-2-methylbutyl]amino]-carbonyl]-6,8-dichloro-2,3,4,9-tetrahydro-1H-carbazol-3-yl]amino]carbonyl]-2-cyclohexyl-methyl]carbamate | 300 | 0.000000017 | 0.000000023 |
| Phenylmethyl [(1S,2S)-1-[[[(3R)-3-[[[(1S,2S)-1-(carboxy)-2-methylbutyl]amino]carbonyl]-6,8-dichloro-2,3,4,9-tetrahydro-1H-carbazol-3-yl]amino]carbonyl]-2-methylbutyl]carbamate | 301 | 0.000000176 | 0.000000538 |

-continued

| Compound Name | Example No. | Functional Human EC$_{50}$ [M] | Human Binding Triptorelin EC$_{50}$ [M] |
| --- | --- | --- | --- |
| Phenylmethyl [(1S)-1-[[[(3R)-3-[[[(1S,2S)-1-(aminocarbonyl)-2-methylbutyl]amino]-carbonyl]-6,8-dichloro-2,3,4,9-tetrahydro-1H-carbazol-3-yl]amino]carbonyl]-2-(4-hydroxyphenyl)ethyl]carbamate | 302 | 0.000000324 | 0.000000475 |
| Phenylmethyl [(1S)-1-([[(3R)-3-[[[(1S,2S)-1-(aminocarbonyl)-2-methylbutyl]amino]-carbonyl]-6,8-dichloro-2,3,4,9-tetrahydro-1H-carbazol-3-yl]amino]carbonyl]-3-(4-hydroxyphenyl)propyl]carbamate | 303 | | 0.000000021 |
| Phenylmethyl [(1S)-1-[[[(3R)-3-[[[(1S,2S)-1-(aminocarbonyl)-2-methylbutyl]amino]-carbonyl]-6,8-dichloro-2,3,4,9-tetrahydro-1H-carbazol-3-yl]amino]carbonyl]-3-phenylpropyl]carbamate | 304 | 0.000000018 | 0.000000038 |
| Phenylmethyl [(1S)-1-[[[(3R)-3-[[[(1S,2S)-1-(aminocarbonyl)-2-methylbutyl]amino]-carbonyl]-6,8-dichloro-2,3,4,9-tetrahydro-1H-carbazol-3-yl]amino]carbonyl]-3-methylbutyl]carbamate | 305 | | 0.000000056 |
| Phenylmethyl [(1S)-1-[[[(3R)-3-[[[(1S)-1-(aminocarbonyl)-3-methylbutyl]amino]-carbonyl]-6,8-dichloro-2,3,4,9-tetrahydro-1H-carbazol-3-yl]amino]carbonyl]-3-methylbutyl]carbamate | 306 | | 0.000000077 |

The entire disclosures of all applications, patents and publications, cited herein and of corresponding German Application No. 101 64 564.3, filed Dec. 14, 2001, and U.S. Provisional Application Ser. No. 60/341,878, filed Dec. 21, 2001, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of formula (I)

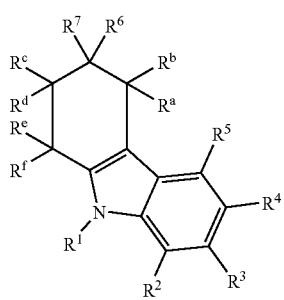

(I)

in which
radical $R^1$ is a hydrogen atom, a $C_2$–$C_6$ alkenyl radical or a $C_1$–$C_6$ alkyl radical, and can optionally be substituted with an aryl radical, hetaryl radical or —COOR$^{11}$, wherein the aryl or hetaryl radical can be substituted with up to three substituents, which, independently of one another, are —NO$_2$, —CH$_3$, —CF$_3$, —OCH$_3$, —OCF$_3$ or a halogen atom, and radical $R^{11}$ is a hydrogen atom, a $C_1$–$C_{12}$ alkyl radical, a $C_1$–$C_{12}$ alkyl radical that is substituted by one or more aryl radicals, an aryl radical, a hetaryl radical or —COCH$_3$, and optionally can be substituted with a substituent that is —CONH$_2$, —COCH$_3$, —COOCH$_3$, —SO$_2$CH$_3$ or an aryl radical;

radicals $R^2$, $R^3$ and $R^5$, each independently of one another, are a hydrogen atom, a halogen atom, —COOH, —CONH$_2$, —CF$_3$, —OCF$_3$, —NO$_2$, —CN, a $C_1$–$C_6$ alkyl radical, a $C_2$–$C_6$ alkenyl radical, a $C_1$–$C_6$ alkoxy radical, a $C_1$–$C_{12}$ alkyl radical that is substituted by one or more aryl radicals, an aryl or hetaryl radical;

radical $R^4$ is a hydrogen atom, a halogen atom, —COOH, —CONH$_2$, —CF$_3$, —OCF$_3$, —NO$_2$, —CN, a $C_1$–$C_6$ alkyl radical, a $C_2$–$C_6$ alkenyl radical, a $C_1$–$C_{12}$ alkyl radical that is substituted by one or more aryl radicals, an aryl or hetaryl radical;

radical $R^6$ is —CONR$^8$R$^9$, —COOR$^8$, —CH$_2$NR$^8$R$^9$, —CH$^2$OR$^8$ or a $C_2$–$C_{12}$ alkenyl radical, which optionally is substituted with radicals $R^8$ and $R^9$, radicals $R^8$ and $R^9$, each independently of one another, are a hydrogen atom, a $C_1$–$C_{12}$ alkyl radical, a $C_1$–$C_{12}$ alkyl radical that is substituted by one or more aryl radicals, a $C_1$–$C_{12}$ alkyl radical that is substituted by a hetaryl radical, an aryl radical or hetaryl radical, which can be substituted with one or more substituents, which are each independently —OH, —NH$_2$, —CONHR$^{10}$, —COOR$^{10}$, —NH—C(=NH)—NH$_2$ or a halogen atom, radical $R^{10}$ is a hydrogen atom, a $C_1$–$C_{12}$ alkyl radical, a $C_1$–$C_{12}$ alkyl radical that is substituted by one or more aryl radicals, an aryl radical or hetaryl radical, and optionally is substituted with —CON(R$^{11}$)$_2$, or radicals $R^8$ and $R^9$ together can form a ring structure that either consists exclusively of carbon atoms or consists of carbon atoms and heteroatoms;

radical $R^7$ is a $C_1$–$C_{12}$ alkyl radical that is substituted by one or more aryl radicals, or a hetaryl radical, —$NR^{12}R^{13}$, —$NHCOR^{14}$, —$NHCONHR^{14}$, —$NHCOOR^{14}$ or $NHSO_2R^{14}$, and optionally can be substituted with one or more substituents, which are each independently —OH, —$NH_2$, —$CONH_2$, —COOH or a halogen atom, radicals $R^{12}$ and $R^{13}$, each independently of one another, are a hydrogen atom, a $C_2$–$C_6$ alkenyl radical or a $C_1$–$C_{12}$ alkyl radical and optionally can be substituted with one or more aryl or hetaryl radicals, which in turn can be substituted with up to three substituents, which independently of one another are —$NO_2$, —$CH_3$, —$CF_3$, —$OCH_3$, —$OCF_3$ or a halogen atom, radical $R^{14}$ is a hydrogen atom, a $C_1$–$C_{12}$ alkyl radical, a $C_2$–$C_{12}$ alkenyl radical, a $C_1$–$C_{12}$ alkyl radical that is substituted by one or more aryl radicals, an aryl radical or a hetaryl radical, which optionally can be substituted with one or more substituents —$NO_2$, —$CH_3$, —$OR^{11}$, —$CF3$, —$OCF_3$, —OH, —$N(R^{11})_2$, —$OCOR^{11}$, —COOH, —$CONH_2$, —$NHCONHR^{11}$, —$NHCOOR^{11}$ or a halogen atom;

and radicals $R^a$, $R^b$, $R^c$, $R^d$, $R^e$ and $R^f$, each independently of one another, are a hydrogen atom, a halogen atom, —COOH, —$CONH_2$, —$CF_3$, —$OCF_3$, —$NO_2$, —CN, a $C_1$–$C_6$ alkyl radical, a $C_1$–$C_6$ alkoxy radical, an aryl radical or a hetaryl radical;

provided that the compound of formula (I) is not 3-amino-1,2,3,4-tetrahydrocarbazole-3-carboxylic acid, 3-acetamido-1,2,3,4-tetrahydrocarbazole-3-carboxylic acid, methyl-3-acetamido-1,2,3,4-tetrahydrocarbazole-3-carboxylate, -(−)-menthyl-3-acetamido-1,2,3,4-tetrahydrocarbazole-3-carboxylate or 3-tert-butoxycarbonyl-amino-1,2,3,4-tetrahydrocarbazole-3-carboxylic acid.

2. A compound according to claim 1, wherein radicals $R^a$, $R^b$, $R^c$, $R^d$, $R^e$ and $R^f$ are hydrogen atoms.

3. A compound according to claim 1, wherein radical $R^1$ is a hydrogen atom.

4. A compound according to claim 1, wherein radicals $R^2$, $R^3$, $R^4$ and/or $R^5$ are not hydrogen atoms.

5. A compound according to claim 4, wherein radicals $R^2$, $R^3$, and $R^5$, independently of one another, are the group —$CH_3$, —Cl or —$OCH_3$, and $R^4$ is —$CH_3$ or Cl.

6. A compound according to claim 1, which is
Phenylmethyl-[(1S,2S)-1-[[[(3R)-3-[[[(1S)-1-(aminocarbonyl)-2-methylpropyl]amino]carbonyl]-2,3,4,9-tetrahydro-8-methyl-1H-carbazol-3-yl]amino]carbonyl]-2-methylbutyl]-carbamate,
Phenylmethyl-[(1S,2S)-1-[[[(3R)-3-[[[(1S)-1-(aminocarbonyl)-2-methylpropyl]amino]carbonyl]-6-chloro-2,3,4,9-tetrahydro-1H-carbazol-3-yl]amino]-carbonyl]-2-methylbutyl]carbamate, or
Phenylmethyl-[(1S,2S)-1-[[[(3R)-3-[[[(1S)-1-(aminocarbonyl)-2-methylpropyl]amino]carbonyl]-2,3,4,9-tetrahydro-8-methoxy-1H-carbazol-3-yl]amino]carbonyl]-2-methylbutyl]carbamate.

7. A compound according to claim 1, wherein radical $R^6$ is a carbonyl phenylalanylamide radical, a carbonyl isoleucylamide radical, a carbonyl valyl-4-aminobenzoic acid amide radical, a carbonyl valyl-N-methylamide radical, a methyloxymethyl-4-pyridyl radical, a carboxyl radical, a propenoic acid ethyl ester radical, a carbonylvalylamide radical, a carbonylthreonylamide radical, a cyclic carboxamide radical, a 4-carboxamidophenylcarboxamide radical, a methylaminomethyl-2-pyridyl radical, a carbonylvalinol radical, or a methylvalinol radical.

8. A compound according to claim 7, which is
Phenylmethyl-[(1S,2S)-1-[[[(3R)-3-[[[(1S)-2-amino-2-oxo-1-(phenylmethyl)ethyl]amino]-carbonyl]-2,3,4,9-tetrahydro-1H-carbazol-3-yl]amino]carbonyl]-2-methylbutyl]-carbamate,
Phenylmethyl-[(1S,2S)-1-[[[(3R)-3-[[[(1S,2S)-1-(aminocarbonyl)-2-methylbutyl]amino]carbonyl]-2,3,4,9-tetrahydro-1H-carbazol-3-yl]amino]-carbonyl]-2-methylbutyl]carbamate,
Phenylmethyl-[(1S,2S)-1-[[[(3R)-3-[[[(1S)-1-[[[4-(aminocarbonyl)-phenyl]amino]carbonyl]-2-methylpropyl]amino]carbonyl]-2,3,4,9-tetrahydro-1H-carbazol-3-yl]amino]carbonyl]-2-methylbutyl]carbamate,
Phenylmethyl-[(1S,2S)-2-methyl-1-[[[(3R)-2,3,4,9-tetrahydro-3-[[[(1S)-2-methyl-1-[(methylamino)carbonyl]propyl]amino]carbonyl]-1H-carbazol-3-yl]amino]carbonyl]butyl]carbamate,
2,3,4,9-Tetrahydro-3-(3-phenylpropyl)-O-(4-pyridinylmethyl)-1H-carbazole-3-methanol,
2,3,4,9-Tetrahydro-3-(3-phenylpropyl)-1H-carbazole-3-carboxylic acid, Ethyl-3-[2,3,4,9-tetrahydro-3-(3-phenylpropyl)-1H-carbazol-3-yl]-2-propenoate,
Phenylmethyl-[(1S,2S)-1-[[[(3R)-3-[[[(1S)-1-(aminocarbonyl)-2-methylpropyl]amino]carbonyl]-2,3,4,9-tetrahydro-1H-carbazol-3-yl]amino]carbonyl]-2-methylbutyl]carbamate,
Phenylmethyl [(1S,2S)-1-[[[(3R)-3-[[[(1S,2R)-1-(aminocarbonyl)-2-hydroxypropyl]amino]carbonyl]-2,3,4,9-tetrahydro-1H-carbazol-3-yl]amino]carbonyl]-2-methylbutyl]carbamate,
Phenylmethyl-[(1S,2S)-1-[[[(3R)-3-[[(2S)-2-(aminocarbonyl)-1-pyrrolidinyl]carbonyl]-2,3,4,9-tetrahydro-1H-carbazol-3-yl]amino]carbonyl]-2-methylbutyl]carbamate,
Phenylmethyl-[(1S,2S)-1-[[[(3R)-3-[[(2S)-2-(aminocarbonyl)octahydro-1H-indol-1-yl]carbonyl]-2,3,4,9-tetrahydro-1H-carbazol-3-yl]amino]carbonyl]-2-methylbutyl]carbamate),
Phenylmethyl [(1S,2S)-1-[[[(3R)-3-[[[4-(aminocarbonyl)phenyl]amino]-carbonyl]-2,3,4,9-tetrahydro-1H-carbazol-3-yl]amino]carbonyl]-2-methylbutyl]carbamate,
2,3,4,9-Tetrahydro-3-(3-phenylpropyl)-N-(2-pyridinylmethyl)-1H-carbazole-3-methanamine,
Phenylmethyl-[(1S,2S)-1-[[[(3S)-3-[[[(1S)-1-(hydroxymethyl)-2-methylpropyl]amino]carbonyl]-2,3,4,9-tetrahydro-1H-carbazol-3-yl]amino]carbonyl]-2-methylbutyl]carbamate,
2,3,4,9-Tetrahydro-N-[(1S)-1-(hydroxymethyl)-2-methylpropyl]-3-(3-phenylpropyl)-1H-carbazole-3-carboxamide or
(2S)-3-Methyl-2-[[[2,3,4,9-tetrahydro-3-(3-phenylpropyl)-1H-carbazol-3-yl]methyl]amino]-1-butanol.

9. A compound according to claim 1, wherein radical $R^7$ is a 2,3-biphenylpropionylamino radical, an indanoylamino radical, an indolylacetylamino radical, a 2-naphthylacetylamino radical, a 3-propionylamino radical, a phenylmethylcarboxamide radical that is substituted on an aromatic system, a phenylhexylamine radical or a phenylpropyl radical.

10. A compound according to claim 9, which is
N-[[(3R)-2,3,4,9-Tetrahydro-3-[(1-oxo-2,3-diphenylpropyl)amino]-1H-carbazol-3-yl]carbonyl]-L-valyl-L-aspartamide,
(3R)-N-[(1S)-1-(Aminocarbonyl)-2-methylpropyl]-3-[[(2,3-dihydro-1H-inden-1-yl)carbonyl]amino]-2,3,4,9-tetrahydro-1H-carbazole-3-carboxamide, (3S)-N-[(1S)-1-(Aminocarbonyl)-2-methylpropyl]-2,3,4,9-tetrahydro-3-[(1H-indol-3-ylacetyl)amino]-1H-carbazole-3-carboxamide, (3S)-N-[(1S)-1-(Aminocarbonyl)-2-methylpropyl]-2,3,4,9-tetrahydro-3-[(2-naphthalenylacetyl)amino]-1H-carbazole-3-carboxamide, (3R)-N-[(1S)-1-(Aminocarbonyl)-2-methylpropyl]-2,3,4,9-tetrahydro-3-[[(4-methylphenyl)acetyl]amino]-1H-carbazole-3-carboxamide, N-[(1S)-1-(Aminocarbonyl)-2-methylpropyl]-2,3,4,9-tetrahydro-3-[[(4-methoxy-phenyl)-acetyl]amino]-1H-carbazole-3-carboxamide, (3R)-N-[(1S)-1-(Aminocarbonyl)-2-methylpropyl]-3-[[(3-bromophenyl)acetyl]-amino]-2,3,4,9-tetrahydro-1H-carbazole-3-carboxamide, (3R)-N-[(1S)-1-(Aminocarbonyl)-2-methylpropyl]-3-[[(4-fluorophenyl)acetyl]-amino]-2,3,4,9-tetrahydro-1H-carbazole-3-carboxamide, (3R)-N-[(1S)-1-(Aminocarbonyl)-2-methylpropyl]-3-[[(4-chlorophenyl)acetyl]-amino]-2,3,4,9-tetrahydro-1H-carbazole-3-carboxamide, (3R)-N-[(1S)-1-(Aminocarbonyl)-2-methylpropyl]-2,3,4,9-tetrahydro-3-[(6-phenylhexyl)amino]-1H-carbazole-3-carboxamide, 6,8-Dichloro-2,3,4,9-tetrahydro-3-(3-phenylpropyl)-1H-carbazole-3-carboxylic acid or Ethyl-6,8-dichloro-2,3,4,9-tetrahydro-3-(3-phenylpropyl)-1H-carbazole-3-carboxylate.

11. A compound according to claim 1, wherein the compound is present in R-configuration in the carbon atom that is substituted by radicals $R^6$ and $R^7$, if radicals $R^6$ and $R^7$ together form an alpha-aminocarboxylic acid.

12. A compound according to claim 1, which is
Phenylmethyl-[(1S,2S)-1-[[[(3R)-3-[[[(1S)-1-(aminocarbonyl)-2-methylpropyl]amino]carbonyl]-6,8-dichloro-2,3,4,9-tetrahydro-1H-carbazol-3-yl]amino]carbonyl]-2-methyl-butyl]carbamate, Phenylmethyl-[(1S,2S)-1-[[[(3R)-3-[[[(1S)-1-(hydroxymethyl)-2-methylpropyl]-amino]carbonyl]-2,3,4,9-tetrahydro-1H-carbazol-3-yl]amino]carbonyl]-2-methylbutyl]carbamate, (2S)-1-[[(3R)-3-[[(4-Chlorophenyl)acetyl]amino]-2,3,4,9-tetrahydro-8-methoxy-1H-carbazol-3-yl]carbonyl]-2-pyrrolidinecarboxamide or 6,8-Dichloro-2,3,4,9-tetrahydro-3-(3-phenylpropyl)-N-(2-pyridinylmethyl)-1H-carbazole-3-methanamine.

13. A pharmaceutical composition that comprises at least one compound according to claim 1 and a vehicle, diluent or adjuvant.

14. A pharmaceutical composition according to claim 13, wherein the compound of formula I is present in a unit dose of 1 μg to 100 mg per kg of body weight of a patient.

15. A pharmaceutical composition according to claim 13, wherein the compound of formula I is present in combination with at least one other pharmaceutical active ingredient.

16. A compound according to claim 1, which is
Phenylmethyl [(1S,2S)-1-[[[(3R)-3-[[[(1S)-1-(aminocarbonyl)-2-methylpropyl]amino]carbonyl]-6,8-difluoro-2,3,4,9-tetrahydro-1H-carbazol-3-yl]amino]carbonyl]-2-methylbutyl]carbamate Phenylmethyl [(1S,2S)-1-[[[(3R)-3-[[[(1S,2S)-1-(aminocarbonyl)-2-methylbutyl]amino]carbonyl]-8-methoxy-2,3,4,9-tetrahydro-1H-carbazol-3-yl]amino]carbonyl]2-methylbutyl]carbamate Phenylmethyl [(1S,2S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-2-methylbutyl]carbamate Phenylmethyl [(1S,2S)-1-[[[(3R)-3-[[[(1S)-1-(aminocarbonyl)-3-methylbutyl]amino]carbonyl]-6,8-dichloro-2,3,4,9-tetrahydro-1H-carbazol-3-yl]amino]carbonyl]-2-methylbutyl]carbamate Phenylmethyl [(1S,2S)-1-[[[(3R)-3-[[[(1S)-1-(aminocarbonyl)-2-cyclohexylethyl]amino]carbonyl]-6,8-dichloro-2,3,4,9-tetrahydro-1H-carbazol-3-yl]amino]carbonyl]-2-methylbutyl]carbamate Phenylmethyl [(1S,2S)-1-[[[(3R)-3-[[[(1S)-1-(aminocarbonyl)-2,2-dimethylpropyl]amino]carbonyl]-6,8-dichloro-2,3,4,9-tetrahydro-1H-carbazol-3-yl]amino]carbonyl]-2-methylbutyl]carbamate Phenylmethyl [(1S,2S)-1-[[[(3R)-3-[[[(1S)-1-(aminocarbonyl)-3-phenylpropyl]amino]carbonyl]-6,8-dichloro-2,3,4,9-tetrahydro-1H-carbazol-3-yl]amino]carbonyl]-2-methylbutyl]carbamate Phenylmethyl [(1S,2S)-1-[[[(3R)-3-[[[(1S)-1-(aminocarbonyl)-2-methylbutyl]amino]carbonyl]-6,8-dichloro-2,3,4,9-tetrahydro-1H-carbazol-3-yl]amino]carbonyl]-2-cyclohexylmethyl]carbamate Phenylmethyl [(1S,2S)-1-[[[(3R)-3-[[[(1S,2S)-1-(carboxy)-2-methylbutyl]amino]carbonyl]-6,8-dichloro-2,3,4,9-tetrahydro-1H-carbazol-3-yl]amino]carbonyl]-2-methylbutyl]carbamate Phenylmethyl [(1S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-2-(4-hydroxyphenyl)ethyl]carbamate Phenylmethyl [(1S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-3-(4-hydroxyphenyl)propyl]carbamate Phenylmethyl [(1S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-3-phenylpropyl]carbamate Phenylmethyl [(1S)-1-[[[(3R)-3-[[[(1S,2S)-1-(aminocarbonyl)-2-methylbutyl]amino]carbonyl]-6,8-dichloro-2,3,4,9-tetrahydro-1H-carbazol-3-yl]amino]carbonyl]-3-methylbutyl]carbamate or Phenylmethyl [(1S)-1-[[[(3R)-3-[[[(1S)-1-(aminocarbonyl)-3-methylbutyl]amino]carbonyl]-6,8-dichloro-2,3,4,9-tetrahydro-1H-carbazol-3-yl]amino]carbonyl]-3-methylbutyl]carbamate.

17. A pharmaceutical composition that comprises at least one compound according to claim 16, and a vehicle, diluent or adjuvant.

18. A pharmaceutical composition according to claim 17, wherein the compound of formula I is present in a unit dose of 1 μg to 10 mg per kg of body weight of a patient.

19. A pharmaceutical composition according to claim 17, wherein the compound of formula I is present in combination with at least one other pharmaceutical active ingredient.

20. N-[[(3R)-2,3,4,9-Tetrahydro-3-[[(2S,3S)-3-methyl-1-oxo-2-[(1-oxo-3-phenyl-propyl)amino]pentyl]amino]-1H-carbazol-3-yl]carbonyl]-L-valyl-L-aspartamide.

* * * * *